(12) United States Patent
Fairhurst et al.

(10) Patent No.: US 8,357,707 B2
(45) Date of Patent: Jan. 22, 2013

(54) 2-CARBOXAMIDE CYCLOAMINO UREAS

(75) Inventors: Robin Alec Fairhurst, Basel (CH); Marc Gerspacher, Basel (CH); Robert Mah, Basel (CH)

(73) Assignee: Novartis AG, Basel (CH)

( * ) Notice: Subject to any disclaimer, the term of this patent is extended or adjusted under 35 U.S.C. 154(b) by 146 days.

(21) Appl. No.: 12/829,526

(22) Filed: Jul. 2, 2010

(65) Prior Publication Data

US 2011/0003786 A1    Jan. 6, 2011

Related U.S. Application Data

(60) Provisional application No. 61/270,028, filed on Jul. 2, 2009.

(51) Int. Cl.
*A01N 43/78* (2006.01)
*A61K 31/425* (2006.01)

(52) U.S. Cl. ............... 514/366; 514/210.18; 514/267; 514/293; 548/151; 544/133; 544/115; 544/250

(58) Field of Classification Search ............ 514/210.18, 514/267, 293, 366; 548/151; 544/133, 115, 544/250

See application file for complete search history.

(56) References Cited

U.S. PATENT DOCUMENTS

| | | | |
|---|---|---|---|
| 7,517,995 B2 | 4/2009 | Breitfelder | |
| 2006/0100254 A1 | 5/2006 | Betzemeier et al. | |
| 2006/0106013 A1 | 5/2006 | Breitfelder et al. | |
| 2007/0238746 A1 | 10/2007 | Brandl et al. | |
| 2007/0244104 A1 | 10/2007 | Brandl et al. | |
| 2009/0030024 A1 | 1/2009 | Greul et al. | |
| 2009/0163469 A1* | 6/2009 | Caravatti et al. | 514/210.18 |
| 2009/0247567 A1* | 10/2009 | Do et al. | 514/291 |

FOREIGN PATENT DOCUMENTS

| | | |
|---|---|---|
| CA | 2579288 A1 | 4/2006 |
| DE | 102004048877 A1 | 4/2006 |
| JP | 57175189 A | 10/1982 |
| WO | WO 03/072557 A1 | 9/2003 |
| WO | WO 2004/045518 A2 | 6/2004 |
| WO | WO 2004/078754 A1 | 9/2004 |
| WO | WO 2004/096797 A1 | 11/2004 |
| WO | WO 2005/005438 A1 | 1/2005 |
| WO | WO 2005/021519 A2 | 3/2005 |
| WO | WO 2005/026137 A2 | 3/2005 |
| WO | WO 2005/068444 A2 | 7/2005 |
| WO | WO 2006/051270 A1 | 5/2006 |
| WO | WO 2006/125805 A1 | 11/2006 |
| WO | WO 2007/068473 A2 | 6/2007 |
| WO | WO 2007/070600 A2 | 6/2007 |
| WO | WO 2007/082956 A1 | 7/2007 |
| WO | WO 2007/095588 A1 | 8/2007 |
| WO | WO 2008/064054 A2 | 5/2008 |
| WO | WO 2008/064218 A2 | 5/2008 |
| WO | WO 2008/124000 A2 | 10/2008 |
| WO | WO 2009/003009 A1 | 12/2008 |

OTHER PUBLICATIONS

Jordan, V. C. Nature Reviews: Drug Discovery, 2, 2003, pp. 205-213).*
Souillac, et al., Characterization of Delivery Systems, Differential Scanning Calorimetry, in Encyclopedia of Controlled Drug Delivery, 1999, John Wiley & Sons, pp. 212-227.*
(Dörwald, F. Zaragoza. Side Reactions in Organic Synthesis: A Guide to Successful Synthesis Design, Weinheim: WILEY-VCH Verlag GmbH & Co. KGaA, 2005, Preface.*
Wolff, Manfred E. "Burger's Medicinal Chemistry, 5ed, Part I", John Wiley & Sons, 1995, pp. 975-977.*
Banker et al, "Modern Pharmaceutics, 3ed.", Marcel Dekker, New York, 1996, pp. 451 and 596.*
Morissette et al. Advanced Drug Delivery Reviews 2004, 56, 275-300.*
Vippagunta et al. Advanced Drug Delivery Reviews 2001, 48, 3-26.*
B. Rodriguez-Spong et al. (Advanced Drug Delivery Reviews, 2004, 56, pp. 241-274.*
Berge et al. J. Pharm. Sci. 1977, 66, 1-19.*
Mang et al; "Natural Products in Combinatorial Chemistry: An Andrographolide-based Library"; J. Comb. Chem. 8:268-274 (2006).

* cited by examiner

*Primary Examiner* — Yong Chu
*Assistant Examiner* — Valerie Rodriguez-Garcia
(74) *Attorney, Agent, or Firm* — Scott W. Reid

(57) ABSTRACT

The present invention relates to compounds of formula I

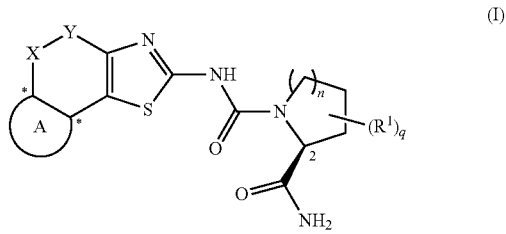

and salts thereof, wherein the substituents are as defined in the description, to compositions and use of the compounds in the treatment of diseases ameliorated by inhibition of phosphatidylinositol 3-kinase.

11 Claims, No Drawings

SEQUENCE LISTING

<160> NUMBER OF SEQ ID NOS: 20

<210> SEQ ID NO 1
<211> LENGTH: 42
<212> TYPE: DNA
<213> ORGANISM: Artificial
<220> FEATURE:
<223> OTHER INFORMATION: PCR Primer

<400> SEQUENCE: 1
gctagcatgc gagaatatga tagattatat gaagaatata cc                42

<210> SEQ ID NO 2
<211> LENGTH: 45
<212> TYPE: DNA
<213> ORGANISM: Artificial
<220> FEATURE:
<223> OTHER INFORMATION: PCR primer

<400> SEQUENCE: 2
gcctccacca cctccgcctg gtttaatgct gttcatacgt ttgtc             45

<210> SEQ ID NO 3
<211> LENGTH: 42
<212> TYPE: DNA
<213> ORGANISM: Artificial
<220> FEATURE:
<223> OTHER INFORMATION: PCR primer

<400> SEQUENCE: 3
tactagtccg cctccaccac ctccgcctcc accacctccg cc                42

<210> SEQ ID NO 4
<211> LENGTH: 1180

```
<212> TYPE: PRT
<213> ORGANISM: Artificial
<220> FEATURE:
<223> OTHER INFORMATION: PI3K kinase construct

<400> SEQUENCE: 4
```

| | | | | | | | | | | | | | | | |
|---|---|---|---|---|---|---|---|---|---|---|---|---|---|---|---|
| Met | Arg | Glu | Tyr | Asp | Arg | Leu | Tyr | Glu | Glu | Tyr | Thr | Arg | Thr | Ser | Gln |
| 1 | | | | 5 | | | | | 10 | | | | | 15 | |
| Glu | Ile | Gln | Met | Lys | Arg | Thr | Ala | Ile | Glu | Ala | Phe | Asn | Glu | Thr | Ile |
| | | | 20 | | | | | 25 | | | | | 30 | | |
| Lys | Ile | Phe | Glu | Glu | Gln | Cys | Gln | Thr | Gln | Glu | Arg | Tyr | Ser | Lys | Glu |
| | | | 35 | | | | | 40 | | | | | 45 | | |
| Tyr | Ile | Glu | Lys | Phe | Lys | Arg | Glu | Gly | Asn | Glu | Lys | Glu | Ile | Gln | Arg |
| | | 50 | | | | | 55 | | | | | 60 | | | |
| Ile | Met | His | Asn | Tyr | Asp | Lys | Leu | Lys | Ser | Arg | Ile | Ser | Glu | Ile | Ile |
| 65 | | | | | 70 | | | | | 75 | | | | | 80 |
| Asp | Ser | Arg | Arg | Arg | Leu | Glu | Glu | Asp | Leu | Lys | Lys | Gln | Ala | Ala | Glu |
| | | | | 85 | | | | | 90 | | | | | 95 | |
| Tyr | Arg | Glu | Ile | Asp | Lys | Arg | Met | Asn | Ser | Ile | Lys | Pro | Gly | Gly | Gly |
| | | | 100 | | | | | 105 | | | | | 110 | | |
| Gly | Gly | Gly | Gly | Gly | Gly | Gly | Leu | Val | Glu | Cys | Leu | Leu | Pro |
| | | 115 | | | | | 120 | | | | | 125 | |
| Asn | Gly | Met | Ile | Val | Thr | Leu | Glu | Cys | Leu | Arg | Glu | Ala | Thr | Leu | Ile |
| | | 130 | | | | | 135 | | | | | 140 | | | |
| Thr | Ile | Lys | His | Glu | Leu | Phe | Lys | Glu | Ala | Arg | Lys | Tyr | Pro | Leu | His |
| 145 | | | | | 150 | | | | | 155 | | | | | 160 |
| Gln | Leu | Leu | Gln | Asp | Glu | Ser | Ser | Tyr | Ile | Phe | Val | Ser | Val | Thr | Gln |
| | | | | 165 | | | | | 170 | | | | | 175 | |
| Glu | Ala | Glu | Arg | Glu | Glu | Phe | Phe | Asp | Glu | Thr | Arg | Arg | Leu | Cys | Asp |
| | | | 180 | | | | | 185 | | | | | 190 | | |
| Leu | Arg | Leu | Phe | Gln | Pro | Phe | Leu | Lys | Val | Ile | Glu | Pro | Val | Gly | Asn |
| | | | 195 | | | | | 200 | | | | | 205 | | |
| Arg | Glu | Glu | Lys | Ile | Leu | Asn | Arg | Glu | Ile | Gly | Phe | Ala | Ile | Gly | Met |
| | | 210 | | | | | 215 | | | | | 220 | | | |
| Pro | Val | Cys | Glu | Phe | Asp | Met | Val | Lys | Asp | Pro | Glu | Val | Gln | Asp | Phe |
| 225 | | | | | 230 | | | | | 235 | | | | | 240 |
| Arg | Arg | Asn | Ile | Leu | Asn | Val | Cys | Lys | Glu | Ala | Val | Asp | Leu | Arg | Asp |
| | | | | 245 | | | | | 250 | | | | | 255 | |
| Leu | Asn | Ser | Pro | His | Ser | Arg | Ala | Met | Tyr | Val | Tyr | Pro | Pro | Asn | Val |
| | | | 260 | | | | | 265 | | | | | 270 | | |
| Glu | Ser | Ser | Pro | Glu | Leu | Pro | Lys | His | Ile | Tyr | Asn | Lys | Leu | Asp | Lys |
| | | | 275 | | | | | 280 | | | | | 285 | | |
| Gly | Gln | Ile | Ile | Val | Val | Ile | Trp | Val | Ile | Val | Ser | Pro | Asn | Asn | Asp |
| | | 290 | | | | | 295 | | | | | 300 | | | |
| Lys | Gln | Lys | Tyr | Thr | Leu | Lys | Ile | Asn | His | Asp | Cys | Val | Pro | Glu | Gln |
| 305 | | | | | 310 | | | | | 315 | | | | | 320 |
| Val | Ile | Ala | Glu | Ala | Ile | Arg | Lys | Lys | Thr | Arg | Ser | Met | Leu | Leu | Ser |
| | | | | 325 | | | | | 330 | | | | | 335 | |
| Ser | Glu | Gln | Leu | Lys | Leu | Cys | Val | Leu | Glu | Tyr | Gln | Gly | Lys | Tyr | Ile |
| | | | 340 | | | | | 345 | | | | | 350 | | |
| Leu | Lys | Val | Cys | Gly | Cys | Asp | Glu | Tyr | Phe | Leu | Glu | Lys | Tyr | Pro | Leu |
| | | | 355 | | | | | 360 | | | | | 365 | | |
| Ser | Gln | Tyr | Lys | Tyr | Ile | Arg | Ser | Cys | Ile | Met | Leu | Gly | Arg | Met | Pro |
| | | 370 | | | | | 375 | | | | | 380 | | | |
| Asn | Leu | Met | Leu | Met | Ala | Lys | Glu | Ser | Leu | Tyr | Ser | Gln | Leu | Pro | Met |

```
              385                 390                 395                 400
Asp Cys Phe Thr Met Pro Ser Tyr Ser Arg Arg Ile Ser Thr Ala Thr
                    405                 410                 415
Pro Tyr Met Asn Gly Glu Thr Ser Thr Lys Ser Leu Trp Val Ile Asn
                    420                 425                 430
Ser Ala Leu Arg Ile Lys Ile Leu Cys Ala Thr Tyr Val Asn Val Asn
                    435                 440                 445
Ile Arg Asp Ile Asp Lys Ile Tyr Val Arg Thr Gly Ile Tyr His Gly
                    450                 455                 460
Gly Glu Pro Leu Cys Asp Asn Val Asn Thr Gln Arg Val Pro Cys Ser
465                 470                 475                 480
Asn Pro Arg Trp Asn Glu Trp Leu Asn Tyr Asp Ile Tyr Ile Pro Asp
                    485                 490                 495
Leu Pro Arg Ala Ala Arg Leu Cys Leu Ser Ile Cys Ser Val Lys Gly
                    500                 505                 510
Arg Lys Gly Ala Lys Glu Glu His Cys Pro Leu Ala Trp Gly Asn Ile
                    515                 520                 525
Asn Leu Phe Asp Tyr Thr Asp Thr Leu Val Ser Gly Lys Met Ala Leu
                    530                 535                 540
Asn Leu Trp Pro Val Pro His Gly Leu Glu Asp Leu Leu Asn Pro Ile
545                 550                 555                 560
Gly Val Thr Gly Ser Asn Pro Asn Lys Glu Thr Pro Cys Leu Glu Leu
                    565                 570                 575
Glu Phe Asp Trp Phe Ser Ser Val Val Lys Phe Pro Asp Met Ser Val
                    580                 585                 590
Ile Glu Glu His Ala Asn Trp Ser Val Ser Arg Glu Ala Gly Phe Ser
                    595                 600                 605
Tyr Ser His Ala Gly Leu Ser Asn Arg Leu Ala Arg Asp Asn Glu Leu
                    610                 615                 620
Arg Glu Asn Asp Lys Glu Gln Leu Lys Ala Ile Ser Thr Arg Asp Pro
625                 630                 635                 640
Leu Ser Glu Ile Thr Glu Gln Glu Lys Asp Phe Leu Trp Ser His Arg
                    645                 650                 655
His Tyr Cys Val Thr Ile Pro Glu Ile Leu Pro Lys Leu Leu Leu Ser
                    660                 665                 670
Val Lys Trp Asn Ser Arg Asp Glu Val Ala Gln Met Tyr Cys Leu Val
                    675                 680                 685
Lys Asp Trp Pro Pro Ile Lys Pro Glu Gln Ala Met Glu Leu Leu Asp
                    690                 695                 700
Cys Asn Tyr Pro Asp Pro Met Val Arg Gly Phe Ala Val Arg Cys Leu
705                 710                 715                 720
Glu Lys Tyr Leu Thr Asp Asp Lys Leu Ser Gln Tyr Leu Ile Gln Leu
                    725                 730                 735
Val Gln Val Leu Lys Tyr Glu Gln Tyr Leu Asp Asn Leu Leu Val Arg
                    740                 745                 750
Phe Leu Leu Lys Lys Ala Leu Thr Asn Gln Arg Ile Gly His Phe Phe
                    755                 760                 765
Phe Trp His Leu Lys Ser Glu Met His Asn Lys Thr Val Ser Gln Arg
                    770                 775                 780
Phe Gly Leu Leu Leu Glu Ser Tyr Cys Arg Ala Cys Gly Met Tyr Leu
785                 790                 795                 800
Lys His Leu Asn Arg Gln Val Glu Ala Met Glu Lys Leu Ile Asn Leu
                    805                 810                 815
```

```
Thr Asp Ile Leu Lys Gln Glu Lys Lys Asp Glu Thr Gln Lys Val Gln
            820                 825                 830

Met Lys Phe Leu Val Glu Gln Met Arg Arg Pro Asp Phe Met Asp Ala
            835                 840                 845

Leu Gln Gly Phe Leu Ser Pro Leu Asn Pro Ala His Gln Leu Gly Asn
            850                 855                 860

Leu Arg Leu Glu Glu Cys Arg Ile Met Ser Ser Ala Lys Arg Pro Leu
865                 870                 875                 880

Trp Leu Asn Trp Glu Asn Pro Asp Ile Met Ser Glu Leu Leu Phe Gln
                885                 890                 895

Asn Asn Glu Ile Ile Phe Lys Asn Gly Asp Asp Leu Arg Gln Asp Met
                900                 905                 910

Leu Thr Leu Gln Ile Ile Arg Ile Met Glu Asn Ile Trp Gln Asn Gln
            915                 920                 925

Gly Leu Asp Leu Arg Met Leu Pro Tyr Gly Cys Leu Ser Ile Gly Asp
            930                 935                 940

Cys Val Gly Leu Ile Glu Val Val Arg Asn Ser His Thr Ile Met Gln
945                 950                 955                 960

Ile Gln Cys Lys Gly Gly Leu Lys Gly Ala Leu Gln Phe Asn Ser His
                965                 970                 975

Thr Leu His Gln Trp Leu Lys Asp Lys Asn Lys Gly Glu Ile Tyr Asp
                980                 985                 990

Ala Ala Ile Asp Leu Phe Thr Arg Ser Cys Ala Gly Tyr Cys Val Ala
            995                 1000                1005

Thr Phe Ile Leu Gly Ile Gly Asp Arg His Asn Ser Asn Ile Met
     1010                1015                1020

Val Lys Asp Asp Gly Gln Leu Phe His Ile Asp Phe Gly His Phe
     1025                1030                1035

Leu Asp His Lys Lys Lys Lys Phe Gly Tyr Lys Arg Glu Arg Val
     1040                1045                1050

Pro Phe Val Leu Thr Gln Asp Phe Leu Ile Val Ile Ser Lys Gly
     1055                1060                1065

Ala Gln Glu Cys Thr Lys Thr Arg Glu Phe Glu Arg Phe Gln Glu
     1070                1075                1080

Met Cys Tyr Lys Ala Tyr Leu Ala Ile Arg Gln His Ala Asn Leu
     1085                1090                1095

Phe Ile Asn Leu Phe Ser Met Met Leu Gly Ser Gly Met Pro Glu
     1100                1105                1110

Leu Gln Ser Phe Asp Asp Ile Ala Tyr Ile Arg Lys Thr Leu Ala
     1115                1120                1125

Leu Asp Lys Thr Glu Gln Glu Ala Leu Glu Tyr Phe Met Lys Gln
     1130                1135                1140

Met Asn Asp Ala His His Gly Gly Trp Thr Thr Lys Met Asp Trp
     1145                1150                1155

Ile Phe His Thr Ile Lys Gln His Ala Leu Asn Glu Leu Gly Gly
     1160                1165                1170

Ala His His His His His His
     1175                1180

<210> SEQ ID NO 5
<211> LENGTH: 28
<212> TYPE: DNA
<213> ORGANISM: Artificial
<220> FEATURE:
<223> OTHER INFORMATION: PCR primer
```

```
<400> SEQUENCE: 5
cgagaatatg atagattata tgaagaat                                        28

<210> SEQ ID NO 6
<211> LENGTH: 30
<212> TYPE: DNA
<213> ORGANISM: Artificial
<220> FEATURE:
<223> OTHER INFORMATION: PCR primer

<400> SEQUENCE: 6
tggtttaatg ctgttcatac gtttgtcaat                                      30

<210> SEQ ID NO 7
<211> LENGTH: 76
<212> TYPE: DNA
<213> ORGANISM: Artificial
<220> FEATURE:
<223> OTHER INFORMATION: PCR primer

<400> SEQUENCE: 7
gggacaagtt tgtacaaaaa agcaggctac gaaggagata tacatatgcg agaatatgat     60
agattatatg aagaat                                                     76

<210> SEQ ID NO 8
<211> LENGTH: 54
<212> TYPE: DNA
<213> ORGANISM: Artificial
<220> FEATURE:
<223> OTHER INFORMATION: PCR primer

<400> SEQUENCE: 8
actgaagcat cctcctcctc ctcctcctgg tttaatgctg ttcatacgtt tgtc           54

<210> SEQ ID NO 9
<211> LENGTH: 54
<212> TYPE: DNA
<213> ORGANISM: Artificial
<220> FEATURE:
<223> OTHER INFORMATION: PCR primer

<400> SEQUENCE: 9
attaaaccag gaggaggagg aggaggatgc ttcagtttca taatgcctcc tgct           54

<210> SEQ ID NO 10
<211> LENGTH: 57
<212> TYPE: DNA
<213> ORGANISM: Artificial
<220> FEATURE:
<223> OTHER INFORMATION: PCR primer

<400> SEQUENCE: 10
agctccgtga tggtgatggt gatgtgctcc agatctgtag tctttccgaa ctgtgtg        57

<210> SEQ ID NO 11
<211> LENGTH: 61
<212> TYPE: DNA
<213> ORGANISM: Artificial
<220> FEATURE:
<223> OTHER INFORMATION: PCR primer

<400> SEQUENCE: 11
gggaccactt tgtacaagaa agctgggttt aagctccgtg atggtgatgg tgatgtgctc     60
c                                                                     61
```

```
<210> SEQ ID NO 12
<211> LENGTH: 1194
<212> TYPE: PRT
<213> ORGANISM: Artificial
<220> FEATURE:
<223> OTHER INFORMATION: PI3K kinase construct

<400> SEQUENCE: 12
```

| | | | | | | | | | | | | | | |
|---|---|---|---|---|---|---|---|---|---|---|---|---|---|---|
| Met | Arg | Glu | Tyr | Asp | Arg | Leu | Tyr | Glu | Tyr | Thr | Arg | Thr | Ser | Gln |
| 1 | | | | 5 | | | | | 10 | | | | | 15 |
| Glu | Ile | Gln | Met | Lys | Arg | Thr | Ala | Ile | Glu | Ala | Phe | Asn | Glu | Thr | Ile |
| | | | | 20 | | | | | 25 | | | | | 30 | |
| Lys | Ile | Phe | Glu | Glu | Gln | Cys | Gln | Thr | Gln | Glu | Arg | Tyr | Ser | Lys | Glu |
| | | | 35 | | | | | 40 | | | | | 45 | | |
| Tyr | Ile | Glu | Lys | Phe | Lys | Arg | Glu | Gly | Lys | Glu | Lys | Glu | Ile | Gln | Arg |
| | 50 | | | | | 55 | | | | | 60 | | | | |
| Ile | Met | His | Asn | Tyr | Asp | Lys | Leu | Lys | Ser | Arg | Ile | Ser | Glu | Ile | Ile |
| 65 | | | | | 70 | | | | | 75 | | | | | 80 |
| Asp | Ser | Arg | Arg | Arg | Leu | Glu | Glu | Asp | Leu | Lys | Lys | Gln | Ala | Ala | Glu |
| | | | | 85 | | | | | 90 | | | | | 95 | |
| Tyr | Arg | Glu | Ile | Asp | Lys | Arg | Met | Asn | Ser | Ile | Lys | Pro | Gly | Gly | Gly |
| | | | 100 | | | | | 105 | | | | | 110 | | |
| Gly | Gly | Gly | Cys | Phe | Ser | Phe | Ile | Met | Pro | Pro | Ala | Met | Ala | Asp | Ile |
| | | | 115 | | | | | 120 | | | | | 125 | | |
| Leu | Asp | Ile | Trp | Ala | Val | Asp | Ser | Gln | Ile | Ala | Ser | Asp | Gly | Ser | Ile |
| 130 | | | | | 135 | | | | | 140 | | | | | |
| Pro | Val | Asp | Phe | Leu | Leu | Pro | Thr | Gly | Ile | Tyr | Ile | Gln | Leu | Glu | Val |
| 145 | | | | | 150 | | | | | 155 | | | | | 160 |
| Pro | Arg | Glu | Ala | Thr | Ile | Ser | Tyr | Ile | Lys | Gln | Met | Leu | Trp | Lys | Gln |
| | | | | 165 | | | | | 170 | | | | | 175 | |
| Val | His | Asn | Tyr | Pro | Met | Phe | Asn | Leu | Leu | Met | Asp | Ile | Asp | Ser | Tyr |
| | | | 180 | | | | | 185 | | | | | 190 | | |
| Met | Phe | Ala | Cys | Val | Asn | Gln | Thr | Ala | Val | Tyr | Glu | Glu | Leu | Glu | Asp |
| | | | 195 | | | | | 200 | | | | | 205 | | |
| Glu | Thr | Arg | Arg | Leu | Cys | Asp | Val | Arg | Pro | Phe | Leu | Pro | Val | Leu | Lys |
| | 210 | | | | | 215 | | | | | 220 | | | | |
| Leu | Val | Thr | Arg | Ser | Cys | Asp | Pro | Gly | Glu | Lys | Leu | Asp | Ser | Lys | Ile |
| 225 | | | | | 230 | | | | | 235 | | | | | 240 |
| Gly | Val | Leu | Ile | Gly | Lys | Gly | Leu | His | Glu | Phe | Asp | Ser | Leu | Lys | Asp |
| | | | | 245 | | | | | 250 | | | | | 255 | |
| Pro | Glu | Val | Asn | Glu | Phe | Arg | Arg | Lys | Met | Arg | Lys | Phe | Ser | Glu | Glu |
| | | | 260 | | | | | 265 | | | | | 270 | | |
| Lys | Ile | Leu | Ser | Leu | Val | Gly | Leu | Ser | Trp | Met | Asp | Trp | Leu | Lys | Gln |
| | | | 275 | | | | | 280 | | | | | 285 | | |
| Thr | Tyr | Pro | Pro | Glu | His | Glu | Pro | Ser | Ile | Pro | Glu | Asn | Leu | Glu | Asp |
| | 290 | | | | | 295 | | | | | 300 | | | | |
| Lys | Leu | Tyr | Gly | Gly | Lys | Leu | Ile | Val | Ala | Val | His | Phe | Glu | Asn | Cys |
| 305 | | | | | 310 | | | | | 315 | | | | | 320 |
| Gln | Asp | Val | Phe | Ser | Phe | Gln | Val | Ser | Pro | Asn | Met | Asn | Pro | Ile | Lys |
| | | | | 325 | | | | | 330 | | | | | 335 | |
| Val | Asn | Glu | Leu | Ala | Ile | Gln | Lys | Arg | Leu | Thr | Ile | His | Gly | Lys | Glu |
| | | | 340 | | | | | 345 | | | | | 350 | | |
| Asp | Glu | Val | Ser | Pro | Tyr | Asp | Tyr | Val | Leu | Gln | Val | Ser | Gly | Arg | Val |
| | | | 355 | | | | | 360 | | | | | 365 | | |
| Glu | Tyr | Val | Phe | Gly | Asp | His | Pro | Leu | Ile | Gln | Phe | Gln | Tyr | Ile | Arg |

-continued

```
            370                 375                 380
Asn Cys Val Met Asn Arg Ala Leu Pro His Phe Ile Leu Val Glu Cys
385                 390                 395                 400

Cys Lys Ile Lys Lys Met Tyr Glu Gln Glu Met Ile Ala Ile Glu Ala
                    405                 410                 415

Ala Ile Asn Arg Asn Ser Ser Asn Leu Pro Leu Pro Leu Pro Pro Lys
                420                 425                 430

Lys Thr Arg Ile Ile Ser His Val Trp Glu Asn Asn Pro Phe Gln
                435                 440                 445

Ile Val Leu Val Lys Gly Asn Lys Leu Asn Thr Glu Glu Thr Val Lys
                450                 455                 460

Val His Val Arg Ala Gly Leu Phe His Gly Thr Glu Leu Leu Cys Lys
465                 470                 475                 480

Thr Ile Val Ser Ser Glu Val Ser Gly Lys Asn Asp His Ile Trp Asn
                    485                 490                 495

Glu Pro Leu Glu Phe Asp Ile Asn Ile Cys Asp Leu Pro Arg Met Ala
                500                 505                 510

Arg Leu Cys Phe Ala Val Tyr Ala Val Leu Asp Lys Val Lys Thr Lys
                515                 520                 525

Lys Ser Thr Lys Thr Ile Asn Pro Ser Lys Tyr Gln Thr Ile Arg Lys
                530                 535                 540

Ala Gly Lys Val His Tyr Pro Val Ala Trp Val Asn Thr Met Val Phe
545                 550                 555                 560

Asp Phe Lys Gly Gln Leu Arg Thr Gly Asp Ile Ile Leu His Ser Trp
                    565                 570                 575

Ser Ser Phe Pro Asp Glu Leu Glu Met Leu Asn Pro Met Gly Thr
                580                 585                 590

Val Gln Thr Asn Pro Tyr Thr Glu Asn Ala Thr Ala Leu His Val Lys
                595                 600                 605

Phe Pro Glu Asn Lys Lys Gln Pro Tyr Tyr Pro Pro Phe Asp Lys
                610                 615                 620

Ile Ile Glu Lys Ala Ala Glu Ile Ala Ser Ser Asp Ser Ala Asn Val
625                 630                 635                 640

Ser Ser Arg Gly Gly Lys Lys Phe Leu Pro Val Leu Lys Glu Ile Leu
                    645                 650                 655

Asp Arg Asp Pro Leu Ser Gln Leu Cys Glu Asn Glu Met Asp Leu Ile
                660                 665                 670

Trp Thr Leu Arg Gln Asp Cys Arg Glu Ile Phe Pro Gln Ser Leu Pro
                675                 680                 685

Lys Leu Leu Leu Ser Ile Lys Trp Asn Lys Leu Glu Asp Val Ala Gln
                690                 695                 700

Leu Gln Ala Leu Leu Gln Ile Trp Pro Lys Leu Pro Pro Arg Glu Ala
705                 710                 715                 720

Leu Glu Leu Leu Asp Phe Asn Tyr Pro Asp Gln Tyr Val Arg Glu Tyr
                    725                 730                 735

Ala Val Gly Cys Leu Arg Gln Met Ser Asp Glu Glu Leu Ser Gln Tyr
                740                 745                 750

Leu Leu Gln Leu Val Gln Val Leu Lys Tyr Glu Pro Phe Leu Asp Cys
                755                 760                 765

Ala Leu Ser Arg Phe Leu Leu Glu Arg Ala Leu Gly Asn Arg Arg Ile
                770                 775                 780

Gly Gln Phe Leu Phe Trp His Leu Arg Ser Glu Val His Ile Pro Ala
785                 790                 795                 800
```

```
Val Ser Val Gln Phe Gly Val Ile Leu Glu Ala Tyr Cys Arg Gly Ser
            805                 810                 815

Val Gly His Met Lys Val Leu Ser Lys Gln Val Glu Ala Leu Asn Lys
            820                 825                 830

Leu Lys Thr Leu Asn Ser Leu Ile Lys Leu Asn Ala Val Lys Leu Asn
            835                 840                 845

Arg Ala Lys Gly Lys Glu Ala Met His Thr Cys Leu Lys Gln Ser Ala
            850                 855                 860

Tyr Arg Glu Ala Leu Ser Asp Leu Gln Ser Pro Leu Asn Pro Cys Val
865                 870                 875                 880

Ile Leu Ser Glu Leu Tyr Val Glu Lys Cys Lys Tyr Met Asp Ser Lys
            885                 890                 895

Met Lys Pro Leu Trp Leu Val Tyr Asn Asn Lys Val Phe Gly Glu Asp
            900                 905                 910

Ser Val Gly Val Ile Phe Lys Asn Gly Asp Asp Leu Arg Gln Asp Met
            915                 920                 925

Leu Thr Leu Gln Met Leu Arg Leu Met Asp Leu Leu Trp Lys Glu Ala
            930                 935                 940

Gly Leu Asp Leu Arg Met Leu Pro Tyr Gly Cys Leu Ala Thr Gly Asp
945                 950                 955                 960

Arg Ser Gly Leu Ile Glu Val Val Ser Thr Ser Glu Thr Ile Ala Asp
            965                 970                 975

Ile Gln Leu Asn Ser Ser Asn Val Ala Ala Ala Ala Phe Asn Lys
            980                 985                 990

Asp Ala Leu Leu Asn Trp Leu Lys Glu Tyr Asn Ser Gly Asp Asp Leu
            995                 1000                1005

Asp Arg Ala Ile Glu Glu Phe Thr Leu Ser Cys Ala Gly Tyr Cys
            1010                1015                1020

Val Ala Ser Tyr Val Leu Gly Ile Gly Asp Arg His Ser Asp Asn
            1025                1030                1035

Ile Met Val Lys Lys Thr Gly Gln Leu Phe His Ile Asp Phe Gly
            1040                1045                1050

His Ile Leu Gly Asn Phe Lys Ser Lys Phe Gly Ile Lys Arg Glu
            1055                1060                1065

Arg Val Pro Phe Ile Leu Thr Tyr Asp Phe Ile His Val Ile Gln
            1070                1075                1080

Gln Gly Lys Thr Gly Asn Thr Glu Lys Phe Gly Arg Phe Arg Gln
            1085                1090                1095

Cys Cys Glu Asp Ala Tyr Leu Ile Leu Arg Arg His Gly Asn Leu
            1100                1105                1110

Phe Ile Thr Leu Phe Ala Leu Met Leu Thr Ala Gly Leu Pro Glu
            1115                1120                1125

Leu Thr Ser Val Lys Asp Ile Gln Tyr Leu Lys Asp Ser Leu Ala
            1130                1135                1140

Leu Gly Lys Ser Glu Glu Ala Leu Lys Gln Phe Lys Gln Lys
            1145                1150                1155

Phe Asp Glu Ala Leu Arg Glu Ser Trp Thr Thr Lys Val Asn Trp
            1160                1165                1170

Met Ala His Thr Val Arg Lys Asp Tyr Arg Ser Gly Ala His His
            1175                1180                1185

His His His His Gly Ala
            1190

<210> SEQ ID NO 13
```

<211> LENGTH: 966
<212> TYPE: PRT
<213> ORGANISM: Artificial
<220> FEATURE:
<223> OTHER INFORMATION: PI3K kinase construct

<400> SEQUENCE: 13

```
Met Ser Glu Glu Ser Gln Ala Phe Gln Arg Gln Leu Thr Ala Leu Ile
1               5                   10                  15

Gly Tyr Asp Val Thr Asp Val Ser Asn Val His Asp Asp Glu Leu Glu
            20                  25                  30

Phe Thr Arg Arg Gly Leu Val Thr Pro Arg Met Ala Glu Val Ala Ser
        35                  40                  45

Arg Asp Pro Lys Leu Tyr Ala Met His Pro Trp Val Thr Ser Lys Pro
    50                  55                  60

Leu Pro Glu Tyr Leu Trp Lys Lys Ile Ala Asn Asn Cys Ile Phe Ile
65                  70                  75                  80

Val Ile His Arg Ser Thr Thr Ser Gln Thr Ile Lys Val Ser Pro Asp
                85                  90                  95

Asp Thr Pro Gly Ala Ile Leu Gln Ser Phe Phe Thr Lys Met Ala Lys
            100                 105                 110

Lys Lys Ser Leu Met Asp Ile Pro Glu Ser Gln Ser Glu Gln Asp Phe
        115                 120                 125

Val Leu Arg Val Cys Gly Arg Asp Glu Tyr Leu Val Gly Glu Thr Pro
    130                 135                 140

Ile Lys Asn Phe Gln Trp Val Arg His Cys Leu Lys Asn Gly Glu Glu
145                 150                 155                 160

Ile His Val Val Leu Asp Thr Pro Pro Asp Pro Ala Leu Asp Glu Val
                165                 170                 175

Arg Lys Glu Glu Trp Pro Leu Val Asp Asp Cys Thr Gly Val Thr Gly
            180                 185                 190

Tyr His Glu Gln Leu Thr Ile His Gly Lys Asp His Glu Ser Val Phe
        195                 200                 205

Thr Val Ser Leu Trp Asp Cys Asp Arg Lys Phe Arg Val Lys Ile Arg
    210                 215                 220

Gly Ile Asp Ile Pro Val Leu Pro Arg Asn Thr Asp Leu Thr Val Phe
225                 230                 235                 240

Val Glu Ala Asn Ile Gln His Gly Gln Gln Val Leu Cys Gln Arg Arg
                245                 250                 255

Thr Ser Pro Lys Pro Phe Thr Glu Val Leu Trp Asn Val Trp Leu
            260                 265                 270

Glu Phe Ser Ile Lys Ile Lys Asp Leu Pro Lys Gly Ala Leu Leu Asn
        275                 280                 285

Leu Gln Ile Tyr Cys Gly Lys Ala Pro Ala Leu Ser Ser Lys Ala Ser
    290                 295                 300

Ala Glu Ser Pro Ser Ser Glu Ser Lys Gly Lys Val Arg Leu Leu Tyr
305                 310                 315                 320

Tyr Val Asn Leu Leu Leu Ile Asp His Arg Phe Leu Leu Arg Arg Gly
                325                 330                 335

Glu Tyr Val Leu His Met Trp Gln Ile Ser Gly Lys Gly Glu Asp Gln
            340                 345                 350

Gly Ser Phe Asn Ala Asp Lys Leu Thr Ser Ala Thr Asn Pro Asp Lys
        355                 360                 365

Glu Asn Ser Met Ser Ile Ser Ile Leu Leu Asp Asn Tyr Cys His Pro
    370                 375                 380
```

```
Ile Ala Leu Pro Lys His Gln Pro Thr Pro Asp Pro Glu Gly Asp Arg
385                 390                 395                 400

Val Arg Ala Glu Met Pro Asn Gln Leu Arg Lys Gln Leu Glu Ala Ile
                405                 410                 415

Ile Ala Thr Asp Pro Leu Asn Pro Leu Thr Ala Glu Asp Lys Glu Leu
            420                 425                 430

Leu Trp His Phe Arg Tyr Glu Ser Leu Lys His Pro Lys Ala Tyr Pro
        435                 440                 445

Lys Leu Phe Ser Ser Val Lys Trp Gly Gln Gln Glu Ile Val Ala Lys
    450                 455                 460

Thr Tyr Gln Leu Leu Ala Arg Arg Glu Val Trp Asp Gln Ser Ala Leu
465                 470                 475                 480

Asp Val Gly Leu Thr Met Gln Leu Leu Asp Cys Asn Phe Ser Asp Glu
                485                 490                 495

Asn Val Arg Ala Ile Ala Val Gln Lys Leu Glu Ser Leu Glu Asp Asp
            500                 505                 510

Asp Val Leu His Tyr Leu Leu Gln Leu Val Gln Ala Val Lys Phe Glu
        515                 520                 525

Pro Tyr His Asp Ser Ala Leu Ala Arg Phe Leu Leu Lys Arg Gly Leu
    530                 535                 540

Arg Asn Lys Arg Ile Gly His Phe Leu Phe Trp Phe Leu Arg Ser Glu
545                 550                 555                 560

Ile Ala Gln Ser Arg His Tyr Gln Gln Arg Phe Ala Val Ile Leu Glu
                565                 570                 575

Ala Tyr Leu Arg Gly Cys Gly Thr Ala Met Leu His Asp Phe Thr Gln
            580                 585                 590

Gln Val Gln Val Ile Glu Met Leu Gln Lys Val Thr Leu Asp Ile Lys
        595                 600                 605

Ser Leu Ser Ala Glu Lys Tyr Asp Val Ser Ser Gln Val Ile Ser Gln
    610                 615                 620

Leu Lys Gln Lys Leu Glu Asn Leu Gln Asn Ser Gln Leu Pro Glu Ser
625                 630                 635                 640

Phe Arg Val Pro Tyr Asp Pro Gly Leu Lys Ala Gly Ala Leu Ala Ile
                645                 650                 655

Glu Lys Cys Lys Val Met Ala Ser Lys Lys Lys Pro Leu Trp Leu Glu
            660                 665                 670

Phe Lys Cys Ala Asp Pro Thr Ala Leu Ser Asn Glu Thr Ile Gly Ile
        675                 680                 685

Ile Phe Lys His Gly Asp Asp Leu Arg Gln Asp Met Leu Ile Leu Gln
    690                 695                 700

Ile Leu Arg Ile Met Glu Ser Ile Trp Glu Thr Glu Ser Leu Asp Leu
705                 710                 715                 720

Cys Leu Leu Pro Tyr Gly Cys Ile Ser Thr Gly Asp Lys Ile Gly Met
                725                 730                 735

Ile Glu Ile Val Lys Asp Ala Thr Thr Ile Ala Lys Ile Gln Gln Ser
            740                 745                 750

Thr Val Gly Asn Thr Gly Ala Phe Lys Asp Glu Val Leu Asn His Trp
        755                 760                 765

Leu Lys Glu Lys Ser Pro Thr Glu Glu Lys Phe Gln Ala Ala Val Glu
    770                 775                 780

Arg Phe Val Tyr Ser Cys Ala Gly Tyr Cys Val Ala Thr Phe Val Leu
785                 790                 795                 800

Gly Ile Gly Asp Arg His Asn Asp Asn Ile Met Ile Thr Glu Thr Gly
                805                 810                 815
```

Asn Leu Phe His Ile Asp Phe Gly His Ile Leu Gly Asn Tyr Lys Ser
            820                 825                 830

Phe Leu Gly Ile Asn Lys Glu Arg Val Pro Phe Val Leu Thr Pro Asp
            835                 840                 845

Phe Leu Phe Val Met Gly Thr Ser Gly Lys Lys Thr Ser Pro His Phe
        850                 855                 860

Gln Lys Phe Gln Asp Ile Cys Val Lys Ala Tyr Leu Ala Leu Arg His
865                 870                 875                 880

His Thr Asn Leu Leu Ile Ile Leu Phe Ser Met Met Leu Met Thr Gly
                885                 890                 895

Met Pro Gln Leu Thr Ser Lys Glu Asp Ile Glu Tyr Ile Arg Asp Ala
            900                 905                 910

Leu Thr Val Gly Lys Asn Glu Gly Asp Ala Lys Lys Tyr Phe Leu Asp
            915                 920                 925

Gln Ile Glu Val Cys Arg Asp Lys Gly Trp Thr Val Gln Phe Asn Trp
930                 935                 940

Phe Leu His Leu Val Leu Gly Ile Lys Gln Gly Glu Lys His Ser Ala
945                 950                 955                 960

His His His His His His
            965

<210> SEQ ID NO 14
<211> LENGTH: 45
<212> TYPE: DNA
<213> ORGANISM: Artificial
<220> FEATURE:
<223> OTHER INFORMATION: PCR primer

<400> SEQUENCE: 14
tcctcctcct cctcctcctg gtttaatgct gttcatacgt ttgtc                45

<210> SEQ ID NO 15
<211> LENGTH: 26
<212> TYPE: DNA
<213> ORGANISM: Artificial
<220> FEATURE:
<223> OTHER INFORMATION: PCR primer

<400> SEQUENCE: 15
atgccccctg gggtggactg ccccat                26

<210> SEQ ID NO 16
<211> LENGTH: 26
<212> TYPE: DNA
<213> ORGANISM: Artificial
<220> FEATURE:
<223> OTHER INFORMATION: PCR primer

<400> SEQUENCE: 16
ctactgcctg ttgtctttgg acacgt                26

<210> SEQ ID NO 17
<211> LENGTH: 53
<212> TYPE: DNA
<213> ORGANISM: Artificial
<220> FEATURE:
<223> OTHER INFORMATION: PCR primer

<400> SEQUENCE: 17
attaaaccag gaggaggagg aggaggaccc cctggggtgg actgccccat gga                53

-continued

<210> SEQ ID NO 18
<211> LENGTH: 56
<212> TYPE: DNA
<213> ORGANISM: Artificial
<220> FEATURE:
<223> OTHER INFORMATION: PCR primer

<400> SEQUENCE: 18
agctccgtga tggtgatggt gatgtgctcc ctgcctgttg tctttggaca cgttgt    56

<210> SEQ ID NO 19
<211> LENGTH: 60
<212> TYPE: DNA
<213> ORGANISM: Artificial
<220> FEATURE:
<223> OTHER INFORMATION: PCR primer

<400> SEQUENCE: 19
gggaccactt tgtacaagaa agctgggttt aagctccgtg atggtgatgg tgagtgctcc    60

<210> SEQ ID NO 20
<211> LENGTH: 1169
<212> TYPE: PRT
<213> ORGANISM: Artificial
<220> FEATURE:
<223> OTHER INFORMATION: PI3K kinase construct

<400> SEQUENCE: 20

Met Arg Glu Tyr Asp Arg Leu Tyr Glu Glu Tyr Thr Arg Thr Ser Gln
1               5                   10                  15

Glu Ile Gln Met Lys Arg Thr Ala Ile Glu Ala Phe Asn Glu Thr Ile
            20                  25                  30

Lys Ile Phe Glu Glu Gln Cys Gln Thr Gln Glu Arg Tyr Ser Lys Glu
        35                  40                  45

Tyr Ile Glu Lys Phe Lys Arg Glu Gly Asn Glu Lys Glu Ile Gln Arg
    50                  55                  60

Ile Met His Asn Tyr Asp Lys Leu Lys Ser Arg Ile Ser Glu Ile Ile
65                  70                  75                  80

Asp Ser Arg Arg Arg Leu Glu Glu Asp Leu Lys Lys Gln Ala Ala Glu
                85                  90                  95

Tyr Arg Glu Ile Asp Lys Arg Met Asn Ser Ile Lys Pro Gly Gly Gly
            100                 105                 110

Gly Gly Gly Pro Pro Gly Val Asp Cys Pro Met Glu Phe Trp Thr Lys
        115                 120                 125

Glu Glu Asn Gln Ser Val Val Val Asp Phe Leu Leu Pro Thr Gly Val
    130                 135                 140

Tyr Leu Asn Phe Pro Val Ser Arg Asn Ala Asn Leu Ser Thr Ile Lys
145                 150                 155                 160

Gln Leu Leu Trp His Arg Ala Gln Tyr Glu Pro Leu Phe His Met Leu
                165                 170                 175

Ser Gly Pro Glu Ala Tyr Val Phe Thr Cys Ile Asn Gln Thr Ala Glu
            180                 185                 190

Gln Gln Glu Leu Glu Asp Glu Gln Arg Arg Leu Cys Asp Val Gln Pro
        195                 200                 205

Phe Leu Pro Val Leu Arg Leu Val Ala Arg Glu Gly Asp Arg Val Lys
    210                 215                 220

Lys Leu Ile Asn Ser Gln Ile Ser Leu Leu Ile Gly Lys Gly Leu His
225                 230                 235                 240

Glu Phe Asp Ser Leu Cys Asp Pro Glu Val Asn Asp Phe Arg Ala Lys
                245                 250                 255

```
Met Cys Gln Phe Cys Glu Glu Ala Ala Arg Arg Gln Gln Leu Gly
        260                 265                 270

Trp Glu Ala Trp Leu Gln Tyr Ser Phe Pro Leu Gln Leu Glu Pro Ser
        275                 280                 285

Ala Gln Thr Trp Gly Pro Gly Thr Leu Arg Leu Pro Asn Arg Ala Leu
        290                 295                 300

Leu Val Asn Val Lys Phe Glu Gly Ser Glu Ser Phe Thr Phe Gln
305                 310                 315                 320

Val Ser Thr Lys Asp Val Pro Leu Ala Leu Met Ala Cys Ala Leu Arg
                325                 330                 335

Lys Lys Ala Thr Val Phe Arg Gln Pro Leu Val Glu Gln Pro Glu Asp
                340                 345                 350

Tyr Thr Leu Gln Val Asn Gly Arg His Glu Tyr Leu Tyr Gly Ser Tyr
                355                 360                 365

Pro Leu Cys Gln Phe Gln Tyr Ile Cys Ser Cys Leu His Ser Gly Leu
        370                 375                 380

Thr Pro His Leu Thr Met Val His Ser Ser Ile Leu Ala Met Arg
385                 390                 395                 400

Asp Glu Gln Ser Asn Pro Ala Pro Gln Val Gln Lys Pro Arg Ala Lys
                405                 410                 415

Pro Pro Pro Ile Pro Ala Lys Lys Pro Ser Ser Val Ser Leu Trp Ser
                420                 425                 430

Leu Glu Gln Pro Phe Arg Ile Glu Leu Ile Gln Gly Ser Lys Val Asn
        435                 440                 445

Ala Asp Glu Arg Met Lys Leu Val Val Gln Ala Gly Leu Phe His Gly
        450                 455                 460

Asn Glu Met Leu Cys Lys Thr Val Ser Ser Glu Val Ser Val Cys
465                 470                 475                 480

Ser Glu Pro Val Trp Lys Gln Arg Leu Glu Phe Asp Ile Asn Ile Cys
                485                 490                 495

Asp Leu Pro Arg Met Ala Arg Leu Cys Phe Ala Leu Tyr Ala Val Ile
                500                 505                 510

Glu Lys Ala Lys Lys Ala Arg Ser Thr Lys Lys Lys Ser Lys Lys Ala
        515                 520                 525

Asp Cys Pro Ile Ala Trp Ala Asn Leu Met Leu Phe Asp Tyr Lys Asp
        530                 535                 540

Gln Leu Lys Thr Gly Glu Arg Cys Leu Tyr Met Trp Pro Ser Val Pro
545                 550                 555                 560

Asp Glu Lys Gly Glu Leu Leu Asn Pro Thr Gly Thr Val Arg Ser Asn
                565                 570                 575

Pro Asn Thr Asp Ser Ala Ala Leu Leu Ile Cys Leu Pro Glu Val
                580                 585                 590

Ala Pro His Pro Val Tyr Tyr Pro Ala Leu Glu Lys Ile Leu Glu Leu
                595                 600                 605

Gly Arg His Ser Glu Cys Val His Val Thr Glu Glu Gln Leu Gln
        610                 615                 620

Leu Arg Glu Ile Leu Glu Arg Arg Gly Ser Gly Glu Leu Tyr Glu His
625                 630                 635                 640

Glu Lys Asp Leu Val Trp Lys Leu Arg His Glu Val Gln Glu His Phe
                645                 650                 655

Pro Glu Ala Leu Ala Arg Leu Leu Val Thr Lys Trp Asn Lys His
                660                 665                 670

Glu Asp Val Ala Gln Met Leu Tyr Leu Leu Cys Ser Trp Pro Glu Leu
```

-continued

```
            675                 680                 685
Pro Val Leu Ser Ala Leu Glu Leu Leu Asp Phe Ser Phe Pro Asp Cys
    690                 695                 700
His Val Gly Ser Phe Ala Ile Lys Ser Leu Arg Lys Leu Thr Asp Asp
705                 710                 715                 720
Glu Leu Phe Gln Tyr Leu Leu Gln Leu Val Gln Val Leu Lys Tyr Glu
                725                 730                 735
Ser Tyr Leu Asp Cys Glu Leu Thr Lys Phe Leu Leu Asp Arg Ala Leu
            740                 745                 750
Ala Asn Arg Lys Ile Gly His Phe Leu Phe Trp His Leu Arg Ser Glu
        755                 760                 765
Met His Val Pro Ser Val Ala Leu Arg Phe Gly Leu Ile Leu Glu Ala
    770                 775                 780
Tyr Cys Arg Gly Ser Thr His His Met Lys Val Leu Met Lys Gln Gly
785                 790                 795                 800
Glu Ala Leu Ser Lys Leu Lys Ala Leu Asn Asp Phe Val Lys Leu Ser
                805                 810                 815
Ser Gln Lys Thr Pro Lys Pro Gln Thr Lys Glu Leu Met His Leu Cys
            820                 825                 830
Met Arg Gln Glu Ala Tyr Leu Glu Ala Leu Ser His Leu Gln Ser Pro
        835                 840                 845
Leu Asp Pro Ser Thr Leu Leu Ala Glu Val Cys Val Glu Gln Cys Thr
    850                 855                 860
Phe Met Asp Ser Lys Met Lys Pro Leu Trp Ile Met Tyr Ser Asn Glu
865                 870                 875                 880
Glu Ala Gly Ser Gly Gly Ser Val Gly Ile Ile Phe Lys Asn Gly Asp
                885                 890                 895
Asp Leu Arg Gln Asp Met Leu Thr Leu Gln Met Ile Gln Leu Met Asp
            900                 905                 910
Val Leu Trp Lys Gln Gly Leu Asp Leu Arg Met Thr Pro Tyr Gly
        915                 920                 925
Cys Leu Pro Thr Gly Asp Arg Thr Gly Leu Ile Glu Val Val Leu Arg
    930                 935                 940
Ser Asp Thr Ile Ala Asn Ile Gln Leu Asn Lys Ser Asn Met Ala Ala
945                 950                 955                 960
Thr Ala Ala Phe Asn Lys Asp Ala Leu Leu Asn Trp Leu Lys Ser Lys
                965                 970                 975
Asn Pro Gly Glu Ala Leu Asp Arg Ala Ile Glu Glu Phe Thr Leu Ser
            980                 985                 990
Cys Ala Gly Tyr Cys Val Ala Thr  Tyr Val Leu Gly Ile  Gly Asp Arg
        995                 1000                1005
His Ser  Asp Asn Ile Met  Ile Arg Glu Ser Gly Gln  Leu Phe His
    1010                1015                1020
Ile Asp  Phe Gly His Phe  Leu Gly Asn Phe Lys Thr  Lys Phe Gly
    1025                1030                1035
Ile Asn  Arg Glu Arg Val Pro  Phe Ile Leu Thr Tyr  Asp Phe Val
    1040                1045                1050
His Val  Ile Gln Gln Gly Lys  Thr Asn Asn Ser Glu  Lys Phe Glu
    1055                1060                1065
Arg Phe  Arg Gly Tyr Cys Glu  Arg Ala Tyr Thr Ile  Leu Arg Arg
    1070                1075                1080
His Gly  Leu Leu Phe Leu His  Leu Phe Ala Leu Met  Arg Ala Ala
    1085                1090                1095
```

```
Gly Leu Pro Glu Leu Ser Cys Ser Lys Asp Ile Gln Tyr Leu Lys
    1100            1105            1110

Asp Ser Leu Ala Leu Gly Lys Thr Glu Glu Glu Ala Leu Lys His
    1115            1120            1125

Phe Arg Val Lys Phe Asn Glu Ala Leu Arg Glu Ser Trp Lys Thr
    1130            1135            1140

Lys Val Asn Trp Leu Ala His Asn Val Ser Lys Asp Asn Arg Gln
    1145            1150            1155

Glu Leu Gly Gly Ala His His His His His His
    1160            1165
```

2-CARBOXAMIDE CYCLOAMINO UREAS

This application claims priority to U.S. Provisional Application Ser. No. 61/270,028 filed 2 Jul. 2009, the contents of which are incorporated herein by reference in their entirety.

The present invention relates to substituted 2-carboxamide cycloamino ureas, as new phosphatidylinositol (PI) 3-kinase inhibitor compounds, their pharmaceutically acceptable salts, prodrugs thereof and processes for their production. This invention also relates to compositions of these compounds, either alone or in combination with at least one additional therapeutic agent, and optionally in combination with a pharmaceutically acceptable carrier. This invention still further relates to methods of use of these compounds, either alone or in combination with at least one additional therapeutic agent, in the prophylaxis or treatment of a number of diseases, in particular, those mediated by one or more of abnormal activity of growth factors, receptor tyrosine kinases, protein serine/heroine kinases, G protein coupled receptors and phospholipid kinases and phosphatases.

Phosphatidylinositol 3-kinases (PI3Ks) comprise a family of lipid kinases that catalyze the transfer of phosphate to the D-3' position of inositol lipids to produce phosphoinositol-3-phosphate (PIP), phosphoinositol-3,4-diphosphate ($PIP_2$) and phosphoinositol-3,4,5-triphosphate ($PIP_3$) that, in turn, act as second messengers in signaling cascades by docking proteins containing pleckstrin-homology, FYVE, Phox and other phospholipid-binding domains into a variety of signaling complexes often at the plasma membrane ((Vanhaesebroeck et al., *Annu. Rev. Biochem* 70:535 (2001); Katso et al., *Annu. Rev. Cell Dev. Biol.* 17:615 (2001)). Of the two Class 1 PI3Ks, Class 1A PI3Ks are heterodimers composed of a catalytic p110 subunit (α, β, δ isoforms) constitutively associated with a regulatory subunit that can be p85α, p55α, p50α, p85β or p55γ. The Class 1B sub-class has one family member, a heterodimer composed of a catalytic p110γ subunit associated with one of two regulatory subunits, p101 or p84 (Fruman et al., *Annu Rev. Biochem.* 67:481 (1998); Suire et al., *Curr. Biol.* 15:566 (2005)). The modular domains of the p85/55/50 subunits include Src Homology (SH2) domains that bind phosphotyrosine residues in a specific sequence context on activated receptor and cytoplasmic tyrosine kinases, resulting in activation and localization of Class 1A PI3Ks. Class 1B PI3K is activated directly by G protein-coupled receptors that bind a diverse repertoire of peptide and non-peptide ligands (Stephens et al., *Cell* 89:105 (1997)); Katso et al., *Annu. Rev. Cell Dev. Biol.* 17:615-675 (2001)). Consequently, the resultant phospholipid products of class I PI3K link upstream receptors with downstream cellular activities including proliferation, survival, chemotaxis, cellular trafficking, motility, metabolism, inflammatory and allergic responses, transcription and translation (Cantley et al., *Cell* 64:281 (1991); Escobedo and Williams, *Nature* 335:85 (1988); Fantl et al., *Cell* 69:413 (1992)).

In many cases, PIP2 and PIP3 recruit Akt, the product of the human homologue of the viral oncogene v-Akt, to the plasma membrane where it acts as a nodal point for many intracellular signaling pathways important for growth and survival (Fantl et al., *Cell* 69:413-423(1992); Bader et al., *Nature Rev. Cancer* 5:921 (2005); Vivanco and Sawyer, *Nature Rev. Cancer* 2:489 (2002)). Aberrant regulation of PI3K, which often increases survival through Akt activation, is one of the most prevalent events in human cancer and has been shown to occur at multiple levels. The tumor suppressor gene PTEN, which dephosphorylates phosphoinositides at the 3' position of the inositol ring and in so doing antagonizes PI3K activity, is functionally deleted in a variety of tumors. In other tumors, the genes for the p110α isoform, PIK3CA, and for Akt are amplified and increased protein expression of their gene products has been demonstrated in several human cancers. Furthermore, mutations and translocation of p85α that serve to up-regulate the p85-p110 complex have been described in human cancers. Finally, somatic missense mutations in PIK3CA that activate downstream signaling pathways have been described at significant frequencies in a wide diversity of human cancers (Kang at el., *Proc. Natl. Acad. Sci. USA* 102:802 (2005); Samuels et al., *Science* 304:554 (2004); Samuels et al., *Cancer Cell* 7:561-573 (2005)). These observations show that deregulation of phosphoinositol-3 kinase and the upstream and downstream components of this signaling pathway is one of the most common deregulations associated with human cancers and proliferative diseases (Parsons et al., *Nature* 436:792 (2005); Hennessey at el., *Nature Rev. Drug Disc.* 4:988-1004 (2005)).

In view of the above, inhibitors of PI3Ks would be of particular value in the treatment of proliferative disease and other disorders. Selectivity towards the PI3K α isoform is desirable, and further desirable properties include improved pharmacokinetic properties and/or chemical stability.

WO2004/096797 discloses certain thiazole derivatives as inhibitors of PI3 kinase and their use as pharmaceutical.

WO 2005/021519 also discloses certain thiazole derivatives as inhibitors of PI3 kinase and their use as pharmaceutical.

It has now been found that the 2-carboxamide cycloamino ureas of the formula I given below have advantageous pharmacological properties and inhibit, for example, the PI3 kinases (phosphatidylinositol 3-kinase). In particular, preferably, these compounds show selectivity for PI3K alpha versus beta and/or delta and/or gamma subtypes in the biochemical and/or in the cellular assay. A further property which is preferably desirable for compounds of formula I includes improved stability, for example, improved chemical stability e.g. in solid form and/or in buffer solution. Hence, the compounds of formula I are suitable, for example, to be used in the treatment of diseases depending on the PI3 kinase (in particular PI3K alpha, such as those showing somatic mutation of PIK3CA or germline mutations or somatic mutation of PTEN), especially proliferative diseases such as tumor diseases and leukemias.

In a first aspect, the present invention provides compounds of formula I,

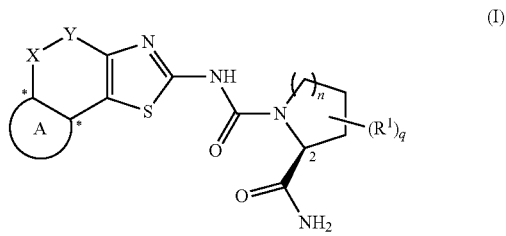

wherein,
A an unsubstituted or substituted aryl ring or unsubstituted or substituted heterocyclic ring fused to the rest of the molecule at the positions indicated by the symbol *;
X—Y is $(CH_2)_r$ or $O(CH_2)_t$ or $(CH_2)_tO$ wherein,
  r is 1, 2 or 3;
  t is 1 or 2;
n is 0, 1 or 2;
q is 0, 1, 2, 3 or 4;

$R^1$ represents, independently at each occurrence,
  halo;
  hydroxy;
  unsubstituted or substituted aryl;
  unsubstituted or substituted amino;
  unsubstituted $C_1$-$C_7$-alkyl;
  $C_1$-$C_7$-alkyl, which is substituted one or more times by hydroxy, $C_1$-$C_7$-alkoxy, unsubstituted or substituted amino, aryl or heterocyclyl, and wherein aryl may be mono or poly-substituted by halo; or
two $R^1$ substituents together form an alkandiyl to form a cyclic moiety, optionally substituted by hydroxy or halo;
or a salt, solvate, hydrate or prodrug thereof.

The invention may be more fully appreciated by reference to the following description, including the following glossary of terms and the concluding examples. As used herein, the terms "including", "containing" and "comprising" are used herein in their open, non-limiting sense.

Any formula given herein is intended to represent compounds having structures depicted by the structural formula as well as certain variations or forms. In particular, compounds of any formula given herein may have asymmetric centers and therefore exist in different stereoisomeric forms such as different enantiomeric forms. If at least one asymmetrical carbon atom is present in a compound of the formula I, such a compound may exist in optically active form or in the form of a mixture of optical isomers, e. g. in the form of a racemic mixture. Thus an asymmetric carbon atom may be present in the (R)-, (S)- or (R,S)-configuration, preferably in the (R)- or (S)-configuration. All optical isomers and their mixtures, including the racemic mixtures, are part of the present invention. Thus, any given formula given herein is intended to represent a racemate, one or more enantiomeric forms, one or more diastereomeric forms, one or more atropisomeric forms, and mixtures thereof.

Furthermore, certain structures may exist as geometric isomers (e.g. cis and trans isomers), as tautomers, or as atropisomers. For example, substituents at a double bond or a ring may be present in cis-(=Z—) or trans(=E—) form. The compounds of the invention may thus be present as mixtures of isomers or preferably as pure isomers, preferably as enantiomer-pure diastereomers or pure enantiomers.

Any formula given herein is intended to represent hydrates, solvates, and polymorphs of such compounds, and mixtures thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{31}P$, $^{32}P$, $^{18}F$, $^{35}S$, $^{36}Cl$, $^{125}I$ respectively. Various isotopically labeled compounds of the present invention, for example those into which radioactive isotopes such as $^3H$, $^{13}C$, and $^{14}C$ are incorporated. Such isotopically labelled compounds are useful in metabolic studies (preferably with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium, for example in the ranges given above.

When referring to any formula given herein, the selection of a particular moiety from a list of possible species for a specified variable is not intended to define the moiety for the variable appearing elsewhere. In other words, where a variable appears more than once, the choice of the species from a specified list is independent of the choice of the species for the same variable elsewhere in the formula (where one or more up to all more general expressions in embodiments characterized as preferred above or below can be replaced with a more specific definition, thus leading to a more preferred embodiment of the invention, respectively).

Where the plural form (e.g. compounds, salts, pharmaceutical preparations, diseases and the like) is used, this includes the singular (e.g. a single compound, a single salt, a single pharmaceutical preparation, a single disease, and the like). "A compound" does not exclude that (e.g. in a pharmaceutical formulation) more than one compound of the formula (I) (or a salt thereof) is present.

Salts are preferably the pharmaceutically acceptable salts of compounds of formula (I) if they are carrying salt-forming groups. Acids/bases required to form the salts are generally known in the field.

The following general definitions shall apply in this specification, unless otherwise specified:

Halogen (or halo) denotes fluorine, bromine, chlorine or iodine, in particular fluorine, chlorine. Halogen-substituted groups and moieties, such as alkyl substituted by halogen (halogenalkyl) can be mono-, poly- or per-halogenated.

Hetero atoms are atoms other than Carbon and Hydrogen, preferably nitrogen (N), oxygen (O) or sulfur (S), in particular nitrogen.

"Alkyl" refers to a straight-chain or branched-chain alkyl group, and includes $C_{1-7}$alkyl and more preferably $C_{1-4}$alkyl. Such alkyl groups include, for example, methyl, ethyl, n- or iso-propyl, n-, iso-, sec- or tert-butyl, n-pentyl, n-hexyl, n-heptyl, with particular preference given to methyl, ethyl, n-propyl, iso-propyl, n-butyl and iso-butyl. Alkyl may be unsubstituted or substituted. Exemplary substituents include, but are not limited to hydroxy, alkoxy, halogen (especially fluoro), amino and di-substituted amino, mono- or di-alkyl substituted amino, acetylamino, morpholinyl, aryl. An example of a substituted alkyl is trifluoromethyl. Cycloalkyl may also be a substituent to alkyl. An example of such a case is the moiety (alkyl)-cycloalkyl, such as (alkyl)-cyclopropyl or (alkyl)-cyclobutyl, e.g. methyl-cyclopropyl or methyl-cyclobutyl. A more specific example of an (alkyl)-cycloalkyl moiety includes geminal-type of substitution pattern, e.g. 1-alkyl cycloalkyl, such as 1-methyl cyclopropyl. Another example of cycloalkyl as a substituent to alkyl is alkandiyl-cycloalkyl, such as alkandiyl-cyclopropyl, e.g. —CH$_2$-cyclopropyl. $C_1$-$C_7$-alkyl is alkyl with from and including 1 up to and including 7 carbon atoms, preferably from and including 1 up to and including 4 carbon atoms ($C_1$-$C_4$-alkyl), and is linear or branched; preferably, lower alkyl is butyl, such as n-butyl, sec-butyl, isobutyl, tert-butyl, propyl, such as n-propyl or isopropyl, ethyl or preferably methyl.

Each alkyl part of other groups like "alkoxy", "alkoxyalkyl", "alkoxycarbonyl", "alkoxy-carbonylalkyl", "alkylsulfonyl", "alkylsulfoxyl", "alkylamino", "halogenalkyl" shall have the same meaning as described in the above-mentioned definition of "alkyl".

"$C_{3-7}$-Cycloalkyl" refers to a saturated or partially saturated, monocyclic, fused polycyclic, or Spiro polycyclic, carbocycle having from 3 to 7 ring atoms per carbocycle. Illustrative examples of cycloalkyl groups include the following moieties: cyclopropyl, cyclobutyl, cyclpentyl and cylclohexyl. $C_3$-$C_7$-cycloalkyl may be unsubstituted or substituted; exemplary substituents are provided in the definition for alkyl. $C_3$-$C_7$-cycloalkyl may also be a substituent on other groups, e.g. on an alkyl group.

"Aryl" refers to an unsaturated carbocyclic aromatic ring system, preferably, having a ring system of not more than 16 carbon atoms, especially not more than 10 carbon atoms, e.g. having 6 to 16, preferably 6 to 10 ring carbon atoms, is preferably mono- or bi-cyclic, and is unsubstituted or substituted. For example, aryl is unsubstituted or substituted phenyl.

"Heterocyclyl" refers to a heterocyclic radical that is unsaturated (in particular maximally unsaturated, eg. carrying the highest possible number of conjugated double bonds in the ring(s)) e.g. heteroaryl), saturated or partially saturated in the bonding ring and is preferably a monocyclic or in a broader aspect of the invention bicyclic ring; has 3-16 ring atoms, more preferably 4-10 ring atoms, wherein at least in the ring bonding to the radical of the molecule of formula (I) one or more, preferably 1-4 ring atoms, especially one or two ring atoms are a heteroatom selected from the group consisting of nitrogen, oxygen and sulfur; the bonding ring preferably having 4-12 ring atoms, especially 4-7 ring atoms, for example 6-10 ring atoms, especially for heteroaryl, such as 5, 6, 9 or 10 ring atoms. The heterocyclyl may be unsubstituted or substituted by one or more, especially 1 to 3, substituents independently selected from the group consisting of alkyl or the substituents defined above for substituted alkyl and/or from one or more of the following substituents: oxo (=O), thiocarbonyl (=S), imino (=NH), imino-lower alkyl, and, for nitrogen containing heteroaryls, including N-oxides thereof.

"Treatment" includes prophylactic (preventive) and therapeutic treatment as well as the delay of progression of a disease or disorder.

"PI3 kinase mediated diseases" (especially PI3K alpha mediated diseases) are especially such disorders that respond in a beneficial way (e.g. amelioration of one or more symptoms, delay of the onset of a disease, up to temporary or complete cure from a disease) to the inhibition of a PI3 kinase, especially inhibition of PI3Kalpha (where the diseases to be treated may include those showing somatic mutation of PIK3CA or germline mutations or somatic mutation of PTEN). Diseases to be treated include especially proliferative diseases such as tumor diseases, including solid tumors, leukemias, glioblastoma, breast cancer and prostate cancer may be mentioned).

"Salts" (which, what is meant by "or salts thereof" or "or a salt thereof"), can be present alone or in mixture with free compound of the formula I and are preferably pharmaceutically acceptable salts. Salt-forming groups in a compound of formula (I) are groups or radicals having basic or acidic properties. Compounds having at least one basic group or at least one basic radical, e.g., amino; a secondary amino group not forming a peptide bond or a pyridyl radical, may form acid addition salts, e.g., with inorganic acids, such as hydrochloric acid, sulfuric acid or a phosphoric acid; or with suitable organic carboxylic or sulfonic acids, e.g., aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid; or amino acids, such as arginine or lysine; aromatic carboxylic acids, such as benzoic acid; 2-phenoxy-benzoic acid; 2-acetoxy-benzoic acid; salicylic acid; 4-aminosalicylic acid; aromatic-aliphatic carboxylic acids, such as mandelic acid or cinnamic acid; heteroaromatic carboxylic acids, such as nicotinic acid or isonicotinic acid; aliphatic sulfonic acids, such as methane-, ethane- or 2-hydroxyethanesulfonic acid; or aromatic sulfonic acids, e.g., benzene-, p-toluene- or naphthalene-2-sulfonic acid. When several basic groups are present mono- or poly-acid addition salts may be formed.

Compounds of formula (I) having acidic groups, a carboxy group or a phenolic hydroxy group, may form metal or ammonium salts, such as alkali metal or alkaline earth metal salts, e.g., sodium, potassium, magnesium or calcium salts; or ammonium salts with ammonia or suitable organic amines, such as tertiary monoamines, e.g., triethylamine or tri(2-hydroxyethyl)-amine, or heterocyclic bases, e.g., N-ethyl-piperidine or N,N'-dimethylpiperazine. Mixtures of salts are possible.

Compounds of formula (I) having both acidic and basic groups can form internal salts.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred. In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

Compounds of the present invention may also form solvates and hydrates, and as such any reference to a compound of formula (I) is therefore to be understood as referring also to the corresponding solvate and/or hydrate of the compound of formula (I), as appropriate and expedient.

The present invention also relates to pro-drugs of a compound of formula (I) that convert in vivo to the compound of formula (I) as such. Any reference to a compound of formula (I) is therefore to be understood as referring also to the corresponding pro-drugs of the compound of formula (I), as appropriate and expedient.

Combination refers to either a fixed combination in one dosage unit form, or a kit of parts for the combined administration where a compound of the formula I and a combination partner (e.g. an other drug as explained below, also referred to as "therapeutic agent" or "co-agent") may be administered independently at the same time or separately within time intervals, especially where these time intervals allow that the combination partners show a cooperative, e.g. synergistic effect. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula I and a combination partner, are both administered to a patient simultaneously in the form of a single entity or dosage. The term "non-fixed combination" means that the active ingredients, e.g. a compound of formula I and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

In preferred embodiments, which are preferred independently, collectively or in any combination or sub-combination, the invention relates to a compound of the formula I, in free base form or in salt form, wherein the substituents are as defined herein.

As shown in formula I, the alpha-amide substituent is at the 2-position on the pyrrolidine ring and the stereochemistry at this position is as drawn.

The ring A is preferably an unsubstituted or substituted 5- or 6-membered heterocyclic (preferably a heteroaryl) ring containing 1 or 2 heteroatoms selected from N, S or O, wherein at least one heteroatom is N.

More preferably, ring A is selected from an unsubstituted or substituted pyridine ring, unsubstituted or substituted pyrimidine ring, unsubstituted or substituted thiazole ring, unsubstituted or substituted pyrazole ring or unsubstituted or substituted oxazole ring. More preferred is an unsubstituted or substituted pyridine ring, unsubstituted or substituted pyrimidine ring or unsubstituted or substituted thiazole ring.

Preferably, ring A is fused to the rest of the molecule of formula I through carbon atoms of ring A.

Ring A is preferably substituted by one, two or three $R^2$ groups, preferably two $R^2$ groups, most preferably one $R^2$ group, independently selected at each occurrence from,
unsubstituted or substituted $C_1$-$C_7$-alkyl;
unsubstituted or substituted amino;
unsubstituted or substituted $C_3$-$C_7$-cycloalkyl.

Preferably, $R^2$ is selected from
unsubstituted $C_1$-$C_7$-alkyl;
di($C_1$-C7alkyl)amino;
$C_1$-$C_7$-alkyl substituted one or more times by $C_3$-$C_7$-cycloalkyl or halo (preferably fluoro);
unsubstituted $C_3$-$C_7$-cycloalkyl;
$C_3$-$C_7$-cycloalkyl which is substituted one or more times by halo (preferably fluoro), (halo-$C_1$-$C_7$-alkyl) or $C_1$-$C_7$-alkyl;

More preferably, $R^2$ is selected from methyl, t-butyl, diethylamino, cyclopropylmethyl, 2-fluoro-1,1-dimethylethyl or 2,2,2-trifluoro-1,1-dimethyl-ethyl.

In another embodiment, $R^2$ is selected from methyl, t-butyl, diethylamino, cyclopropylmethyl or 2-fluoro-1,1-dimethylethyl.

The ring A is more preferably selected from A1 or A2 or A3 or A4 or A5 or A6:

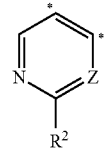

A1

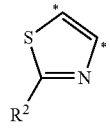

A2

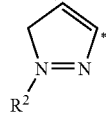

A3

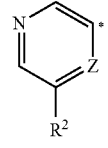

A4

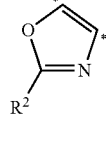

A5

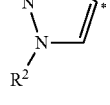

A6 wherein,
Z is N or CH and $R^2$ is defined as above.
Preferably, ring A is selected from A1 or A2.
X—Y preferably represents $(CH_2)_r$ or $O(CH_2)_t$ wherein,
r is 1, 2 or 3;
t is 1 or 2;
X—Y more preferably represents $(CH_2)_r$ or $O(CH_2)_t$ wherein r is 2 and t is 1. For the avoidance of doubt, that is, X—Y is preferably —CH₂—CH₂— or —O—CH₂—, such that in the latter case, the X in X—Y is the O in —O—CH₂—.

R¹ preferably represents, independently at each occurrence, halo;
hydroxy;
unsubstituted or substituted phenyl;
di(C₁-C₇-alkyl)amino;
unsubstituted C₁-C₇-alkyl;
C₁-C₇-alkyl, which is substituted one or more times by hydroxy, C₁-C₇-alkoxy, di(C₁-C₇-alkyl)amino, di-(perdeuteroC₁-C₇-alkyl)amino, phenyl, morpholinyl, acetylamino, or N—(C₁-C₇-alkyl)-N-(phenylC₁-C₇-alkyl)amino, and wherein independently each phenyl may be mono or poly-substituted by halo.

R¹ more preferably represents, independently at each occurrence, fluoro;
hydroxy;
unsubstituted phenyl;
dimethylamino;
methyl;
methyl, which is substituted one or more times (preferably substituted once) by hydroxy, methoxy, dimethylamino, di-(perdeuteromethyl)amino, phenyl, morpholinyl, acetylamino, or N-(methyl)-N-(phenylmethyl)amino, and wherein independently each phenyl may be mono or poly-substituted by fluoro.

R¹ most preferably represents, independently at each occurrence, fluoro;
hydroxy;
unsubstituted phenyl;
dimethylamino;
methyl;
hydroxy methyl;
methoxy methyl;
dimethylamino methyl;
di-(perdeuteromethyl)amino methyl;
benzyl;
morpholin-4-yl methyl;
N-acetylamino methyl;
N-(methyl)-N-(3-fluoro-phenylmethyl)amino methyl.

An embodiment of the present invention includes compounds of the formula I wherein n is 0 or 1. Preferably, n is 1.

Another embodiment of the present invention includes compounds of the formula I wherein q is 0, that is, wherein the nitrogen containing heterocyclic ring is substituted only by the amide at position 2. In this embodiment, it is preferred that n is 0 or 1, more preferably 1.

Another embodiment of the present invention includes compounds of the formula I wherein q is 1, that is, wherein the nitrogen containing heterocyclic ring is substituted only by the amide at position 2 and a single R¹ group. In this embodiment it is preferred that n is 0 or 1, more preferably 1. In this embodiment, the R¹ group may be substituted at position 2- (i.e. on the same carbon as that which is substituted by the amide group) or position 3- or position 4- or position 5- of the nitrogen containing heterocyclic ring.

Preferably, in this embodiment, the R¹ group is substituted at position 3 of the nitrogen containing heterocyclic ring, i.e. compounds of formula IA:

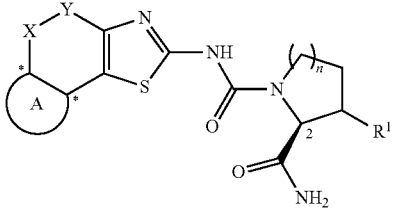

wherein the substitutents are defined as for a compound of formula (I).

Preferably in compounds of formula IA, n is 1, thus providing compounds wherein the nitrogen containing heterocyclic ring is a pyrrolidine ring, substituted at the 2-position by an amide having the drawn stereochemistry, and in the 3-position by an R¹ group.

Preferably, the R¹ group has a stereochemistry which is cis- to the amide at position 2, i.e. compounds according to formula (IA'):

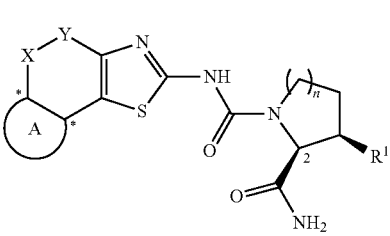

wherein the substitutents are defined as for a compound of formula (I).

Preferably in compounds of formula IA', n is 1, thus providing compounds wherein the nitrogen containing heterocyclic ring is a pyrrolidine ring, substituted at the 2-position by an amide having the drawn stereochemistry, and in the 3-position by an R¹ group having the drawn stereochemisty, thus the amide and R¹ groups are cis-relative to each other.

A further embodiment of the present invention includes compounds of the formula I wherein q is 2 or 3, thus at least two R¹ substituents are present, each R¹ independently selected from the groups defined as for formula I herein. In this embodiment, it is preferred that at least each of two R¹ is bonded at position 3 of the pyrrolidine ring, and an optional third R¹ group, if present, is bonded elsewhere on the nitrogen containing heterocyclic ring. It is further preferred that n is 1 and the third R¹ group, if present, is bonded at the 4- or 5-position of the resultant pyrrolidine ring, i.e. to provide compounds of formula IB:

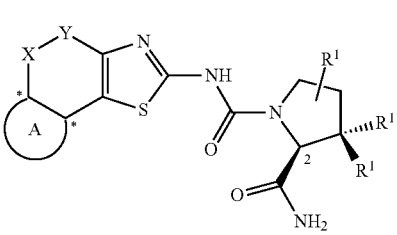

wherein the substitutents are defined as for a compound of formula (I).

In compounds according to formula IB, it is preferred that the third R¹ is bonded at position 4- of the pyrrolidine ring.

A further embodiment of the present invention includes compounds of the formula I wherein n is 1, and wherein two R¹ groups are bonded at position 3 of the pyrrolidine ring, and, together form an alkandiyl, preferably a $C_3$-$C_8$-cycloalkyl, in particular a cyclopropyl, i.e. to provide compounds of formula IC:

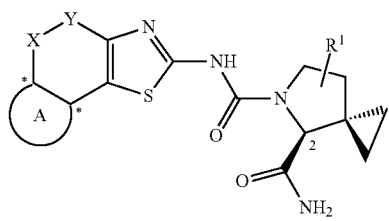

(IC)

wherein the substitutents are defined as for a compound of formula (I) and the third R¹ group is optional, and if present, is preferably bonded at position 4- of the pyrrolidine ring.

In any of the formulae (IA), (IA'), (IB) or (IC), the preferred definitions, if not otherwise stated, for ring A, X—Y, R¹ and n can also apply.

The invention further relates to pharmaceutically acceptable prodrugs of a compound of formula (I), (IA), (IA'), (IB) and/or (IC).

The invention further relates to pharmaceutically acceptable metabolites of a compound of formula (I), (IA), (IA'), (IB) and/or (IC).

The invention relates especially to the compounds of the formula (I), (IA), (IA'), (IB) and/or (IC) given in the Examples, as well as the methods of manufacture described herein.

The present invention also relates to processes for the production of a compound of formula (I), (IA), (IA'), (IB) and/or (IC). In principle all known processes which convert two different amines into a corresponding urea derivative are suitable and may be applied by using the respective starting material.

Thus, the invention in particular relates to a process which comprises reacting a compound of formula II

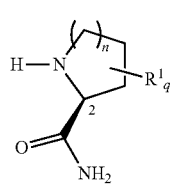

(II)

wherein the substituents are as defined above, either with a compound of formula IIIA

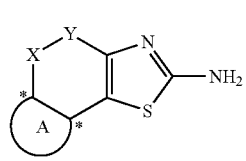

(IIIA)

wherein the substituents are as defined above, in the presence of an activating agent ("method A") or with a compound of formula IIIB

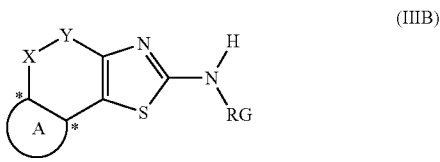

(IIIB)

wherein R¹ is as defined above; RG represents a reactive group (such as imidazolylcarbonyl) ("method B"), in each case optionally in the presence of a diluent and optionally in the presence of a reaction aid and recovering the resulting compound of formula I in free form or in form of a salt and, optionally converting a compound of the formula I obtainable according to method A or method B into a different compound of the formula I, and/or converting an obtainable salt of a compound of the formula I into a different salt thereof, and/or converting an obtainable free compound of the formula I into a salt thereof, and/or separating an obtainable isomer of a compound of the formula I from one or more different obtainable isomers of the formula I.

Reaction Conditions

The process may be performed according to methods known in the art, or as disclosed below in the Examples. For example a compound of formula II may be reacted with a compound of formula IIIA or IIIB in a solvent, e.g. dimethylformamide, in the presence of a base e.g. an organic amine, e.g. triethylamine.

Where temperatures are given hereinbefore or hereinafter, "about" has to be added, as minor deviations from the numeric values given, e.g. variations of ±10%, are typically tolerable. All reactions may take place in the presence of one or more diluents and/or solvents. The starting materials may be used in equimolar amounts; alternatively, a compound may be used in excess, e.g. to function as a solvent or to shift equilibrium or to generally accelerate reaction rates.

Reaction aids, such as acids, bases or catalysts may be added in suitable amounts, as known in the field, required by a reaction and in line with generally known procedures.

Protecting Groups

If one or more other functional groups, for example carboxy, hydroxy, amino, sulfhydryl or the like are or need to be protected in a starting material as described herein or any other precursor, because they should not take part in the reaction or disturb the reaction, these are such groups as are usually used in the synthesis of peptide compounds, and also of cephalosporins and penicillins, as well as nucleic acid derivatives and sugars. Protecting groups are such groups that are no longer present in the final compounds once they are removed, while groups that remain as substituents are not protecting groups in the sense used here which are groups that are added at a starting material or intermediate stage and removed to obtain a final compound. Also in the case of conversions of a compound of the formula (I), (IA), (IA'), (IB) and/or (IC) into a different compound of the formula (I), (IA), (IA'), (IB) and/or (IC), protecting groups may be introduced and removed, if useful or required. The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by acetolysis, protonolysis, solvolysis, reduction, photolysis or also by enzyme activity, for example under conditions analogous to physiological conditions, and that they are not present in the end-products. The specialist knows, or can easily establish, which protecting groups are suitable with the reactions mentioned above and below.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/1, Georg Thieme Verlag, Stuttgart 1974, in H.-D. Jakubke and H. Jescheit, "Aminosäuren, Peptide, Proteine" (*Amino acids, peptides, proteins*), Verlag Chemie, Weinheim, Deerfield Beach, and Basel 1982, and in Jochen Lehmann, "Chemie der Kohlenhydrate: Monosaccharide and Derivate" (*Chemistry of carbohydrates: monosaccharides and derivatives*), Georg Thieme Verlag, Stuttgart 1974.

Optional Reactions and Conversions

A compound of the formula (I), (IA), (IA'), (IB) and/or (IC) may be converted into a different compound of the formula (I), (IA), (IA'), (IB) and/or (IC).

In a compound of the formula (I), (IA), (IA'), (IB) and/or (IC) wherein a substituent carries an amino or amino-$C_1$-$C_7$-alkyl substituent, the amino can be converted into acylamino, e.g. $C_1$-$C_7$-alkanoylamino, by reaction with a corresponding $C_1$-$C_7$-alkanoylhalogenide, e.g. a corresponding chloride, in the presence of a tertiary nitrogen base, such as triethylamine or pyridine, in the absence or presence of an appropriate solvent, such a methylene chloride, for example at temperatures in the range from −20 to 50° C., e.g. at about room temperature.

Salts of a compound of formula (I), (IA), (IA'), (IB) and/or (IC) with a salt-forming group may be prepared in a manner known per se. Acid addition salts of compounds of formula (I), (IA), (IA'), (IB) and/or (IC) may thus be obtained by treatment with an acid or with a suitable anion exchange reagent. A salt with two acid molecules (for example a dihalogenide of a compound of formula (I), (IA), (IA'), (IB) and/or (IC)) may also be converted into a salt with one acid molecule per compound (for example a monohalogenide); this may be done by heating to a melt, or for example by heating as a solid under a high vacuum at elevated temperature, for example from 130 to 170° C., one molecule of the acid being expelled per molecule of a compound of formula (I), (IA), (IA'), (IB) and/or (IC). Salts can usually be converted to free compounds, e.g. by treating with suitable basic compounds, for example with alkali metal carbonates, alkali metal hydrogencarbonates, or alkali metal hydroxides, typically potassium carbonate or sodium hydroxide.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of a starting compound or in a compound of formula (I), (IA), (IA'), (IB) and/or (IC) itself. Enantiomers may be separated through the formation of diastereomeric salts, for example by salt formation with an enantiomer-pure chiral acid, or by means of chromatography, for example by HPLC, using chromatographic substrates with chiral ligands.

It should be emphasized that reactions analogous to the conversions mentioned herein may also take place at the level of appropriate intermediates (and are thus useful in the preparation of corresponding starting materials).

Starting Materials:

The starting materials of the formulae II and III, as well as other starting materials mentioned herein, e.g. below, can be prepared according to or in analogy to methods that are known in the art, are known in the art and/or are commercially available. Insofar as the production of the starting materials is not particularly described, the compounds are either known or may be prepared analogously to methods known in the art, e.g. in WO 05/021519 or WO04/096797, or as disclosed hereinafter. Novel starting materials, as well as processes for the preparation thereof, are likewise an embodiment of the present invention. In the preferred embodiments, such starting materials are used and the reaction chosen are selected so as to enable the preferred compounds to be obtained.

In the starting materials (including intermediates), which may also be used and/or obtained as salts where appropriate and expedient, the substituents are preferably as defined for a compound of the formula (I), (IA), (IA'), (IB) and/or (IC).

Pharmaceutical compositions, uses and methods of treatment

The present invention also relates to use of the compounds of formula (I), (IA), (IA'), (IB) and/or (IC) as disclosed herein as pharmaceuticals. The present invention includes in one embodiment compositions comprising a compound of formula (I), (IA), (IA'), (IB) and/or (IC), e.g. for human or veterinary use, e.g. where inhibition of PI3K is indicated.

In one embodiment, the invention relates to the treatment of cellular proliferative diseases such as tumor (benign or malignant) and/or cancerous cell growth, e.g. mediated by PI3K. Diseases may include those showing somatic mutation of PIK3CA or germline mutations or somatic mutation of PTEN. In particular, the compounds may be useful in the treatment of human or animal (e.g., murine) cancers, including, for example, sarcoma; lung; bronchus; prostate; breast (including sporadic breast cancers and sufferers of Cowden disease); pancreas; gastrointestinal cancer; colon; rectum; colon carcinoma; colorectal adenoma; thyroid; liver; intrahepatic bile duct; hepatocellular; adrenal gland; stomach; gastric; glioma; glioblastoma; endometrial; melanoma; kidney; renal pelvis; urinary bladder; uterine corpus; uterine cervix; vagina; ovary; multiple myeloma; esophagus; a leukemia; acute myelogenous leukemia; chronic myelogenous leukemia; lymphocytic leukemia; myeloid leukemia; brain; a carcinoma of the brain; oral cavity and pharynx; larynx; small intestine; non-Hodgkin lymphoma; melanoma; villous colon adenoma; a neoplasia; a neoplasia of epithelial character; lymphomas; a mammary carcinoma; basal cell carcinoma; squamous cell carcinoma; actinic keratosis; tumor diseases, including solid tumors; a tumor of the neck or head; polycythemia Vera; essential thrombocythemia; and myelofibrosis with myeloid metaplasia.

In other embodiments, the condition or disorder (e.g. PI3K-mediated) is selected from the group consisting of: an epidermal hyperproliferation, prostate hyperplasia, a neoplasia, a neoplasia of epithelial character, Cowden syndrome, Lhermitte-Dudos disease or Bannayan-Zonana syndrome, asthma, COPD, ARDS, Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma, eosinophil-related disorders affecting the airways occasioned by drug-reaction, psoriasis, contact dermatitis, atopic dermatitis, alopecia areata, erythema multiforme, dermatitis herpetiformis, scleroderma, vitiligo, hypersensitivity angiitis, urticaria, bullous pemphigoid, lupus erythematosus, pemphisus, epidermolysis bullosa acquisita, autoimmune haematogical disorders (e.g. haemolytic anaemia, aplastic anaemia, pure red cell anaemia and idiopathic thrombocytopenia), systemic lupus erythematosus, polychondritis, scleroderma, Wegener granulomatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), interstitial lung fibrosis, psoriatic arthritis, glomerulonephritis, cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease, reperfusion injuries, retinopathy, such as diabetic retinopathy or hyperbaric oxygen-induced retinopathy, and conditions characterized by elevated intraocular pressure or secretion of ocular aqueous humor, such as glaucoma.

For the above uses the required dosage will of course vary depending on the mode of administration, the particular condition to be treated and the effect desired. In general, satisfactory results are indicated to be obtained systemically at daily dosages of from about 0.03 to 10.0 mg/kg per body weight. An indicated daily dosage in the larger mammal, e.g. humans, is in the range from about 0.5 mg to about 1 g, conveniently administered, for example, in divided doses up to four times a day or in retard form. Suitable unit dosage forms for oral administration comprise from ca. 0.1 to 500 mg active ingredient.

The compounds of formula (I), (IA), (IA'), (IB) and/or (IC) may be administered by any conventional route, in particular enterally, e.g. orally, e.g. in the form of tablets or capsules, or parenterally, e.g. in the form of injectable solutions or suspensions, topically, e.g. in the form of lotions, gels, ointments or creams, by inhalation, intranasally, or in a suppository form.

The compounds of formula (I), (IA), (IA'), (IB) and/or (IC) may be administered in free form or in pharmaceutically acceptable salt form e.g. as indicated above. Such salts may be prepared in conventional manner and exhibit the same order of activity as the free compounds.

Consequently, the invention also provides:
  a method for preventing or treating conditions, disorders or diseases mediated by the activation of the PI3, e.g. the PI3 kinase alpha enzyme e.g. such as indicated above, in a subject in need of such treatment, which method comprises administering to said subject an effective amount of a compound of formula (I), (IA), (IA'), (IB) and/or (IC) or a pharmaceutically acceptable salt thereof
  use of a compound of formula (I), (IA), (IA'), (IB) and/or (IC), in free form or in a pharmaceutically acceptable salt form as a pharmaceutical, e.g. in any of the methods as indicated herein.
  a compound of the formula (I), (IA), (IA'), (IB) and/or (IC) in free form or in pharmaceutically acceptable salt form for use as pharmaceutical, e.g. in any of the methods as indicated herein, in particular for the use in one or more phosphatidylinositol 3-kinase mediated diseases.
  the use of a compound of formula (I), (IA), (IA'), (IB) and/or (IC) in free form or in pharmaceutically acceptable salt form in any of the methods as indicated herein, in particular for the treatment of one or more phosphatidylinositol 3-kinase mediated diseases.
  the use of a compound of formula (I), (IA), (IA'), (IB) and/or (IC) in free form or in pharmaceutically acceptable salt form in any of the methods as indicated herein, in particular for the manufacture of a medicament for the treatment of one or more phosphatidylinositol 3-kinase mediated diseases.

PI3K serves as a second messenger node that integrates parallel signaling pathways, evidence is emerging that the combination of a PI3K inhibitor with inhibitors of other pathways will be useful in treating cancer and proliferative diseases in humans. Approximately 20-30% of human breast cancers overexpress Her-2/neu-ErbB2, the target for the drug trastuzumab. Although trastuzumab has demonstrated durable responses in some patients expressing Her2/neu-ErbB2, only a subset of these patients respond. Recent work has indicated that this limited response rate can be substantially improved by the combination of trastuzumab with inhibitors of PI3K or the PI3K/AKT pathway (Chan et al., Breast Can. Res. Treat. 91:187 (2005), Woods Ignatoski et al., Brit. J. Cancer 82:666 (2000), Nagata et al., Cancer Cell 6:117 (2004)).

A variety of human malignancies express activating mutations or increased levels of Her1/EGFR and a number of antibody and small molecule inhibitors have been developed against this receptor tyrosine kinase including tarceva, gefitinib and erbitux. However, while EGFR inhibitors demonstrate anti-tumor activity in certain human tumors (e.g., NSCLC), they fail to increase overall patient survival in all patients with EGFR-expressing tumors. This may be rationalized by the fact that many downstream targets of Her1/EGFR are mutated or deregulated at high frequencies in a variety of malignancies, including the PI3K/Akt pathway. For example, gefitinib inhibits the growth of an adenocarcinoma cell line in in vitro assays. Nonetheless, sub-clones of these cell lines can be selected that are resistant to gefitinib that demonstrate increased activation of the PI3/Akt pathway. Down-regulation or inhibition of this pathway renders the resistant sub-clones sensitive to gefitinib (Kokubo et al., Brit. J. Cancer 92:1711 (2005)). Furthermore, in an in vitro model of breast cancer with a cell line that harbors a PTEN mutation and over-expresses EGFR inhibition of both the PI3K/Akt pathway and EGFR produced a synergistic effect (She et al., Cancer Cell 8:287-297(2005)). These results indicate that the combination of gefitinib and PI3K/Akt pathway inhibitors would be an attractive therapeutic strategy in cancer.

The combination of AEE778 (an inhibitor of Her-2/neu/ErbB2, VEGFR and EGFR) and RAD001 (an inhibitor of mTOR, a downstream target of Akt) produced greater combined efficacy that either agent alone in a glioblastoma xenograft model (Goudar et al., Mol. Cancer. Ther. 4:101-112 (2005)).

Anti-estrogens, such as tamoxifen, inhibit breast cancer growth through induction of cell cycle arrest that requires the action of the cell cycle inhibitor p27Kip. Recently, it has been shown that activation of the Ras-Raf-MAP Kinase pathway alters the phosphorylation status of p27Kip such that its inhibitory activity in arresting the cell cycle is attenuated, thereby contributing to anti-estrogen resistance (Donovan, et al, J. Biol. Chem. 276:40888, (2001)). As reported by Donovan et al., inhibition of MAPK signaling through treatment with MEK inhibitor reversed the aberrant phosphorylation status of p27 in hormone refractory breast cancer cell lines and in so doing restored hormone sensitivity. Similarly, phosphorylation of p27Kip by Akt also abrogates its role to arrest the cell cycle (Viglietto et al., Nat Med. 8:1145 (2002)).

Accordingly, the present invention provides, in a further aspect, compounds of formulae (I), (IA), (IA'), (IB) and/or (IC) for use in the treatment of hormone dependent cancers, such as breast and prostate cancers. By this use, it is aimed to reverse hormone resistance commonly seen in these cancers with conventional anticancer agents.

In hematological cancers, such as chronic myelogenous leukemia (CML), chromosomal translocation is responsible for the constitutively activated BCR-Abl tyrosine kinase. The afflicted patients are responsive to imatinib, a small molecule tyrosine kinase inhibitor, as a result of inhibition of Abl kinase activity. However, many patients with advanced stage disease respond to imatinib initially, but then relapse later due to resistance-conferring mutations in the Abl kinase domain. In vitro studies have demonstrated that BCR-Ab1 employs the Ras-Raf kinase pathway to elicit its effects. In addition, inhibiting more than one kinase in the same pathway provides additional protection against resistance-conferring mutations.

Accordingly, in another aspect, the present invention provides the compounds of formulae (I), (IA), (IA'), (IB) and/or (IC) for use in combination with at least one additional agent selected from the group of kinase inhibitors, such as Gleevec®, in the treatment of hematological cancers, such as chronic myelogenous leukemia (CML). By this use, it is aimed to reverse or prevent resistance to said at least one additional agent.

Because activation of the PI3K/Akt pathway drives cell survival, inhibition of the pathway in combination with therapies that drive apoptosis in cancer cells, including radiotherapy and chemotherapy, will result in improved responses (Ghobrial et al., CA Cancer J. Clin 55:178-194 (2005)). As an example, combination of PI3 kinase inhibitor with carboplatin demonstrated synergistic effects in both in vitro proliferation and apoptosis assays as well as in in vivo tumor efficacy in a xenograft model of ovarian cancer (Westfall and Skinner, Mol. Cancer Ther. 4:1764-1771 (2005)).

In addition to cancer and proliferative diseases, there is accumulating evidence that inhibitors of Class 1A and 1B PI3 kinases would be therapeutically useful in others disease areas. The inhibition of p110β, the PI3K isoform product of the PIK3CB gene, has been shown to be involved in shear-induced platelet activation (Jackson et al., Nature Medicine 11:507-514 (2005)). Thus, a PI3K inhibitor that inhibits p110β would be useful as a single agent or in combination in anti-thrombotic therapy. The isoform p110δ, the product of the PIK3CD gene, is important in B cell function and differentiation (Clayton et al., J. Exp. Med. 196:753-763 (2002)), T-cell dependent and independent antigen responses (Jou et al., Mol. Cell. Biol. 22:8580-8590 (2002)) and mast cell differentiation (Ali et al., Nature 431:1007-1011 (2004)). Thus, it is expected that p110δ-inhibitors would be useful in the treatment of B-cell driven autoimmune diseases and asthma. Finally, the inhibition of p110γ, the isoform product of the PI3KCG gene, results in reduced T, but not B cell, response (Reif et al., J. Immunol. 173:2236-2240 (2004)) and its inhibition demonstrates efficacy in animal models of autoimmune diseases (Camps et al., Nature Medicine 11:936-943 (2005), Barber et al., Nature Medicine 11:933-935 (2005)).

The invention further provides pharmaceutical compositions comprising at least one compound of formula (I), (IA), (IA'), (IB) and/or (IC), together with a pharmaceutically acceptable excepient suitable for administration to a human or animal subject, either alone or together with another therapeutic agent, for example another anticancer agent.

The invention further provides methods of treating human or animal subjects suffering from a cellular proliferative disease, such as cancer. The invention thus provides methods of treating a human or animal subject in need of such treatment, comprising administering to the subject a therapeutically effective amount of a compound of formula (I), (IA), (IA'), (IB) and/or (IC) either alone or in combination with one or more other therapeutic agents, e.g. other anticancer agents. In particular, compositions will either be formulated together as a combination therapeutic or administered separately. Suitable anticancer agents for use with a compound of formula I include, but are not limited to, one or more compounds selected from the group consisting of kinase inhibitors, anti-estrogens, anti androgens, other inhibitors, cancer chemotherapeutic drugs, alkylating agents, chelating agents, biological response modifiers, cancer vaccines, agents for antisense therapy as set forth below:

A. Kinase Inhibitors: Kinase inhibitors for use as anticancer agents in conjunction with a compound of the formula (I), (IA), (IA'), (IB) and/or (IC) include inhibitors of Epidermal Growth Factor Receptor (EGFR) kinases such as small molecule quinazolines, for example gefitinib (U.S. Pat. Nos. 5,457,105, 5,616,582, and 5,770,599), ZD-6474 (WO 01/32651), erlotinib (Tarceva®, U.S. Pat. No. 5,747,498 and WO 96/30347), and lapatinib (U.S. Pat. No. 6,727,256 and WO 02/02552); Vascular Endothelial Growth Factor Receptor (VEGFR) kinase inhibitors, including SU-11248 (WO 01/60814), SU 5416 (U.S. Pat. No. 5,883,113 and WO 99/61422), SU 6668 (U.S. Pat. No. 5,883,113 and WO 99/61422), CHIR-258 (U.S. Pat. Nos. 6,605,617 and 6,774,237), vatalanib or PTK-787 (U.S. Pat. No. 6,258,812), VEGF-Trap (WO 02/57423), B43-Genistein (WO-09606116), fenretinide (retinoic acid p-hydroxyphenylamine) (U.S. Pat. No. 4,323,581), IM-862 (WO 02/62826), bevacizumab or Avastin® (WO 94/10202), KRN-951, 3-[5-(methylsulfonylpiperadine methyl)-indolyl]-quinolone, AG-13736 and AG-13925, pyrrolo[2,1-f][1,2,4]triazines, ZK-304709, Veglin®, VMDA-3601, EG-004, CEP-701 (U.S. Pat. No. 5,621,100), Cand5 (WO 04/09769); Erb2 tyrosine kinase inhibitors such as pertuzumab (WO 01/00245), trastuzumab, and rituximab; Akt protein kinase inhibitors, such as RX-0201; Protein Kinase C (PKC) inhibitors, such as LY-317615 (WO 95/17182), and perifosine (US 2003171303); Raf/Map/MEK/Ras kinase inhibitors including sorafenib (BAY 43-9006), ARQ-350RP, LErafAON, BMS-354825 AMG-548, and others disclosed in WO 03/82272; Fibroblast Growth Factor Receptor (FGFR) kinase inhibitors; Cell Dependent Kinase (CDK) inhibitors, including CYC-202 or roscovitine (WO 97/20842 and WO 99/02162); Platelet-Derived Growth Factor Receptor (PDGFR) kinase inhibitors such as CHIR-258, 3G3 mAb, AG-13736, SU-11248 and SU6668; and Bcr-Abl kinase inhibitors and fusion proteins such as STI-571 or Gleevec® (imatinib).

B. Anti-Estrogens: Estrogen-targeting agents for use in anticancer therapy in conjunction with a compound of formula (I), (IA), (IA'), (IB) and/or (IC) include Selective Estrogen Receptor Modulators (SERMs) including tamoxifen, toremifene, raloxifene; aromatase inhibitors including Arimidex® or anastrozole; Estrogen Receptor Downregulators (ERDs) including Faslodex® or fulvestrant.

C. Anti-Androgens: Androgen-targeting agents for use in anticancer therapy in conjunction with a compound of formula (I), (IA), (IA'), (IB) and/or (IC) include flutamide, bicalutamide, finasteride, aminoglutethamide, ketoconazole, and corticosteroids.

D. Other Inhibitors: Other inhibitors for use as anticancer agents in conjunction with a compound of formula (I), (IA), (IA'), (IB) and/or (IC) include protein farnesyl transferase inhibitors including tipifarnib or R-115777 (US 2003134846 and WO 97/21701), BMS-214662, AZD-3409, and FTI-277; topoisomerase inhibitors including merbarone and diflomotecan (BN-80915); mitotic kinesin spindle protein (KSP) inhibitors including SB-743921 and MKI-833; proteasome modulators such as bortezomib or Velcade® (U.S. Pat. No. 5,780,454), XL-784; and cyclooxygenase 2 (COX-2) inhibitors including non-steroidal antiinflammatory drugs I (NSAIDs).

E. Cancer Chemotherapeutic Drugs: Particular cancer chemotherapeutic agents for use as anticancer agents in conjunction with a compound of formula (I), (IA), (IA'), (IB) and/or (IC) include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®, US 2004073044), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbin®).

F. Alkylating Agents: Alkylating agents for use in conjunction with a compound of formula (I), (IA), (IA'), (IB) and/or (IC) include VNP-40101M or cloretizine, oxaliplatin (U.S. Pat. No. 4,169,846, WO 03/24978 and WO 03/04505), glufosfamide, mafosfamide, etopophos (U.S. Pat. No. 5,041,424), prednimustine; treosulfan; busulfan; irofluven (acylfulvene); penclomedine; pyrazoloacridine (PD-115934); O6-benzylguanine; decitabine (5-aza-2-deoxycytidine); brostallicin; mitomycin C (MitoExtra); TLK-286 (Telcyta®); temozolomide; trabectedin (U.S. Pat. No. 5,478,932); AP-5280 (Platinate formulation of Cisplatin); porfiromycin; and clearazide (meclorethamine).

G. Chelating Agents: Chelating agents for use in conjunction with a compound of formula (I), (IA), (IA'), (IB) and/or (IC) include tetrathiomolybdate (WO 01/60814); RP-697; Chimeric T84.66 (cT84.66); gadofosveset (Vasovist®); deferoxamine; and bleomycin optionally in combination with electorporation (EPT).

H. Biological Response Modifiers: Biological response modifiers, such as immune modulators, for use in conjunction with a compound of formula (I), (IA), (IA'), (IB) and/or (IC) include staurosprine and macrocyclic analogs thereof, including UCN-01, CEP-701 and midostaurin (see WO 02/30941, WO 97/07081, WO 89/07105, U.S. Pat. No. 5,621,100, WO 93/07153, WO 01/04125, WO 02/30941, WO 93/08809, WO 94/06799, WO 00/27422, WO 96/13506 and WO 88/07045); squalamine (WO 01/79255); DA-9601 (WO 98/04541 and U.S. Pat. No. 6,025,387); alemtuzumab; interferons (e.g. IFN-a, IFN-b etc.); interleukins, specifically IL-2 or aldesleukin as well as IL-1, IL-3, IL-4, IL-5, IL-6, IL-7, IL-8, IL-9, IL-10, IL-11, IL-12, and active biological variants thereof having amino acid sequences greater than 70% of the native human sequence; altretamine (Hexalen®); SU 101 or leflunomide (WO 04/06834 and U.S. Pat. No. 6,331,555); imidazoquinolines such as resiquimod and imiquimod (U.S. Pat. Nos. 4,689,338, 5,389,640, 5,268,376, 4,929,624, 5,266,575, 5,352,784, 5,494,916, 5,482,936, 5,346,905, 5,395,937, 5,238,944, and 5,525,612); and SMIPs, including benzazoles, anthraquinones, thiosemicarbazones, and tryptanthrins (WO 04/87153, WO 04/64759, and WO 04/60308).

I. Cancer Vaccines: Anticancer vaccines for use in conjunction with a compound of formula (I), (IA), (IA'), (IB) and/or (IC) include Avicine® (Tetrahedron Lett. 26:2269-70 (1974)); oregovomab (OvaRex®); Theratope® (STn-KLH); Melanoma Vaccines; GI-4000 series (GI-4014, GI-4015, and GI-4016), which are directed to five mutations in the Ras protein; GlioVax-1; MelaVax; Advexin® or INGN-201 (WO 95/12660); Sig/E7/LAMP-1, encoding HPV-16 E7; MAGE-3 Vaccine or M3TK (WO 94/05304); HER-2VAX; ACTIVE, which stimulates T-cells specific for tumors; GM-CSF cancer vaccine; and Listeria monocytogenes-based vaccines.

J. Antisense Therapy: Anticancer agents for use in conjunction with a compound of formula (I), (IA), (IA'), (IB) and/or (IC) also include antisense compositions, such as AEG-35156 (GEM-640); AP-12009 and AP-11014 (TGF-beta2-specific antisense oligonucleotides); AVI-4126; AVI-4557; AVI-4472; oblimersen (Genasense®); JFS2; aprinocarsen (WO 97/29780); GTI-2040 (R2 ribonucleotide reductase mRNA antisense oligo) (WO 98/05769); GTI-2501 (WO 98/05769); liposome-encapsulated c-Raf antisense oligodeoxynucleotides (LErafAON) (WO 98/43095); and Sirna-027 (RNAi-based therapeutic targeting VEGFR-1 mRNA).

A compound of formula (I), (IA), (IA'), (IB) and/or (IC) may also be combined in a pharmaceutical composition with bronchiodilatory or antihistamine drugs substances. Such bronchiodilatory drugs include anticholinergic or antimuscarinic agents, in particular glycopyrrolate, ipratropium bromide, oxitropium bromide, and tiotropium bromide, OrM3, aclidinium, CHF5407, GSK233705 and β-2-adrenoreceptor agonists such as salbutamol, terbutaline, salmeterol, carmoterol, milveterol and, especially, indacaterol and formoterol. Co-therapeutic antihistamine drug substances include cetirizine hydrochloride, clemastine fumarate, promethazine, loratadine, desloratadine diphenhydramine and fexofenadine hydrochloride.

The invention provides in a further aspect a combination comprising a compound of formula (I), (IA), (IA'), (IB) and/or (IC) and one or more compounds that are useful for the treatment of a thrombolytic disease, heart disease, stroke, etc. Such compounds include aspirin, a streptokinase, a tissue plasminogen activator, a urokinase, a anticoagulant, antiplatelet drugs (e.g, PLAVIX; clopidogrel bisulfate), a statin (e.g., LIPITOR or Atorvastatin calcium), ZOCOR (Simvastatin), CRESTOR (Rosuvastatin), etc.), a Beta blocker (e.g., Atenolol), NORVASC (amlodipine besylate), and an ACE inhibitor (e.g., lisinopril).

The invention provides in a further aspect a combination comprising a compound of formula (I), (IA), (IA'), (IB) and/or (IC) and one or more compounds that are useful for the treatment of antihypertension. Such compounds include ACE inhibitors, lipid lowering agents such as statins, LIPITOR (Atorvastatin calcium), calcium channel blockers such as NORVASC (amlodipine besylate).

The invention provides in a further aspect a combination comprising a compound of formula (I), (IA), (IA'), (IB) and/or (IC) and one or more compounds selected from the group consisting of fibrates, beta-blockers, NEPI inhibitors, Angiotensin-2 receptor antagonists and platelet aggregation inhibitors.

The invention provides in a further aspect a combination comprising a compound of formula (I), (IA), (IA'), (IB) and/or (IC) and a compound suitable for the treatment of inflammatory diseases, including rheumatoid arthritis. Such compound may be selected from the group consisting of TNF-$\alpha$ inhibitors such as anti-TNF-$\alpha$ monoclonal antibodies (such as REMICADE, CDP-870) and D2E7 (HUMIRA) and TNF receptor immunoglobulin fusion molecules (such as ENBREL), IL-1 inhibitors, receptor antagonists or soluble IL-1R$\alpha$ (e.g. KINERET or ICE inhibitors), nonsterodial anti-inflammatory agents (NSAIDS), piroxicam, diclofenac, naproxen, flurbiprofen, fenoprofen, ketoprofen ibuprofen, fenamates, mefenamic acid, indomethacin, sulindac, apazone, pyrazolones, phenylbutazone, aspirin, COX-2 inhibitors (such as CELEBREX (celecoxib), PREXIGE (lumiracoxib)), metalloprotease inhibitors (preferably MMP-13 selective inhibitors), p2×7 inhibitors, $\alpha2\alpha$ inhibitors, NEUROTIN, pregabalin, low dose methotrexate, leflunomide, hydroxychloroquine, d-penicillamine, auranofin or parenteral or oral gold.

The invention provides in a further aspect a combination comprising a compound of formula (I), (IA), (IA'), (IB) and/or (IC) and a compound suitable for the treatment of osteoarthritis. Such compound may be selected from the group consisting of standard non-steroidal anti-inflammatory agents (hereinafter NSAID's) such as piroxicam, diclofenac, propionic acids such as naproxen, flurbiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, lumiracoxib and etoricoxib, analgesics and intraarticular therapies such as corticosteroids and hyaluronic acids such as hyalgan and synvisc.

The invention provides in a further aspect a combination comprising a compound of formula (I), (IA), (IA'), (IB) and/or (IC) and an antiviral agent and/or an antisepsis compound. Such antiviral agent may be selected from the group consisting of Viracept, AZT, acyclovir and famciclovir. Such antisepsis compound may be selected from the group consisting of Valant.

The invention provides in a further aspect a combination comprising a compound of formula (I), (IA), (IA'), (IB) and/or (IC) and one or more agents selected from the group consisting of CNS agents such as antidepressants (sertraline), anti-Parkinsonian drugs (such as deprenyl, L-dopa, Requip, Mirapex; MAOB inhibitors (such as selegine and rasagiline); comP inhibitors (such as Tasmar); A-2 inhibitors; dopamine reuptake inhibitors; NMDA antagonists; Nicotine agonists; Dopamine agonists; and inhibitors of neuronal nitric oxide synthase).

The invention provides in a further aspect a combination comprising a compound of formula (I), (IA), (IA'), (IB) and/or (IC) and one or more anti-Alzheimer's drugs. Such anti-Alzheimer Drug may be selected from the group consisting of donepezil, tacrine, $\alpha2\delta$inhibitors, NEUROTIN, pregabalin, COX-2 inhibitors, propentofylline or metryfonate.

The invention provides in a further aspect a combination comprising a compound of formula (I), (IA), (IA'), (IB) and/or (IC) and anosteoporosis agents and/or an immunosuppressant agent. Such osteoporosis agents ma be selected from the group consisting of EVISTA (raloxifene hydrochloride), droloxifene, lasofoxifene or fosomax. Such immunosuppressant agents may be selected from the group consisting of FK-506 and rapamycin.

In another aspect of the preferred embodiments, kits that include one or more compound of formula (I), (IA), (IA'), (IB) and/or (IC) and a combination partner as disclosed herein are provided. Representative kits include a PI3K inhibitor compound (e.g., a compound of formula (I), (IA), (IA'), (IB) and/or (IC)) and a package insert or other labeling including directions for treating a cellular proliferative disease by administering a PI3K inhibitory amount of the compound(s).

In general, the compounds of formula (I), (IA), (IA'), (IB) and/or (IC) will be administered in a therapeutically effective amount by any of the accepted modes of administration for agents that serve similar utilities. The actual amount of the compound of formula (I), (IA), (IA'), (IB) and/or (IC), i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day. All of these factors are within the skill of the attending clinician. Therapeutically effective amounts of compounds of formulas I may range from about 0.05 to about 50 mg per kilogram body weight of the recipient per day; preferably about 0.1-25 mg/kg/day, more preferably from about 0.5 to 10 mg/kg/day. Thus, for administration to a 70 kg person, the dosage range would most preferably be about 35-70 mg per day.

In general, compounds of formula (I), (IA), (IA'), (IB) and/or (IC) will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of the formula I is inhalation. This is an effective method for delivering a therapeutic agent directly to the respiratory tract.

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory airstream during breathing by the device. In order to achieve a free flowing powder, the therapeutic agent is formulated with an excipient such as lactose. A measured amount of the therapeutic agent is stored in a capsule form and is dispensed with each actuation.

The inventions also relates to formulations wherein the particle size of a compound of formula I between 10-1000 nm, preferably 10-400 nm. Such pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability. Both documents are included by reference.

In a further aspect, the invention provides pharmaceutical compositions comprising a (therapeutically effective amount) of a compound of formula (I), (IA), (IA'), (IB) and/or (IC), and at least one pharmaceutically acceptable excipient. Acceptable excipients are non-toxic, aid administration, and do not adversely affect the therapeutic benefit of the compound of formula (I), (IA), (IA'), (IB) and/or (IC). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like.

Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of the formula I in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01-99.99 wt % of a compound of formula I based on the total formulation, with the balance being one or more suitable pharmaceutical excipients. Preferably, the compound is present at a level of about 1-80 wt %.

The invention further relates to pharmaceutical compositions comprising (i.e. containing or consisting of) at least one compound of formula (I), (IA), (IA'), (IB) and/or (IC) and at least one pharmaceutically acceptable excipient.

Pharmaceutical compositions comprising a compound of formula (I), (IA), (IA'), (IB) and/or (IC) in free form or in pharmaceutically acceptable salt form in association with at least one pharmaceutical acceptable excipient (such as a carrier and/or diluent) may be manufactured in conventional manner by mixing the components.

Combined pharmaceutical compositions comprising a compound of formula (I), (IA), (IA'), (IB) and/or (IC) in free form or in pharmaceutically acceptable salt form and further comprising a combination partner (either in one dosage unit form or as a kit of parts) in association with at least one pharmaceutical acceptable carrier and/or diluent may be manufactured in conventional manner by mixing with a pharmaceutically acceptable carrier and/or diluent with said active ingredients.

Consequently, the invention provides in further aspects
 a combined pharmaceutical composition, e.g. for use in any of the methods described herein, comprising a compound of formula (I), (IA), (IA'), (IB) and/or (IC) in free form or pharmaceutically acceptable salt form in association with a pharmaceutically acceptable diluent and/or carrier.
 a combined pharmaceutical composition comprising a compound of formula (I), (IA), (IA'), (IB) and/or (IC) in free form or in pharmaceutically acceptable salt form as active ingredient; one or more pharmaceutically acceptable carrier material(s) and/or diluents and optionally one or more further drug substances. Such combined pharmaceutical composition may be in the form of one dosage unit form or as a kit of parts.
 a combined pharmaceutical composition comprising a therapeutically effective amount of a compound of formula (I), (IA), (IA'), (IB) and/or (IC) in free form or in pharmaceutically acceptable salt form and a second drug substance, for simultaneous or sequential administration.
 a method as defined above comprising co-administration, e.g. concomitantly or in sequence, of a therapeutically effective non-toxic amount of a compound of formula (I), (IA), (IA'), (IB) and/or (IC) or a pharmaceutically acceptable salt thereof, and at least a second drug substance, e.g. as indicated above.
 a pharmaceutical combination, e.g. a kit, comprising a) a first agent which is a compound of formula (I), (IA), (IA'), (IB) and/or (IC) as disclosed herein, in free form or in pharmaceutically acceptable salt form, and b) at least one co-agent, e.g. as indicated above; whereby such kit may comprise instructions for its administration.

The following examples of compounds formula (I), (IA), (IA'), (IB) and/or (IC) illustrate the invention without limiting the scope thereof. Methods for preparing such compounds are described.

Temperatures are measured in degrees Celsius. Unless otherwise indicated, the reactions take place at rt and the MS are obtained with ESI. The following HPLC/MS methods are used in the preparation and analysis of the Intermediates and Examples:

Methods A1 to A3 (LCMS: analytical HPLC/MS):
System: Agilent 1100 Series with Waters Micromass ZQ 2000 ESI+ and/or ESI−
Column: XBridge C18, 3×30 mm, 2.5 micron
Temperature: 50° C.
Eluent A: $H_2O$, containing 5% $CH_3CN$ and 0.8% HCOOH
Eluent B: $CH_3CN$, containing 0.6% HCOOH
Flow Rate: 1.2-2.4 mL/min
Method A1: method Polar4a_p__100-900 and method Polar4a_pn__100-900:
Gradient: 0-2.9 min: 1% to 95% of B
Method A2: method Fast4_p__100-900 and method Fast4a_pn__100-900:

Gradient: 0-2.4 min: 10% to 95% of B
Method A3: method Slow4a_pn__100-900:
Gradient: 0-4.4 min: 5% to 95% of B
Method B (preparative HPLC) Instrument: Waters preparative HPLC system, column: Sunfire™ Prep C18 OBD™ 5 micron 30×100 mm, temperature: 25° C., eluent: gradient from 5-100% $CH_3CN$ in 0.05% aqueous TFA over 20 minutes, flow rate: 30 ml/minute, detection: UV 254 nm.

Method C (preparative HPLC) Instrument: Waters preparative HPLC system, column: Sunfire™ Prep C18 OBD™ 5 micron 30×100 mm, temperature: 25° C., eluent: gradient from 5-50% $CH_3CN$ in 0.05% aqueous TFA over 20 minutes, flow rate: 30 ml/minute, detection: UV 254 nm.

Method D (Analytical HPLC): Linear gradient 2-100% $CH_3CN$ (0.1% TFA) and $H_2O$ (0.1% TFA) in 5 min+1.5 min 100% $CH_3CN$ (0.1% TFA); detection at 215 nm, flow rate 1 mL/min at 30° C. Column: Nucleosil 100-3 C18 (70×4 mm)

Method E (preparative HPLC/MS) Instrument: Gilson preparative HPLC system, column: Sunfire™ Prep C18 OBD™ 5 micron 30×100 mm, temperature: 25° C., eluent: gradient from 5-100% $CH_3CN$ in 0.05% aqueous TFA over 20 minutes, flow rate: 30 ml/minute, detection: UV 254 nm.

Method F (Analytical HPLC) Instrument: Shimadzu SIL-10A, Method: Linear gradient 2-100% $CH_3CN$ (0.1% TFA) and $H_2O$ (0.1% TFA) in 4 min+2 min 100% $CH_3CN$ (0.1% TFA); back to –100% $CH_3CN$ (0.1% TFA) in 3 min.; detection at 215 nm, flow rate 2 mL/min at RT.
Column: Nucleosil OD-5-100 C18 (150×4.6 mm)

Method G (Analytical HPLC) Instrument:
System: Agilent 1100 Series
Column: HP Hypersil BDS C18, 4×125 mm, 5 micron
Temperature: 25° C.
Eluent A: $H_2O$, containing 0.1% v/v TFA
Eluent B: $CH_3CN$, containing 0.1% v/v TFA
Gradient: 10%→100% B in 5 min, 2.5 min with 100% B, then→10% B in 1 min
Flow Rate: 1.5 mL/min
Detection: UV 215 nm Method H (Analytical HPLC) Instrument:
System: Agilent 1100 Series
Column: Macherey-Nagel Nucleosil 100-3 C18HD, 4×125 mm, 3 micron
Temperature: 30° C.
Eluent A: $H_2O$, containing 0.1% v/v TFA
Eluent B: $CH_3CN$, containing 0.1% v/v TFA
Gradient: 2%→100% B in 7 min, 2 min with 100% B, then→2% B in 1 min
Flow Rate: 1.0 mL/min
Detection: UV 215 nm Method I (LCMS: analytical HPLC/MS):
System: Waters Acquity UPLC with Waters Micromass ZQ 2000 ESI+/−
Column: Acquity HSS T3 C18, 2.1×50 mm, 1.8 micron
Temperature: 50° C.
Eluent A: $H_2O$, containing 0.05% v/v HCOOH and 3.75 mM ammonium acetate
Eluent B: $CH_3CN$, containing 0.04% HCOOH
Gradient: 2%→98% B in 4.3 min, 0.7 min with 98% B, then→2% B in 0.1 min and 0.9 min with 2% B
Flow Rate: 1.0 mL/min Method J (LCMS: analytical HPLC/MS):
System: Agilent 1100 Series; MS: G1946D
Column: Symmetry C8, 2.1×50 mm, 3.5 micron
Eluent A: $H_2O$, containing 0.1% v/v HCOOH
Eluent B: $CH_3CN$, containing 0.1% v/v HCOOH
Gradient: 0-3.3 min: 5% to 95% of B
Flow Rate: 1.0 mL/min Method K (LCMS: analytical HPLC/MS):
System: Waters Acquity UPLC
Column: Acquity HSS T3 C18, 2.1×50 mm, 1.8 micron
Eluent A: $H_2O$, containing 0.05% v/v HCOOH and 0.05% ammonium acetate
Eluent B: acetonitrile, containing 0.04% HCOOH
Gradient: 2%→98% B in 1.7 min, 0.45 min with 98% B, then→2% B in 0.04 min
Flow Rate: 1.2 ml/min Method L (LCMS: analytical HPLC/MS):
System: Waters Aquity UPLC; MS: Waters AQ Detector
Column: Aquity HSS, 1.8 μm 2.1×50 mm, 3/pk
Eluent A: $H_2O$, containing 0.1% v/v HCOOH
Eluent B: $CH_3CN$, containing 0.1% v/v HCOOH
Gradient: 0-1.5 min: 10% to 95% of B, then 1 min: 95% B
Flow Rate: 1.2 mL/min ESI-MS:
Instrument: Micromass Platform II
Eluent: 15% v/v MeOH in $H_2O$ containing 0.2% v/v of a 25% ammonium hydroxide solution
Flow Rate: 0.05 mL/min In the following examples, the abbreviations given below are used:
atm. atmosphere
CDI 1,1'-carbonyldiimidazole
$CH_3CN$ acetonitrile
DAST diethylaminosulfur trifluoride
DCE 1,2-dichloroethane
DCM dichloromethane
DMF N,N-dimethylformamide
DMSO dimethyl sulfoxide
$Et_2O$ diethyl ether
EtOAc ethyl acetate
EtOH ethanol
eq equivalent(s)
h hour(s)
$H_2O$ water
HPLC High Performance Liquid Chromatography
HV high vacuum
LCMS liquid chromatography coupled with mass spectrometry
LiHMDS lithium bis(trimethylsilyl)amide
MeOH methanol
mL milliliter(s)
min minute(s)
MS-ESI electrospray ionisation mass spectrometry
MW microwave
$NaHCO_3$ sodium bicarbonate
$Na_2SO_4$ sodium sulfate
$NH_4Cl$ ammonium chloride
RM reaction mixture
$R_f$ ratio of fronts in TLC
rt room temperature
TEA triethylamine
TFA trifluoroacetic acid
THF tetrahydrofuran
TLC thin layer chromatography
$t_R$ retention time
UV Ultraviolet

Intermediate A: Imidazole-1-carboxylic acid (8-tert-butyl-4,5-dihydro-thiazolo[4,5-h]quinazolin-2-yl)-amide

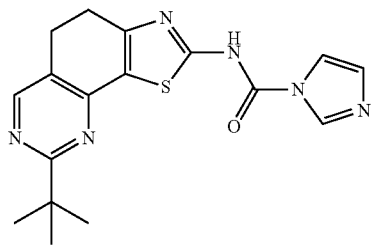 [SMILES: CC(C)(C)c1ncc2c(n1)-c1sc(NC(=O)n3ccnc3)nc1CC2]

8-tert-Butyl-4,5-dihydro-thiazolo[4,5-h]quinazolin-2-ylamine (Stage A.1, 0.319 g, 1.225 mmol) and CDI (278 mg, 1.715 mmol) were added to DCM (5 ml) and DMF (0.25 ml) under an argon atm. After 18 h the residue was cooled to 4° C. and the precipitate was collected by filtration. The solid was dried at 50° C. in high vacuo to give the title compound as a pale yellow solid. LCMS: $t_R$ 0.95 min and M+H 319.0 (method A2) for (8-tert-butyl-4,5-dihydro-thiazolo[4,5-h]quinazolin-2-yl)-carbamic acid methyl ester; the product of the reaction of the title compound with MeOH during the preparation of the sample as MeOH solution.

Stage A.1: 8-tert-Butyl-4,5-dihydro-thiazolo[4,5-h]quinazolin-2-ylamine

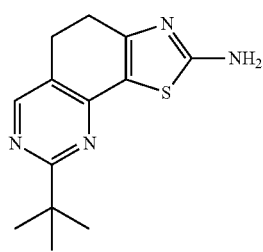 [SMILES: CC(C)(C)c1ncc2c(n1)-c1sc(N)nc1CC2]

Intermediate A.1 was obtained by two different routes. Both routes start from 2-amino-5,6-dihydro-4H-benzothiazol-7-one and described below:

Route 1:

To a mixture of N'-{6-[1-dimethylamino-meth-(E)-ylidene]-7-oxo-4,5,6,7-tetrahydro-benzothiazol-2-yl}-N,N-dimethyl-formamidine (Stage A.2, 2.2 g, 7.90 mmol) in 2-methoxyethanol (20 mL) was added at rt sodium hydroxide (1.185 g, 29.6 mmol) and 2,2-dimethyl-propionamidine hydrochloride (1.620 g, 11.85 mmol). The RM was stirred at 125° C. for 3 h. After cooling to rt, the RM was diluted with MeOH, adsorbed onto silica gel and purified by flash chromatography (CombiFlash® Companion system®, with RediSep® silica gel column, eluent: DCM/MeOH/Ammonia 95:5:0.5). LC: $t_R$ 3.64 min (method D). MS: M+H=261. 1H-NMR in DMSO-$d_6$: 8.24 (s, 1H); 7.70 (s, 2H); 2.89-2.84 (m, 2H); 2.76-2.71 (m, 2H); 1.28 (s, 9H).

Stage A.2: N'-{6-[1-Dimethylamino-meth-(E)-ylidene]-7-oxo-4,5,6,7-tetrahydro-benzothiazol-2-yl}-N,N-dimethyl-formamidine

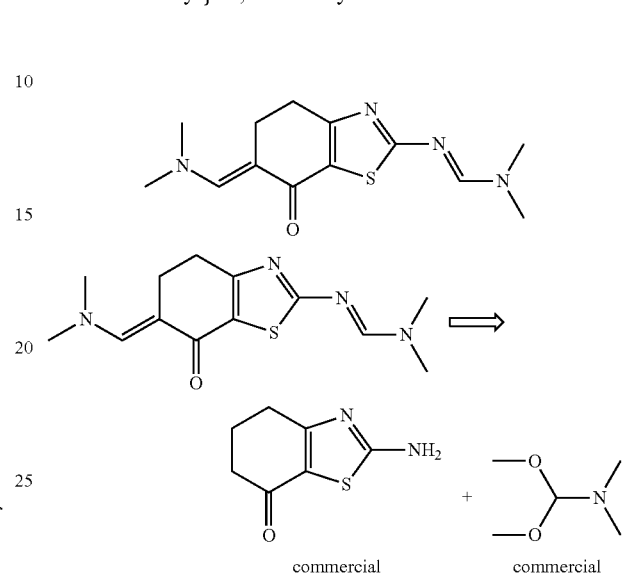

A suspension of 2-amino-5,6-dihydro-4H-benzothiazol-7-one (3.5 g, 20.81 mmol) in dimethoxymethyldimethylamine (12 mL, 90 mmol) was heated at 100° C. with stirring for 65 h. The RM was then evaporated to dryness in vacuo and the residue was suspended in EtOAc. After 1 h at 4° C., the solid was filtered off, washed with EtOAc and then dried under high vacuum at 60° C. to give the pure title product as brown crystals. LC: $t_R$ 3.25 min (method D). MS: M+H=279. $^1$H-NMR in DMSO-$d_6$: 8.40 (s, 1H); 7.23 (s, 1H); 3.15 (s, 3H); 3.05 (s, 6H); 2.97 (s, 3H); 2.91 (t, 2H); 2.67 (t, 2H).

Route 2:

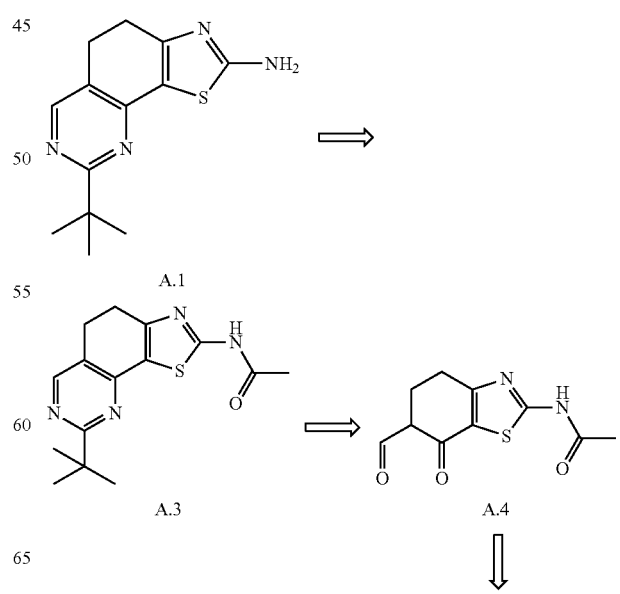

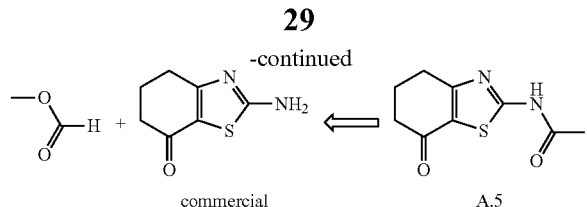

commercial          A.5

Potassium carbonate (0.434 g, 3.14 mmol) was added to a mixture of N-(8-tert-butyl-4,5-dihydro-thiazolo[4,5-h]quinazolin-2-yl)-acetamide (Stage A.3, 0.38 g, 1.257 mmol) in MeOH. The RM was stirred at 50° C. for 52 h, then cooled to rt and evaporated in vacuo to give a red mass. Water (20 mL) was added and the mixture was stirred at it for a further 3 h. The red suspension was then cooled down to 4° C. and filtered to give after drying under high vacuum the title compound as a beige solid. LCMS: $t_R$ 0.99 min and M+H=261 (method A3). $^1$H-NMR in DMSO-$d_6$, 400 MHz: 8.24 (s, 1H); 7.70 (s, 2H); 2.89-2.84 (m, 2H); 2.76-2.71 (m, 2H); 1.28 (s, 9H).

Stage A.3: N-(8-tert-butyl-4,5-dihydro-thiazolo[4,5-h]quinazolin-2-yl)-acetamide

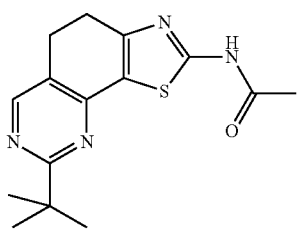 [SMILES: CC(=O)Nc1nc2c(s1)-c1nc(C(C)(C)C)ncc1CC2]

Pyridine (13 mL) was added to N-(6-formyl-7-oxo-4,5,6,7-tetrahydro-benzothiazol-2-yl)-acetamide (Stage A.4, 3.05 g, 12.8 mmol) and tert.butylamidine hydrochloride (1.788 g, 12.8 mmol) and the mixture was heated in a sealed vessel at 160° C. for 6.5 h. After cooling the reaction mixture was filtered to give a solid. The filtration mother liquor was evaporated to give further solid material. The combined solids were triturated repeatedly with hot CH$_3$CN and the CH$_3$CN mother liquors evaporated to give a solid which was shown to be predominantly the title product. The crude product was dissolved in ca. 10 ml of a 10% DMSO in MeOH to give a slightly hazy orange solution which was filtered and added dropwise to water (100 ml) at it with stirring. The precipitate solid was collected by filtration to give the title compound as an orange solid. LCMS: $t_R$ 1.37 min and M+H=303.0 (method A3). $^1$H-NMR in DMSO-$d_6$, 400 MHz: 12.40 (s, 1H); 8.44 (s, 1H); 2.88-3.00 (m, 4H); 2.17 (s, 3H); 1.32 (s, 9H).

Stage A.4: N-(6-Formyl-7-oxo-4,5,6,7-tetrahydro-benzothiazol-2-yl)-acetamide

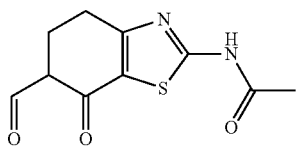 [SMILES: CC(=O)Nc1nc2c(s1)C(=O)C(C=O)CC2]

LiHMDS solution (1 M, 27.7 mL) was added over 10 min to a suspension of N-(7-oxo-4,5,6,7-tetrahydro-benzothiazol-2-yl)-acetamide (Stage A.5, 2.0 g, 9.23 mmol) in dry THF (20 mL) cooled at −78° C. under an argon atm. The RM was then stirred at −78° C. for 2.5 h and methyl formate (2.308 mL, 36.9 mmol) added dropwise over 30 min. The RM was then warmed slowly to rt and was then stirred 18 h at rt. The RM was drown out into aqueous 1 M HCl (70 mL) and extracted 3× with DCM, dried over Na$_2$SO$_4$ and evaporated to give a the title compound as a solid. HPLC: $t_R$ 3.65 min (method D). MS: M−H=237. $^1$H-NMR in DMSO-$d_6$ (400 MHz): 12.50 (s, br, 1H); 7.55 (s, 1H); 2.90-2.60 (m, 4H); 2.15 (s, 3H).

Stage A.5: N-(7-Oxo-4,5,6,7-tetrahydro-benzothiazol-2-yl)-acetamide

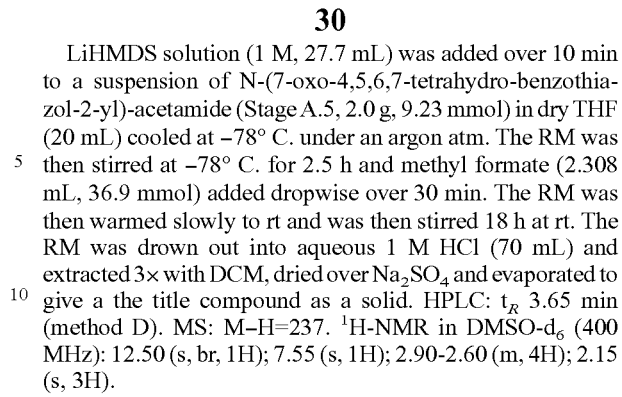

To acetic anhydride (80 mL) was added at rt 2-amino-5,6-dihydro-4H-benzothiazol-7-one (10 g, 59.4 mmol) and the resulting suspension was heated to reflux. After 1.75 h stirring at reflux, the RM was allowed to cool with stirring and stirred for 18 h at it before further cooling with an ice/NaCl bath, and a solid was collected by filtration. The solid was then triturated twice with refluxing acetone (10 mL then 15 mL) before filtering and drying under vacuum at 40° C. to give the title product as a beige solid. HPLC: $t_R$ 3.47 min (method D). MS: M−H=211.1. $^1$H-NMR in DMSO-$d_6$ (600 MHz): 12.55 (s, br, 1H); 2.84 (t, 2H); 2.48 (t, 2H); 2.17 (s, 3H); 2.065 (qt, 2H).

Intermediate B:
(2S,4R)-4-Dimethylamino-pyrrolidine-2-carboxylic acid amide

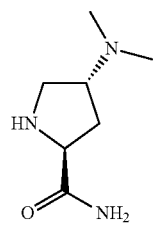

A solution of (2S,4R)-4-dimethylamino-pyrrolidine-2-carboxylic acid methyl ester (Stage B.1, 225 mg) and 7 M ammonia in MeOH (7 mL) was stood for 18 h at it in a sealed vessel. Evaporation and trituration with Et$_2$O gave the title compound as a white solid.

Stage B.1
(2S,4R)-4-Dimethylamino-pyrrolidine-2-carboxylic acid methyl ester

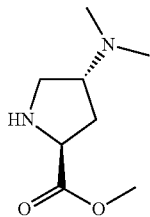

A mixture of (2S,4R)-4-dimethylamino-pyrrolidine-1,2-dicarboxylic acid 1-benzyl ester 2-methyl ester (Stage B.2, 420 mg), 10% palladium on carbon (80 mg) and MeOH (10 mL) was stirred for 16 h under an atm. of hydrogen. Filtration and evaporation gave the title compound which was used without purification in the following steps.

Stage B.2 (2S,4R)-4-Dimethylamino-pyrrolidine-1,2-dicarboxylic acid 1-benzyl ester 2-methyl ester

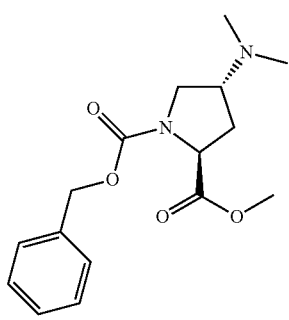 [SMILES: COC(=O)[C@@H]1C[C@@H](N(C)C)CN1C(=O)OCc1ccccc1]

Sodium cyanoborohydride (200 mg) was added to a mixture of (2S,4R)-4-amino-pyrrolidine-1,2-dicarboxylic acid 1-benzyl ester 2-methyl ester (400 mg), formalin (0.68 ml), acetic acid (0.72 ml), triethylamine (0.2 ml) and MeOH (2 ml) and the mixture was stirred for 2 h at rt. The RM was then partitioned between DCM and aqueous NaHCO₃ solution, the DCM layers evaporated and purified by normal phase chromatography, eluent; gradient from EtOAc to 20% EtOH in EtOAc, to give the predominant UV-active component. The chromatographied material was taken up with 1 M HCl, washed 2× with Et₂O, the aqueous layer basified with NaHCO₃, 3× extracted with Et₂O, dried over Na₂SO₄ and evaporated to give the title compound as a pale yellow oil.

Intermediate C: Imidazole-1-carboxylic acid (8-diethylamino-4,5-dihydro-thiazolo[4,5-h]quinazolin-2-yl)-amide

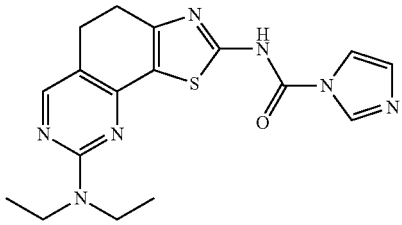 [SMILES: CCN(CC)c1ncc2c(n1)-c1sc(NC(=O)n3ccnc3)nc1CC2]

To a mixture of 2-amino-8-N,N-diethylamino-4,5-dihydrothiazolo[4,5-h]quinazoline (Stage C.1, 1 g, 3.63 mmol) in DCM (35 mL) was added CDI (1.178 g, 7.26 mmol). The RM was stirred at 40° C. for 90 h. After cooling to rt, the solid was collected by filtration to give the title compound. HPLC: $t_R$ 4.11 min (method D). MS: M+H=334 for (8-diethylamino-4,5-dihydro-thiazolo[4,5-h]quinazolin-2-yl)-carbamic acid methyl ester as the product of the reaction of the title compound with MeOH.

Stage C.1: 2-Amino-8-diethylamino-4,5-dihydrothiazolo[4,5-h]quinazoline

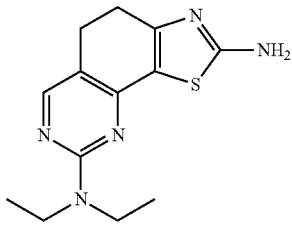 [SMILES: CCN(CC)c1ncc2c(n1)-c1sc(N)nc1CC2]

To N'-{6-[1-dimethylamino-meth-(E)-ylidene]-7-oxo-4,5,6,7-tetrahydro-benzothiazol-2-yl}-N,N-dimethyl-formamidine (Stage A.2, 1 g, 3.59 mmol) in 2-methoxyethanol (10 mL) was added NaOH (0.539 g, 13.47 mmol) and N,N-diethylguanidine (0.454 g, 3.94 mmol) under argon at rt. The RM was stirred for 3.5 h at 125° C. and then cooled to rt. After evaporation in vacuo the residue was dissolved in 0.1 M HCl (50 mL) and washed with EtOAc. The aqueous layer was then basified with 6 N NaOH and extracted 3× with EtOAc. the organic layers were dried over Na₂SO₄, evaporated and dried under high vacuum at 60° C. to give the title compound as orange crystals. LC: $t_R$ 3.60 min (method D). MS: M+H=276.

1H-NMR in DMSO-d6: 7.91 (s, 1H); 7.59 (s, 2H); 3.50 (q, 4H); 2.69 (dd, 4H); 1.07 (t, 6H).

Intermediate D: (2S,3S)-3-Methyl-pyrrolidine-2-carboxylic acid amide

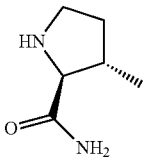

A 4 M solution of HCl in 1,4-dioxan (1.5 mL) was added to a suspension of (2S,3S)-3-methylpyrrolidine-2-carboxylic acid (0.5 g) in EtOH (5 mL) at rt and the mixture heated at reflux for 20 h. The RM was evaporated and a 7 M solution of ammonia in MeOH (5.6 mL) added. The RM was stood at it for 6 days then evaporated, the residue triturated with MeOH (0.5 mL) and filtered and washed with cold MeOH (2 mL) to give the title compound as a white solid. $^1$H-NMR (d$_6$-DMSO, 400 MHz): 8.06 (s, 1H), 7.67 (s, 1H), 3.60 (d, 1H), 3.25-3.14 (m, 2H), 2.24-2.15 (m, 1H), 2.09-1.98 (m, 1H), 1.57-1.45 (m, 1H), 1.13 (d, 3H).

Intermediate E: (R)-2-Benzyl-pyrrolidine-2-carboxylic acid amide

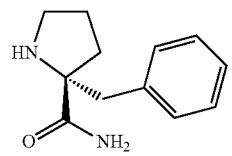 [SMILES: NC(=O)[C@]1(Cc2ccccc2)CCCN1]

A mixture of (3R,7aR)-7a-benzyl-3-trichloromethyl-tetrahydro-pyrrolo[1,2-c]oxazol-1one (1.40 g, prepared as described by Wang and Germanas *Synlett* 1999, 33-36.) and 7 M ammonia in MeOH (15 ml) was heated at 50° C. for 3 days in a sealed vessel. The cooled RM was then evaporated and triturated with chloroform to give the title compound as a white solid.

Intermediate F: (S)-2-Methyl-pyrrolidine-2-carboxylic acid amide

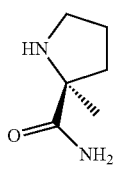

A solution of (S)-2-methyl-pyrrolidine-2-carboxylic acid butyl ester (Stage F.1, 2.3 g) in a 7 M solution of ammonia in MeOH (22.2 ml) was heated in a bomb at 70° C. for 10 days. Evaporation of the RM and trituration with hexanes (20 mL) gave the title compound as an off-white solid. $^1$H-NMR (d$_6$-DMSO, 400 MHz): 7.40 (s, 1H), 6.89 (s, 1H), 2.95-2.84 (m, 1H), 2.72-2.60 (m, 1H), 2.06-1.95 (m, 1H), 1.66-1.44 (m, 2H), 1.42-1.30 (m, 1H), 1.22 (s, 3H).

Stage F.1: (S)-2-Methyl-pyrrolidine-2-carboxylic acid butyl ester

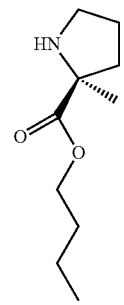

Concentrated HCl (2 ml) was added to a suspension of (S)-2-methyl-pyrrolidine-2-carboxylic acid (2 g) in butan-1-ol (50 ml) which was heated at 60° C. for 18 h then at reflux for 4 days. The RM was evaporated, partitioned between saturated aqueous NaHCO$_3$ and DCM, extracted 3× with DCM, dried over Na$_2$SO$_4$ and evaporated. The isolated oil was then kugelrohr distilled at 10 mbar to give the title compound as a clear colorless oil from the fraction distilling at an oven temperature of 100-120° C.

Intermediate G: (R)-2-Methoxymethyl-pyrrolidine-2-carboxylic acid amide

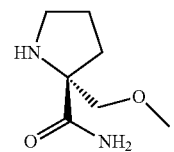

A mixture of (3R,7aR)-7a-methoxymethyl-3-trichloromethyl-tetrahydro-pyrrolo[1,2-c]oxazol-1-one (Stage G.1, 0.6 g) and 7 M ammonia in MeOH (6 mL) was stood at rt for 2 days in a sealed vessel. The RM was then evaporated to give the title compound as a pale yellow oil which was used without further purification.

Stage G.1: (3R,7aR)-7a-Methoxymethyl-3-trichloromethyl-tetrahydro-pyrrolo[1,2-c]oxazol-1-one

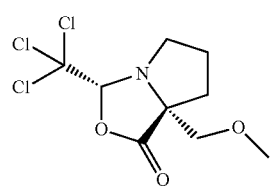 [SMILES: COC[C@@]12CCCN1[C@@H](C(Cl)(Cl)Cl)OC2=O]

A 1M of solution of lithium diisopropylamide in a 3:5 mixture of hexanes/THF (8.25 ml) was added dropwise to (3R,7aS)-3-trichloromethyl-tetrahydro-pyrrolo[1,2-c]oxazol-1-one (1.51 g, prepared as described by Wang and Germanas *Synlett* 1999, 33-36.) in THF (5 ml) at −78° C. After stirring 30 minutes at −78° C. methoxymethylchloride (1.14 ml) was added. The RM was then allowed to warm to −30° C. over 3 h and water was added. The aqueous layer was extracted with DCM, the combined organic layers evaporated and the residue was then purified by normal phase chromatography, eluting with DCM, to give the title compound as a pale yellow oil.

Intermediate H:
(R)-2-Dimethylaminomethyl-pyrrolidine-2-carboxylic acid amide

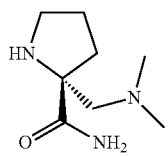

A mixture of (3R,7aR)-7a-dimethylaminomethyl-3-trichloromethyl-tetrahydro-pyrrolo[1,2-c]oxazol-1-one (Stage H.1, 0.26 g) and 7 M ammonia in MeOH (4 mL) was heated at 50° C. for 3 days in a sealed vessel. The cooled RM was then evaporated to give the title compound as a brown oil which was used without further purification. MS: M+H=172.1.

Stage H.1: (3R,7aR)-7a-Dimethylaminomethyl-3-trichloromethyl-tetrahydro-pyrrolo[1,2-c]oxazol-1-one

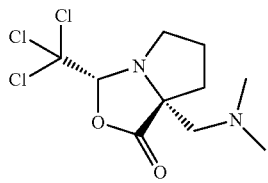 [SMILES: CN(C)C[C@@]12CCCN1[C@@H](C(Cl)(Cl)Cl)OC2=O]

A 1 M of solution of lithium diisopropylamide in a 3:5 mixture of hexanes/THF (8.25 ml) was added dropwise to (3R,7aS)-3-trichloromethyl-tetrahydro-pyrrolo[1,2-c]oxazol-1-one (1.51 g, prepared as described by Wang and Germanas *Synlett* 1999, 33-36.) in THF (5 ml) at −78° C. After stirring 30 minutes at −78° C. Eschenmoser's salt (2.78 g) was added. The RM was then allowed to warm to −40° C. with vigorous stirring over 1 h and maintained for 2 h at −40° C. Water was then added and the aqueous layer extracted with DCM, the combined organic layers dried over $Na_2SO_4$ and evaporated. The residue was then purified by normal phase chromatography eluting with a gradient from DCM to 20% EtOAc in DCM to give the title compound as a pale yellow oil (M+H=301/303/305 3:3:1).

Intermediate I: $d_6$-(R)-2-Dimethylaminomethyl-pyrrolidine-2-carboxylic acid amide

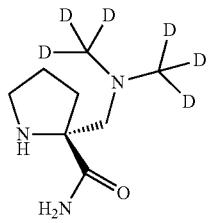 [SMILES: [2H]C([2H])([2H])N(C[C@@]1(C(N)=O)CCCN1)C([2H])([2H])[2H]]

$d_6$-(3R,7aR)-7a-Dimethylaminomethyl-3-trichloromethyl-tetrahydro-pyrrolo[1,2-c]oxazol-1-one (Stage I.1, 440 mg, 1.430 mmol) was dissolved in ammonia in MeOH (10.2 mL, 71.4 mmol) in a sealed vessel and heated at 75° C. for 5 days. The reaction mixture was evaporated and triturated 2× with $CHCl_3$ to give the title product as a pale brown solid.

Stage I.1: $d_6$-(3R,7aR)-7a-Dimethylaminomethyl-3-trichloromethyl-tetrahydro-pyrrolo[1,2-c]oxazol-1-one

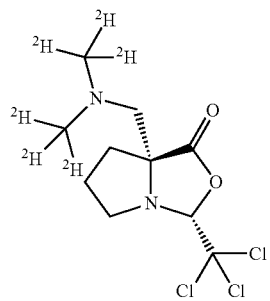 [SMILES: [2H]C([2H])([2H])N(C[C@@]12CCCN1[C@@H](C(Cl)(Cl)Cl)OC2=O)C([2H])([2H])[2H]]

(3R,7aR)-1-Oxo-3-trichloromethyl-dihydro-pyrrolo[1,2-c]oxazole-7a-carbaldehyde (obtained as described in *J. Org. Chem.* 2006, 71(1), 97-102, 1 g, 3.67 mmol), dimethylamine-$d_7$ in THF (1.0 mL, 14.09 mmol), acetic acid (0.525 mL, 9.17 mmol) and DCE (4 mL) were combined under argon and sodium triacetoxyborohydride (1.089 g, 5.14 mmol) was added portionwise. After stirring at it for 3 h the RM was taken up in DCM, and partitioned with 1 M NaOH extracting once more with DCM. The organic layers were combined then washed twice with water before being dried over $Na_2SO_4$. The solution was evaporated to half of its volume and 1 M HCl in $H_2O$ was added, the layers separated and the aqueous layer washed twice with DCM. The pH of the aqueous layers were adjusted to ~8 with saturated $Na_2CO_3$ solution and extracted three times with DCM. The organic layers were dried over $Na_2SO_4$ and evaporated, to give the desired title product as a pale yellow oil.

Intermediate J: (R)-2-Hydroxymethyl-pyrrolidine-2-carboxylic acid amide

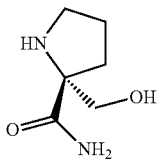

(3R,7aR)-7a-Hydroxymethyl-3-trichloromethyl-tetrahydro-pyrrolo[1,2-c]oxazol-1-one (Stage J.1, 308 mg, 1.122 mmol) was added to 7 M ammonia in MeOH (8.014 mL, 56.1 mmol) under argon and heated at 75° C. in a sealed vessel for 72 h and then evaporated to give the title compound as a viscous pale brown oil which was used without further purification.

Stage J.1: (3R,7aR)-7a-Hydroxymethyl-3-trichloromethyl-tetrahydro-pyrrolo[1,2-c]oxazol-1-one

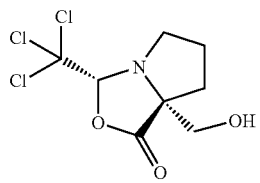 [SMILES: O=C1O[C@H](C(Cl)(Cl)Cl)N2CCC[C@@]12CO]

Sodium triacetoxyborohydride (544 mg, 2.57 mmol) was added to (3R,7aR)-1-oxo-3-trichloromethyl-dihydro-pyrrolo[1,2-c]oxazole-7a-carbaldehyde (obtained as described in *J. Org. Chem.* 2006, 71(1), 97-102, 500 mg, 1.835 mmol) in DCE (4 mL). The RM was stirred 18 h at rt then taken up in DCM, the organic layer washed with water, dried over Na$_2$SO$_4$ and evaporated. The crude product was purified using a 20 g RediSep® silica gel column (eluent DCM to 10% MeOH in DCM) to give the title compound as a clear pale yellow oil.

Intermediate K: (R)-2-{[(3-Fluoro-benzyl)-methyl-amino]-methyl}-pyrrolidine-2-carboxylic acid amide

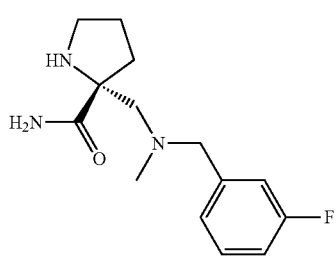 [SMILES: CN(Cc1cccc(F)c1)C[C@@]1(C(N)=O)CCCN1]

(3R,7aR)-7a-{[(3-Fluoro-benzyl)-methyl-amino]-methyl}-3-trichloromethyl-tetrahydro-pyrrolo[1,2-c]oxazol-1-one (Stage K.1, 385 mg, 0.973 mmol) was added to 7 M ammonia in MeOH (6.950 mL, 48.7 mmol) under argon and heated in a sealed vessel at 50° C. for 6 days and then at 75° C. for 5 days. The RM was then evaporated and the residue purified by flash chromatography using a 12 g RediSep® silica gel column (eluent 5% MeOH in DCM) to give the title compound as a yellow oil.

Stage K.1: (3R,7aR)-7a-{[(3-Fluoro-benzyl)-methyl-amino]-methyl}-3-trichloromethyl-tetrahydro-pyrrolo[1,2-c]oxazol-1-one

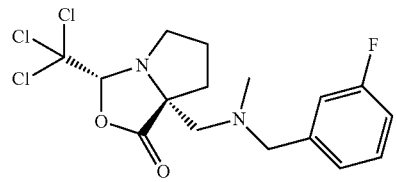 [SMILES: CN(Cc1cccc(F)c1)C[C@@]12CCCN1[C@@H](C(Cl)(Cl)Cl)OC2=O]

Sodium triacetoxyborohydride (889 mg, 4.19 mmol) was added to a mixture of (3R,7aR)-7a-[(3-fluoro-benzylamino)-methyl]-3-trichloromethyl-tetrahydro-pyrrolo[1,2-c]oxazol-1-one (Stage K.2, 400 mg, 1.048 mmol), formaldehyde (37% in H$_2$O, 0.102 mL, 1.36 mmol) and acetic acid (0.150 mL, 2.62 mmol) in DCE (4 mL) under an argon atm. After 2 h stirring at rt the RM was partitioned between DCM and water. The combined organic layers were dried over Na$_2$SO$_4$ and evaporated to give the title compound as a pale brown oil which was used without further purification.

Stage K.2: (3R,7aR)-7a-[(3-Fluoro-benzylamino)-methyl]-3-trichloromethyl-tetrahydro-pyrrolo[1,2-c]oxazol-1-one

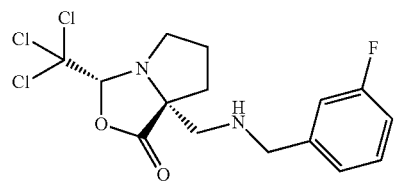 [SMILES: O=C1O[C@H](C(Cl)(Cl)Cl)N2CCC[C@@]12CNCc1cccc(F)c1]

Sodium triacetoxyborohydride (544 mg, 2.57 mmol) was added to (3R,7aR)-1-oxo-3-trichloromethyl-dihydro-pyrrolo[1,2-c]oxazole-7a-carbaldehyde (obtained as described in *J. Org. Chem.* 2006, 71(1), 97-102, 500 mg, 1.835 mmol), 3-fluorobenzylamine (0.251 mL, 2.20 mmol) and acetic acid (0.263 mL, 4.59 mmol) in DCE (4 mL) under an argon atm. The RM was stirred at rt for 3 h, then partitioned between water and DCM, the combined organic dried over Na$_2$SO$_4$ and evaporated to give the title compound as a pale yellow oil which was used without further purification.

Intermediate L: (S)-Azetidine-2-carboxylic acid amide

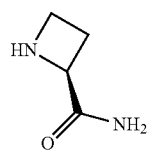

A mixture of (S)-2-carbamoyl-azetidine-1-carboxylic acid benzyl ester (Stage L.1, 1.8 g) and 10% palladium on carbon (0.2 g) in MeOH (25 ml) was stirred under a hydrogen atm. at rt for 5 h. Filtration and evaporation gave the title compound which was used without further purification.

Stage L.1: (S)-2-Carbamoyl-azetidine-1-carboxylic acid benzyl ester

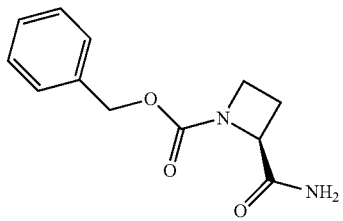 [SMILES: NC(=O)[C@@H]1CCN1C(=O)OCc1ccccc1]

A mixture of (S)-azetidine-1,2-dicarboxylic acid 1-benzyl ester 2-methyl ester (2.5 g) and 7 M ammonia in MeOH (10 ml) was stood at it for 18 h in a sealed vessel. The RM was then evaporated to give the title compound as a white solid which was used without further purification. MS: M+H 235.1 and M−H 233.1.

Intermediate M:
(2S,4R)-4-fluoro-pyrrolidine-2-carboxylic acid amide

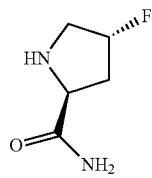

A 1.25 M solution of HCl in EtOH (2.3 ml) was added to a suspension of (2S,4R)-4-fluoro-pyrrolidine-2-carboxylic acid (0.25 g) in EtOH (2 ml) at rt and the mixture heated for 62 h at 55° C. The RM was evaporated and a 7 M solution of ammonia in MeOH (5.6 ml) added. The RM was stood at rt for 36 h then evaporated, the residue triturated with MeOH (0.5 ml) and filtered to give the title compound as a white solid. $^1$H-NMR (d$_6$-DMSO, 400 MHz): 7.68 (s, 1H), 7.37 (s, 1H), 5.30 (d, 1H), 3.96 (t, 1H), 3.40-3.12 (m, 2H), 2.48-2.31 (m, 1H), 2.02-1.81 (m, 1H).

Intermediate N:
(2S,4S)-4-Fluoro-pyrrolidine-2-carboxylic acid amide

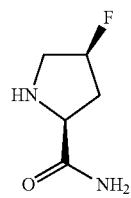

A mixture of (2S,4S)-2-carbamoyl-4-fluoro-pyrrolidine-1-carboxylic acid tert-butyl ester (1.0 g), conc. HCl (0.6 ml) and 1-butanol (10 ml) was heated for 48 h at 50° C. The RM was evaporated and partitioned DCM and aqueous NaHCO$_3$, the DCM layers were dried over Na$_2$SO$_4$ and evaporated. A solution of 7 M ammonia in methanol (10 ml) was added to the residue and the mixture was stood for 60 h at it in a sealed vessel. Evaporation and trituration with EtOH gave the title compound as a white solid.

Intermediate O:
(1S,5R)-2-Aza-bicyclo[3.1.0]hexane-1-carboxylic acid amide

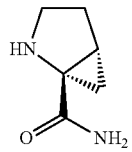

A mixture of (1S,5R)-2-aza-bicyclo[3.1.0]hexane-1-carboxylic acid ethyl ester (2.5 g, prepared by the procedure of Hercouet *Tetrahedron Asymmetry* 1996, 7, 1267-1268.) and 7 M ammonia in MeOH (20 ml) was heated in a sealed vessel at 80° C. for 5 days. The cooled RM was evaporated and triturated with hexanes/DCM to give the title compound as a beige solid. $^1$H-NMR (DMSO-d$_6$, 400 MHz): 7.15 (s, 1H), 7.04 (s, 1H), 3.00-2.91 (m, 1H), 2.67 (q, 1H), 1.94-1.83 (m, 1H), 1.74-1.67 (m, 1H), 1.64-1.55 (m, 1H), 1.38-1.31 (m, 1H), 0.90 (t, 1H)).

Intermediate P:
(2S,3R)-3-Methyl-pyrrolidine-2-carboxylic acid amide

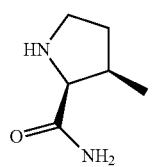

(2S,3R)-3-Methyl-1-((S)-1-phenyl-ethyl)-pyrrolidine-2-carboxylic acid amide (Stage P.1, 1.1 g, 4.76 mmol) and Pd on charcoal 10% (0.101 g, 0.947 mmol) in MeOH (20 mL) was shaken under a H$_2$ atm. for 46 h at rt. The RM was then filtered through a Fluoropore Membrane Filter (0.2 μm FG) and evaporated. The residue was dissolved in DCM and evaporated to dryness to give the title compound as white crystals MS: M+H=129.0. $^1$H-NMR (d$_6$-DMSO, 600 MHz): 7.34 (s, br,1H), 7.10 (s, br,1H), 3.48 (d, 1H), 3.0.2-2.97 (m, 1H), 2.80-2.75 (m, 1H), 2.35-2.28 (m, 1H), 1.88-1.81 (m, 1H), 1.39-1.32 (m, 1H), 0.83 (d, 3H).

Stage P.1: (2S,3R)-3-Methyl-1-((S)-1-phenyl-ethyl)-pyrrolidine-2-carboxylic acid amide

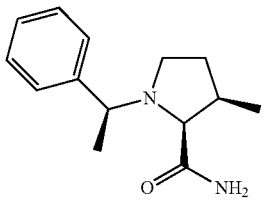 [SMILES: C[C@@H]1CCN([C@@H](C)c2ccccc2)[C@@H]1C(N)=O]

Trimethylaluminum in toluene (2 M, 3.23 mL) was added dropwise to a mixture of ammonium chloride (0.346 g, 6.47 mmol) in toluene (3.2 mL) at 0° C. under an argon atm., with the formation of methane gas. The RM was then allowed to warm to rt, and stirred at rt for a further 15 min. before (2S,3R)-3-methyl-1-((S)-1-phenyl-ethyl)-pyrrolidine-2-carboxylic acid methyl ester (prepared as described in *Tetr. Lett.* 1997, 38 (1), 85-88; 1.6 g, 6.47 mmol) was slowly added. The RM was stirred at it for 56 h, 1 M HCl was then added with cooling and the RM washed 3× with DCM. The aqueous phase was basified with Na$_2$CO$_3$, extracted 3× with DCM and the combined organic layers dried over Na$_2$SO$_4$. Evaporation gave the title compound as a yellowish oil. MS: M+H=233.2. HPLC: t$_R$ 3.17 min (method D). $^1$H-NMR (d$_6$-DMSO, 600 MHz): 7.37-7.33 (m, 2H), 7.30 (t, 2H), 7.25 (s, br,1H), 7.21 (t, 1H), 7.12 (s, br,1H), 3.55 (q, 1H), 3.40 (d, 1H), 2.71 (t, 1H), 2.28-2.22 (m, 1H), 2.21-2.16 (m, 1H), 1.71 (qt, 1H), 1.38-1.31 (m, 1H), 1.21 (d, 3H), 0.90 (d, 3H).

Intermediate Q:
(2S,4S)-4-Dimethylamino-pyrrolidine-2-carboxylic acid amide

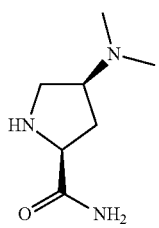

A solution of (2S,4S)-4-dimethylamino-pyrrolidine-2-carboxylic acid butyl ester (Stage Q.1, 326 mg) and 7 M ammonia in MeOH (8 ml) was stood for 18 h at it in a sealed vessel. Filtration, evaporation and trituration with Et$_2$O/MeOH gave the title compound as a beige solid.

Stage Q.1:
(2S,4S)-4-Dimethylamino-pyrrolidine-2-carboxylic acid butyl ester

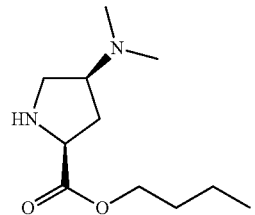

Concentrated HCl (0.3 ml) was added to a mixture of (2S,4S)-4-dimethylamino-pyrrolidine-2-carboxylic acid methyl ester dihydrochloride (400 mg) and 1-butanol (4 ml) and heated for 18 h at 115° C. After cooling the RM was evaporated then partitioned between DCM and aqueous NaHCO$_3$ solution and the DCM layers dried and evaporated to give the title compound as a brown oil which was used without further purification.

Intermediate R:
(2S,4S)-4-Hydroxy-pyrrolidine-2-carboxylic acid amide

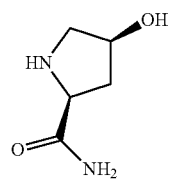

A solution of (2S,4S)-4-hydroxy-pyrrolidine-2-carboxylic acid methyl ester hydrochloride (1 g) in a 7M solution of ammonia in MeOH (10 ml) was stirred for 18 h then evaporated and triturated with Et$_2$O. The residue was dissolved in the minimum volume of hot MeOH and stood at 4° C. for 4 h. The title compound was isolated by filtration as a white solid.

Intermediate S:
(2S,4R)-4-hydroxy-pyrrolidine-2-carboxylic acid amide

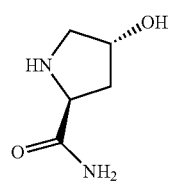

A solution of (2S,4R)-4-hydroxy-pyrrolidine-2-carboxylic acid benzyl ester (1 g) in 880 ammonia (5 ml) was stirred for 18 h then evaporated and triturated with Et$_2$O to give the title compound as a white solid. $^1$H-NMR (d$_6$-DMSO, 400 MHz): 9.15 (s, br, 1H), 8.04 (s, 1H), 7.63 (s, 1H), 5.56 (s, 1H), 4.40 (s, 1H), 4.27-4.16 (m, 1H), 3.27 (d, 1H), 3.02 (d, 1H), 2.33 -2.19 (m, 1H), 1.89-1.76 (m, 1H).

Intermediate T: Imidazole-1-carboxylic acid (7-tert-butyl-4,5-dihydro-benzo[1,2-d;3,4-d']bisthiazol-2-yl)-amide

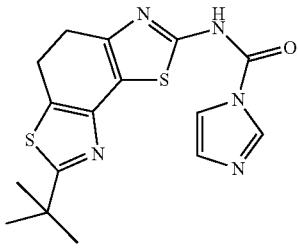 [SMILES: CC(C)(C)c1nc2c(s1)CCc1nc(NC(=O)n3ccnc3)sc1-2]

7-tert-Butyl-4,5-dihydro-benzo[1,2-d;3,4-d']bisthiazol-2-ylamine (Stage T.1, 175 mg, 0.659 mmol) was dissolved in DCM (10 mL), CDI (297 mg, 1.648 mmol) was then added, and the RM was stirred at rt for 2 h. The title compound was isolated by filtration, washed with DCM and dried under HV.

Stage T.1: 7-tert-Butyl-4,5-dihydro-benzo[1,2-d;3,4-d']bisthiazol-2-ylamine

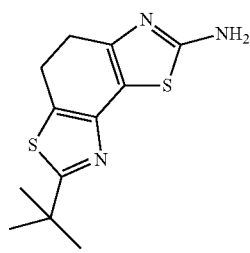 [SMILES: CC(C)(C)c1nc2c(s1)CCc1nc(N)sc1-2]

N-(7-tert-Butyl-4,5-dihydro-benzo[1,2-d;3,4-d']bisthiazol-2-yl)-acetamide (Stage T.2, 225 mg, 0.732 mmol) was dissolved in EtOH (10 mL), HCl 36% (1.48 g, 14.64 mmol) was then added, and the RM heated to reflux. After 18 hours at reflux the RM was cooled to rt and adjusted to pH 8-9 by the addition of 5% aqueous sodium bicarbonate solution, extracted with EtOAc, and washed two times with $H_2O$. The organic layer was dried over $Na_2SO_4$ and evaporated to give the title product ($t_R$ 4.408 min (Method F)).

Stage T.2: N-(7-tert-Butyl-4,5-dihydro-benzo[1,2-d;3,4-d']bisthiazol-2-yl)-acetamide

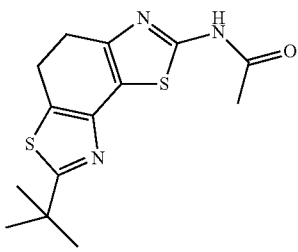 [SMILES: CC(=O)Nc1nc2c(s1)-c1nc(C(C)(C)C)sc1CC2]

N-(6-Bromo-7-oxo-4,5,6,7-tetrahydro-benzothiazol-2-yl)-acetamide (Stage T.3, 473 mg, 1.635 mmol) was dissolved in MeOH (10 mL), 2,2-dimethylthio propionamide (230 mg, 1.962 mmol) and ammonium phosphomolybdate (307 mg, 0.164 mmol) were added, and the RM was stirred at 25° C. for 20 h. The RM was then stood for 2 days before stirring at 50° C. for 24 h. The mixture was extracted with EtOAc/$H_2O$. The organic layers were dried over $Na_2SO_4$ and evaporated. The crude material was chromatographed with 30 g of silica gel, eluent DCM/MeOH=99:1. Fractions containing the product were evaporated and lyophilized from dioxane to give 225 mg of the title compound as a white solid (M+H=308; M−H=306; $t_R$ 5.525 min (Method F)).

Stage T.3: N-(6-Bromo-7-oxo-4,5,6,7-tetrahydro-benzothiazol-2-yl)-acetamide

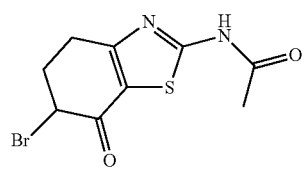

N-(7-Oxo-4,5,6,7-tetrahydro-benzothiazol-2-yl)-acetamide (Stage T.4, 2.286 g, 10.87 mmol) was dissolved in AcOH (60 ml), then bromine (1.74 g, 10.87 mmol) dissolved in AcOH (10 mL) were slowly added and the RM was heated to 75° C. for 20 h. The color changed from red to beige. The mixture was evaporated and the residue was dissolved in MeOH (10 mL) and precipitated with $H_2O$. The mixture was filtered and dried on HV. The crude material was chromatographed with MPLC C18 $H_2O$ 0.1% TFA/$CH_3CN$ 0.1% TFA, gradient 0-50%. Fractions containing the product were neutralized with $NaHCO_3$, extracted with EtOAc and lyophilized from dioxane to give of the title compound as a white solid (M+H=291; M−H=289; $t_R$ 4.29 (Method F)). $^1$H-NMR ($d_6$-DMSO, 600.13 MHz) 12.75 (s, 1H) 4.95 (t, 1H), 2.95-2.84 (m, 2H), 2.62-2.52 (m, 1H), 2.40-2.30 (m, 1H), 2.20 (s, 3H).

Stage T.4: N-(7-Oxo-4,5,6,7-tetrahydro-benzothiazol-2-yl)-acetamide

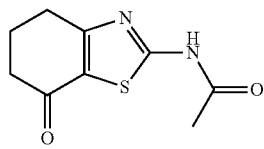

To acetic anhydride (80 mL) was added at rt 2-amino-5,6-dihydro-4H-benzothiazol-7-one (10 g, 59.4 mmol) and the yellow suspension was heated to reflux. After 1.75 h stirring at this temperature, the RM was allowed to cool with stirring, and stirred overnight at rt. After further cooling with an ice/NaCl bath, the suspension was filtered. The solid was then refluxed twice with acetone (10 mL then 15 mL) and filtered. The resulting solid was dried under vacuum at 40° C. overnight to afford the title compound as a beige solid (HPLC: $t_R$ 3.47 min (Method A3), M−H=211.1), $^1$H-NMR in DMSO-d6 (600 MHz): 12.55 (s, br, 1H); 2.84 (t, 2H); 2.48 (t, 2H); 2.17 (s, 3H); 2.065 (qt, 2H)).

Intermediate U: Imidazole-1-carboxylic acid [7-(2-fluoro-1,1-dimethyl-ethyl)-4,5-dihydro-benzo[1,2-d;3,4-d']bisthiazol-2-yl]-amide

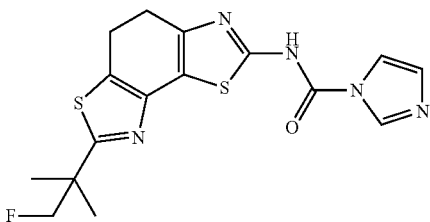 [SMILES: CC(C)(CF)c1nc2c(s1)CCc1nc(NC(=O)n3ccnc3)sc1-2]

7-(2-Fluoro-1,1-dimethyl-ethyl)-4,5-dihydro-benzo[1,2-d;3,4-d']bisthiazol-2-lamine (Stage U.1 61.6 mg, 0.217 mmol) was dissolved in DCM (2 mL), and CDI (297 mg, 1.648 mmol) added to give a clear colorless solution. The RM stood overnight at rt to give a white suspension. The mixture was cooled at 4° C. for 1 h and then filtered, washed with DCM and dried under vacuum to give of the title compound as a white solid (analysis of a sample in MeOH; M+H=342.0 showed methyl carbamate product in MS; $t_R$ 2.14 min (Method A3)).

Stage U.1 7-(2-Fluoro-1,1-dimethyl-ethyl)-4,5-dihydro-benzo[1,2-d;3,4-d']bisthiazol-2-lamine

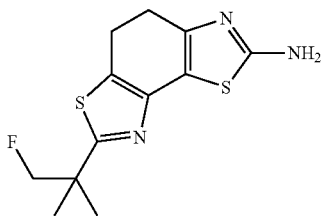 [SMILES: CC(C)(CF)c1nc2c(s1)CCc1nc(N)sc1-2]

3-Fluoro-2,2-dimethyl-thiopropionamide (Stage U.2, 394 mg, 2.331 mmol) was dissolved in EtOH, N-(6-bromo-7-oxo-4,5,6,7-tetrahydro-benzothiazol-2-yl)-acetamide (Stage T.3, 473 mg, 1.635 mmol) and ammonium phosphomolybdate (80 mg, 0.042 mmol) were then added to give a yellow suspension. The RM was heated to reflux to give a dark blue-green suspension. The reaction mixture was stirred at 65° C. 3 days. The RM was filtered and the filtrate evaporated. The residue was taken up in DMF and purified by prep-HPLC (method E). Fractions containing the product were combined and evaporated to give the title compound as a white solid (M+H=284.1; $t_R$ 1.30 min (Method A3)).

Stage U.2 3-Fluoro-2,2-dimethyl-thiopropionamide

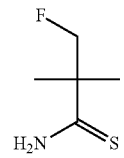

The title compound was prepared by the procedure of Boys, M. L.; Downs, V. L. Synth. Commun. 2006, 36, 295. Sodium hydrogen sulphide hydrate (3.89 g, 69.4 mmol, hygroscopic) was added to a solution of 3-fluoro-2,2-dimethyl-propionitrile (Stage U.3, 1.17 g, 11.57 mmol) and diethyl amine hydrochloride (7.61 g, 69.4 mmol) in 1,4-dioxane (7 mL) and H$_2$O (7 mL) at rt. The RM was heated to 55° C. and then stirred for 3 days at this temperature. The reaction mixture was diluted with water (50 ml) and extracted 5× with EtOAc (50 mL). The organic layers were dried over Na$_2$SO$_4$ and evaporated to give an orange oil. DCM (5 mL) was then added to give a white suspension. The suspension was filtered and the filtrate was purified with flash chromatography on silica gel eluting with DCM. The product containing fractions were evaporated to give the title compound as a pale yellow oil (M+H=136.1, M−H=134.1; $t_R$ 0.69 min (Method A3)). $^{19}$F-NMR (d$_6$-DMSO, 400 MHz 218 ppm (t, 1F)).

Stage U.3 3-Fluoro-2,2-dimethyl-propionitrile

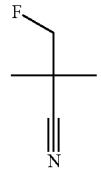

3-Fluoro-2,2-dimethyl-propionamide (Stage U.4, 1.82 g, 15.28 mmol) and phosphorus pentoxide (2.168 g, 15.28 mmol) were combined to give a free flowing white powder which was heated with an oil bath to a bath temperature of 180° C. over 50 minutes under an argon atmosphere. A 300 mbar vacuum was then slowly applied distilling a mobile clear colourless oil which formed a low melting waxy solid on standing of the title compound. $^{19}$F-NMR (d$_6$-DMSO, 400 MHz 219.5 ppm (t, 1F)).

Stage U.4 3-Fluoro-2,2-dimethyl-propionamide

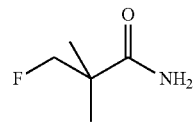

3-Fluoro-2,2-dimethyl-propionyl fluoride (DE3326874 and DE3611195, 2.5 g, 20.47 mmol) was added at 0° C. to a mixture of aqueous ammonia (10 mL) and THF (20 mL). The RM was then allowed to warm to rt and stood overnight at rt. The volume was reduced by 50% under vacuum to give a thick white suspension. The suspension was extracted with DCM/H₂O. The organic layers were dried over Na₂SO₄ and evaporated to give the title compound as a white crystalline solid.

Intermediate V: Imidazole-1-carboxylic acid (7-cyclopropylmethyl-4,5-dihydro-benzo[1,2-;3,4-d'] bisthiazol-2-yl)-amide

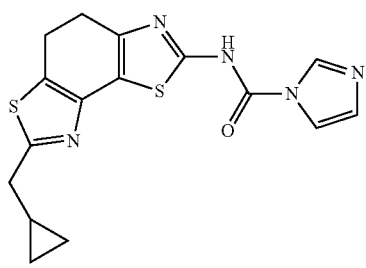 [SMILES: O=C(Nc1nc2c(s1)-c1nc(CC3CC3)sc1CC2)n1ccnc1]

7-Cyclopropylmethyl-4,5-dihydro-benzo[1,2-d;3,4-d'] bisthiazol-2-ylamine (Stage V.1, 72 mg, 0.273 mmol) was dissolved in 5 mL DCM, CDI (73.9 mg, 0.410 mmol) was added, and the RM stirred at rt for 20 h. Additional CDI (37 mg, 0.205 mmol) was added and the RM stirred at rt for a further 2 hours. The mixture was filtered, washed with DCM and filtrate was evaporated to give the title compound (M+H=322.1; M−H=320.2 MS-ES in MeOH shows the methyl carbamate product).

Stage V.1 7-Cyclopropylmethyl-4,5-dihydro-benzo [1,2-d;3,4-d']bisthiazol-2-ylamine

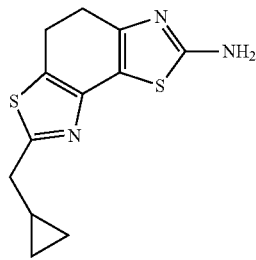 [SMILES: Nc1nc2c(s1)-c1nc(CC3CC3)sc1CC2]

N-(7-Cyclopropylmethyl-4,5-dihydro-benzo[1,2-d;3,4-d']bisthiazol-2-yl)-acetamide (Stage V.2, 180 mg, 0.589 mmol) was dissolved in EtOH (10 mL) and 36% HCl (1.193 g, 11.79 mmol) added. The RM was heated to 90° C. for 16 h then cooled and extracted with EtOAc/H₂O. The organic layer was dried over Na₂SO₄ and evaporated. The crude material was chromatographed with MPLC C18 H₂O 0.1% TFA/ CH₃CN 0.1% TFA, gradient 0-50%. Product containing fractions were neutralized with NaHCO₃, extracted with EtOAc and lyophilized from dioxane to give the title compound (M+H=264.2; M−H=262.1; $t_R$ 4.183 min (Method F)).

Stage V.2 N-(7-Cyclopropylmethyl-4,5-dihydro-benzo[1,2-d;3,4-d']bisthiazol-2-yl)-acetamide

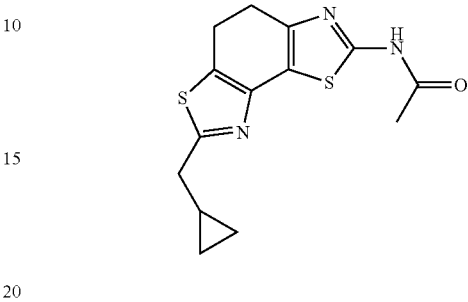

N-(6-Bromo-7-oxo-4,5,6,7-tetrahydro-benzothiazol-2-yl)-acetamide (Stage T.3, 347 mg, 1.200 mmol) was dissolved in MeOH (10 mL) and 2-cyclopropyl-thioacetamide (*Can. J. Chem* 1995 Vol. 73 1468-1477, 166 mg, 1.440 mmol) and ammonium phosphomolybdate (225 mg, 0.120 mmol) were added. The RM was stirred at rt for 20 h then heated at 50° C. for 3 h, 60° C. for 2 h and then refluxed for 24 h. The RM was partitioned between EtOAc/H₂O. The organic layer was dried over Na₂SO₄ and evaporated. The raw material was chromatographied with MPLC C18 H₂O 0.1% TFA/CH₃CN 0.1% TFA, gradient 0-50%. Product containing fractions were neutralized with NaHCO₃, extracted with EtOAc and lyophilized from dioxane to give the title compound as a white solid (M+H=306.2; M−H=304.2; $t_R$ 5.12 min (Method F)).

EXAMPLE 1

(2S,4R)-4-Dimethylamino-pyrrolidine-1,2-dicarboxylic acid 2-amide 1-[(8-tert-butyl-4,5-dihydro-thiazolo[4,5-h]quinazolin-2-yl)-amide]

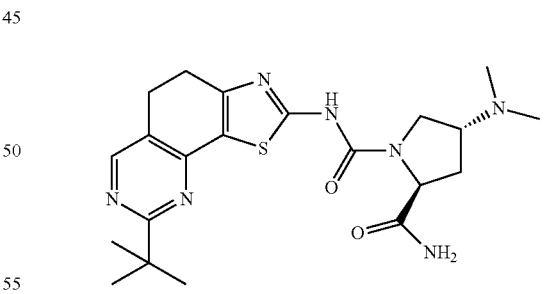

To a solution of imidazole-1-carboxylic acid (8-tert-butyl-4,5-dihydro-thiazolo[4,5-h]quinazolin-2-yl)-amide (Intermediate A, 45.1 mg, 0.127 mmol) in DMF (1 mL) was added (2S,4R)-4-dimethylamino-pyrrolidine-2-carboxylic acid amide (Intermediate B, 22 mg, 0.140 mmol) and triethylamine (0.053 ml, 0.382 mmol). The RM was then stirred at rt for 17 h and purified by preparative HPLC (method B). The product containing fractions were combined and eluted through a Bond Elut-SCX, 300 mg cartridge. The cartridge was then washed with a 7 M solution of ammonia in MeOH and evaporated to give the title compound. MS: M+H=444. HPLC: $t_R$ 3.17 min (method D).

EXAMPLE 2

(2S,3S)-3-Methyl-pyrrolidine-1,2-dicarboxylic acid 2-amide 1-[(8-diethylamino-4,5-dihydro-thiazolo[4,5-h]quinazolin-2-yl)-amide]

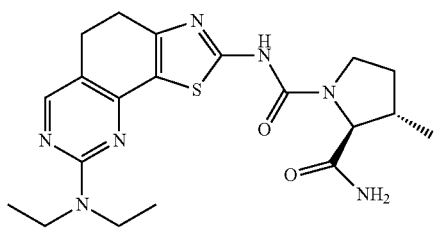 [SMILES: CCN(CC)c1ncc2c(n1)-c1sc(NC(=O)N3CC[C@H](C)[C@H]3C(N)=O)nc1CC2]

A mixture of (2S,3S)-3-methyl-pyrrolidine-2-carboxylic acid amide (Intermediate D, 6.24 mg, 0.049 mmol), imidazole-1-carboxylic acid (8-diethylamino-4,5-dihydro-thiazolo[4,5-h]quinazolin-2-yl)-amide (Intermediate C, 18 mg, 0.049 mmol) and triethylamine (0.020 mL, 0.146 mmol) in DMF (0.4 mL) was stirred at rt for 6 h. The RM was then directly purified by preparative HPLC (method B). The product containing fractions were then filtered through a 300 mg Bond Elut-SCX cartridge. The cartridge was then eluted with a 7 M ammonia solution in MeOH and the eluent evaporated to give the title compound as a yellow solid. MS: M+H=430.1. HPLC: $t_R$ 3.72 min (method D). $^1$H-NMR (DMSO-$d_6$, 600 MHz): 11.05 (s, 1H); 8.04 (s, 1H); 7.44 (s, br, 1H); 6.95 (s, br, 1H); 3.78 (s, br, 1H); 3.60-3.50 (m, 6H); 2.82 (s, br, 4H); 2.18 (s, br, 1H); 2.03 (s, br, 1H); 1.55 (s, br, 1H); 1.10 (t, 6H); 1.05 (d, 3H).

EXAMPLE 3

(R)-2-Benzyl-pyrrolidine-1,2-dicarboxylic acid 2-amide 1-[(8-diethylamino-4,5-dihydro-thiazolo[4,5-h]quinazolin-2-yl)-amide]

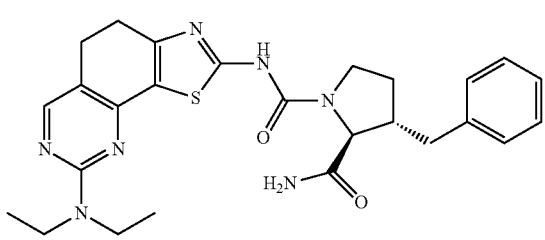 [SMILES: CCN(CC)c1ncc2c(n1)-c1sc(NC(=O)N3CC[C@H](Cc4ccccc4)[C@H]3C(N)=O)nc1CC2]

To a mixture of imidazole-1-carboxylic acid (8-diethylamino-4,5-dihydro-thiazolo[4,5-h]quinazolin-2-yl)-amide (Intermediate C, 50 mg, 0.135 mmol) in DMF (1 mL) was added (R)-2-benzyl-pyrrolidine-2-carboxylic acid amide (Intermediate E, 33.2 mg, 0.162 mmol) and triethylamine (0.057 mL, 0.406 mmol). The RM was stirred for 21 h at 40° C. and then directly purified with preparative HPLC (method B). The product containing fractions were eluted through a 300 mg Bond Elut-SCX, cartridge. The cartridge was then eluted with 7 M ammonia-solution in MeOH and evaporated give the title compound as a yellow solid. MS: M+H=506.1. HPLC: $t_R$ 4.38 min (method D).

EXAMPLE 4

(S)-2-Methyl-pyrrolidine-1,2-dicarboxylic acid 2-amide 1-[(8-diethylamino-4,5-dihydro-thiazolo[4,5-h]quinazolin-2-yl)-amide]

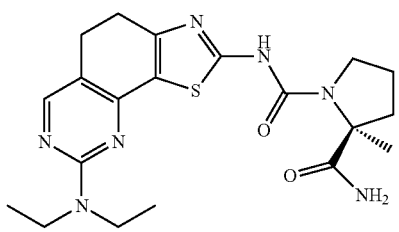 [SMILES: CCN(CC)c1ncc2c(n1)-c1sc(NC(=O)N3CCC[C@@]3(C)C(N)=O)nc1CC2]

To a mixture of imidazole-1-carboxylic acid (8-diethylamino-4,5-dihydro-thiazolo[4,5-h]quinazolin-2-yl)-amide (Intermediate C, 75 mg, 0.203 mmol) in DMF (2 mL) was added (S)-2-methyl-pyrrolidine-2-carboxylic acid amide (Intermediate F, 39 mg, 0.305 mmol) and triethylamine (0.085 mL, 0.609 mmol). The RM was stirred for at 40° C. 17 h and then directly purified with preparative HPLC (method B). The product containing fractions were eluted through a 300 mg Bond Elut-SCX cartridge. The cartridge was then eluted with 7 M ammonia-solution in MeOH and evaporated to give the title compound as a yellow solid MS: M+H=430.2. HPLC: $t_R$ 3.80 min (method D).

EXAMPLE 5

(R)-2-Methoxymethyl-pyrrolidine-1,2-dicarboxylic acid 2-amide 1-[(8-diethylamino-4,5-dihydro-thiazolo[4,5-h]quinazolin-2-yl)-amide]

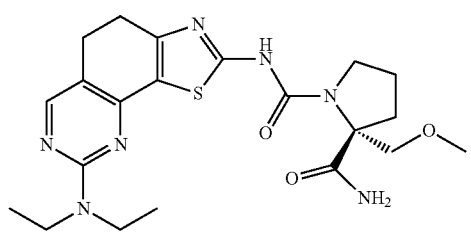 [SMILES: CCN(CC)c1ncc2c(n1)-c1sc(NC(=O)N3CCC[C@@]3(COC)C(N)=O)nc1CC2]

A mixture of imidazole-1-carboxylic acid (8-diethylamino-4,5-dihydro-thiazolo[4,5-h]quinazolin-2-yl)-amide (Intermediate C, 75 mg, 0.203 mmol), (R)-2-methoxymethyl-pyrrolidine-2-carboxylic acid amide (Intermediate G, 35.3 mg, 0.223 mmol) and triethylamine (0.085 mL, 0.609 mmol) in DMF (2 mL) was stirred for 6 h at 40° C. After cooling to rt, the RM was dissolved in MeOH (1 mL) and directly purified by preparative HPLC (method B). The product containing fractions were eluted through a 300 mg Bond Elut-SCX cartridge. The cartridge was then eluted with 7 M

EXAMPLE 6

(R)-2-Dimethylaminomethyl-pyrrolidine-1,2-dicarboxylic acid 2-amide 1-[(8-tert-butyl-4,5-dihydro-thiazolo[4,5-h]quinazolin-2-yl)-amide]

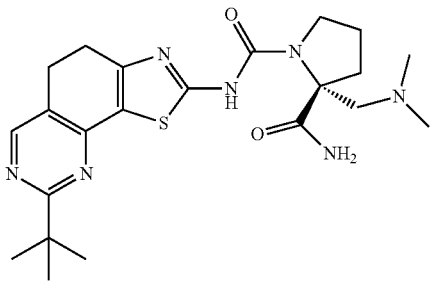 [SMILES: CN(C)C[C@@]1(C(N)=O)CCCN1C(=O)Nc1nc2c(s1)-c1nc(C(C)(C)C)ncc1CC2]

Imidazole-1-carboxylic acid (8-tert-butyl-4,5-dihydrothiazolo[4,5-h]quinazolin-2-yl)-amide (Intermediate A, 132 mg, 0.372 mmol) was added to a mixture of (R)-2-dimethylaminomethyl-pyrrolidine-2-carboxylic acid amide (Intermediate H, 70 mg, 0.409 mmol) and triethylamine (0.155 mL, 1.115 mmol) in DMF (1 mL) at rt. After 18 hours MeOH (0.5 ml) was added, the RM filtered through a PTFE membrane filter and purified by preparative HPLC (method B). The product containing fractions were combined and evaporated to remove CH$_3$CN and then basified by the addition of solid NaHCO$_3$ to give a yellow white precipitate. After cooling to 4° C., the solid was recollected by filtration and then further purified by preparative HPLC (method C). The product containing fractions were eluted through a 300 mg Bond Elut-SCX cartridge. The cartridge was then eluted with a 7 M ammonia in MeOH solution and evaporated to give the title product as a yellow amorphous glass. LCMS: t$_R$ 0.98 min and M+H=458.1 (method A3). $^1$H-NMR (CD$_3$OD, 400 MHz): 8.28 (s, 1H); 3.92-3.82 (m, 1H); 3.67-3.44 (m, 2H); 3.04-2.88 (m, 4H); 2.85-2.71 (m, 1H); 2.56 (s, br, 6H); 2.29-2.19 (m, 1H); 2.08-1.87 (m, 3H); 1.37 (s, 9H).

EXAMPLE 7 d$_6$-(R)-2-Dimethylaminomethyl-pyrrolidine-1,2-dicarboxylic acid 2-amide 1-[(8-tert-butyl-4,5-dihydro-thiazolo[4,5-h]quinazolin-2-yl)-amide]

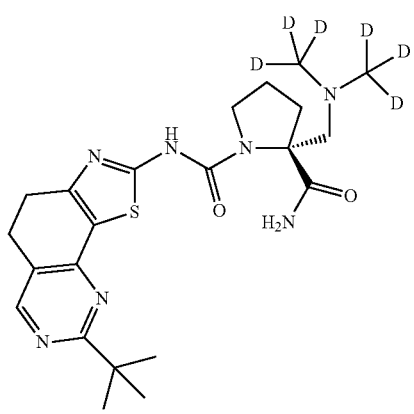 [SMILES: [2H]C([2H])([2H])N(C[C@@]1(C(N)=O)CCCN1C(=O)Nc1nc2c(s1)-c1nc(C(C)(C)C)ncc1CC2)C([2H])([2H])[2H]]

Imidazole-1-carboxylic acid (8-tert-butyl-4,5-dihydrothiazolo[4,5-h]quinazolin-2-yl)-amide (Intermediate A, 91 mg, 0.256 mmol) and triethylamine (0.036 mL, 0.256 mmol) were added to d$_6$-(R)-2-dimethylaminomethyl-pyrrolidine-2-carboxylic acid amide (Intermediate I, 50 mg, 0.282 mmol) suspended in DMF (2 mL) under an argon atm. The RM was then stirred for 2.75 h at 40° C. and then purified directly by preparative HPLC twice (method B and then method C). Each time, fractions containing the product were combined and eluted through a 300 mg Bond Elut-SCX cartridge. The cartridge was then eluted with a 7 M ammonia in MeOH solution and evaporated to give a yellow solid. The solid was suspended in DCM, filtered and dried in vacuo to give the title compound as a yellow solid. LCMS: t$_R$ 1.21 min and M+H=464.0 (method A1).

EXAMPLE 8

(R)-2-Hydroxymethyl-pyrrolidine-1,2-dicarboxylic acid 2-amide 1-[(8-diethylamino-4,5-dihydro-thiazolo[4,5-h]quinazolin-2-yl)-amide]

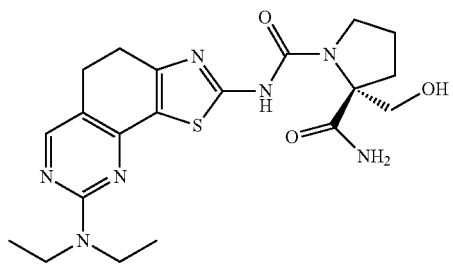 [SMILES: CCN(CC)c1ncc2c(n1)-c1sc(NC(=O)N3CCC[C@@]3(CO)C(N)=O)nc1CC2]

Imidazole-1-carboxylic acid (8-diethylamino-4,5-dihydro-thiazolo[4,5-h]quinazolin-2-yl)-amide (Intermediate C, 50 mg, 0.135 mmol) was added to a mixture of (R)-2-hydroxymethyl-pyrrolidine-2-carboxylic acid amide (Intermediate J, 25.4 mg, 0.176 mmol) and triethylamine (0.047 mL, 0.338 mmol) in DMF (1 mL) at rt. After 18 h at rt the RM was filtered through a PTFE membrane and purified by preparative HPLC (method B). Product containing fractions the were combined and filtered through a Bond Elut-SCX cartridge. The cartridge was then eluted with a 7 M ammonia in MeOH solution and evaporated to give an orange glass which was recrystallized from MeOH/water to afford the title compound as a yellow solid. LCMS: t$_R$ 1.09 min and M+H=446.0 (method A3).

EXAMPLE 9

(R)-2-Hydroxymethyl-pyrrolidine-1,2-dicarboxylic acid 2-amide 1-[(8-tert-butyl-4,5-dihydro-thiazolo[4,5-h]quinazolin-2-yl)-amide]

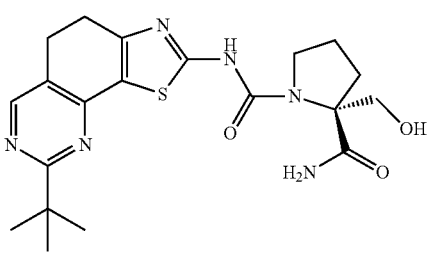 [SMILES: CC(C)(C)c1ncc2c(n1)-c1sc(NC(=O)N3CCC[C@@]3(CO)C(N)=O)nc1CC2]

Imidazole-1-carboxylic acid (8-tert-butyl-4,5-dihydrothiazolo[4,5-h]quinazolin-2-yl)-amide (Intermediate A, 124 mg, 0.350 mmol) was added to a mixture of (R)-2-hydroxymethyl-pyrrolidine-2-carboxylic acid amide (Intermediate J, 63 mg, 0.350 mmol) and triethylamine (0.049 mL, 0.350 mmol) in DMF (2 mL). The RM was stirred for 2 h at 40° C. then stood for 18 h at rt and then directly purified by preparative HPLC (method B). The product containing fractions were eluted through a 300 mg Bond Elut-SCX cartridge. The cartridge was then eluted with 7 M solution of ammonia in MeOH and evaporated to give a yellow solid. The isolated solid was then suspended in DCM, filtered and dried to give title compound as a pale yellow/white solid. LCMS: $t_R$ 1.31 min and M+H=430.9 (method A1).

EXAMPLE 10

(R)-2-{[(3-Fluoro-benzyl)-methyl-amino]-methyl}-pyrrolidine-1,2-dicarboxylic acid 2-amide 1-[(8-tert-butyl-4,5-dihydro-thiazolo[4,5-h]quinazolin-2-yl)-amide]

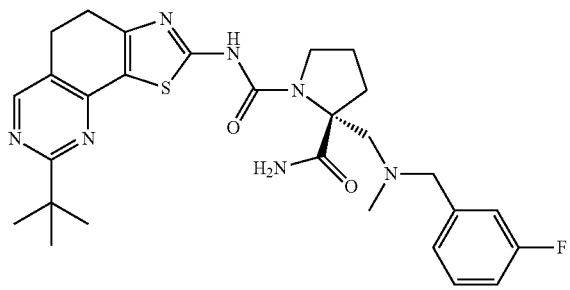 [SMILES: CN(Cc1cccc(F)c1)C[C@@]1(C(N)=O)CCCN1C(=O)Nc1nc2c(s1)-c1nc(C(C)(C)C)ncc1CC2]

Imidazole-1-carboxylic acid (8-tert-butyl-4,5-dihydro-thiazolo[4,5-h]quinazolin-2-yl)-amide (Intermediate A, 40.1 mg, 0.113 mmol) and triethylamine (0.047 mL, 0.339 mmol) were added to (R)-2-{[(3-fluoro-benzyl)-methyl-amino]-methyl}-pyrrolidine-2-carboxylic acid amide (Intermediate K, 30 mg, 0.113 mmol) suspended in DMF (1 mL) at rt under argon. The RM was stirred for 2.5 h at 40° C. and then directly purified by preparative HPLC (method C). The product containing fractions were eluted through a Bond Elut-SCX, 300 mg cartridge. The cartridge was then eluted with a 7 M solution of ammonia in MeOH and evaporated to give a yellow solid. The solid was triturated with DCM, filtered and dried to give the title compound as a pale yellow solid. LCMS: $t_R$ 0.81 min and M+H=552.3 (method A2).

EXAMPLE 11

(S)-2-Methyl-pyrrolidine-1,2-dicarboxylic acid 2-amide 1-[(8-tert-butyl-4,5-dihydro-thiazolo[4,5-h]quinazolin-2-yl)-amide]

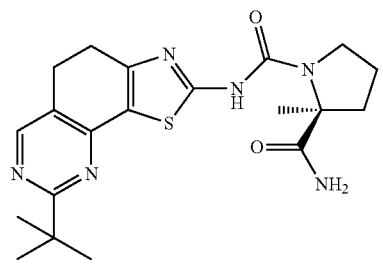 [SMILES: CC(C)(C)c1ncc2c(n1)-c1sc(NC(=O)N3CCC[C@@]3(C)C(N)=O)nc1CC2]

(S)-2-Methyl-pyrrolidine-2-carboxylic acid amide (Intermediate F, 22.14 mg, 0.169 mmol) and triethylamine (0.035 mL, 0.254 mmol) were added to imidazole-1-carboxylic acid (8-tert-butyl-4,5-dihydro-thiazolo[4,5-h]quinazolin-2-yl)-amide (Intermediate A, 30 mg, 0.085 mmol) in DMF (1 mL) under argon at rt. After stirring 16 h at rt the RM was directly purified by preparative HPLC (method B). The product containing fractions were eluted through a 300 mg Bond Elut-SCX cartridge. The cartridge was then eluted with a 7 M solution of ammonia in MeOH and evaporated to give the title compound as a yellow crystalline solid. MS: M+H=415.1. HPLC: $t_R$ 3.73 min (method D).

EXAMPLE 12

(S)-Pyrrolidine-1,2-dicarboxylic acid 2-amide 1-[(8-diethylamino-4,5-dihydro-thiazolo[4,5-h]quinazolin-2-yl)-amide]

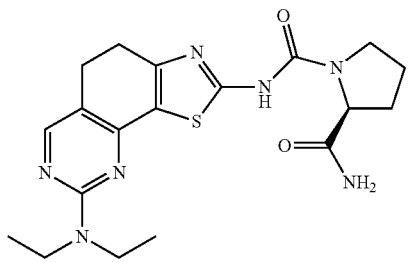 [SMILES: CCN(CC)c1ncc2c(n1)-c1sc(NC(=O)N3CCC[C@H]3C(N)=O)nc1CC2]

(S)-Pyrrolidine-2-carboxylic acid amide (148 mg, 1.299 mmol) and triethylamine (0.272 mL, 1.949 mmol) were added to imidazole-1-carboxylic acid (8-diethylamino-4,5-dihydro-thiazolo[4,5-h]quinazolin-2-yl)-amide (Intermediate C, 240 mg, 0.65 mmol) and (DMF (1 mL) under argon at rt. The RM was stirred for 15.5 h at rt and then purified with preparative HPLC (method C). Product containing fractions were combined and filtered through a Bond Elut-SCX cartridge. The cartridge was then eluted with a 7 M solution of ammonia in MeOH and evaporated to give the title compound as orange crystals. MS: M+H=416.1. HPLC: $t_R$ 3.56 min (method D).

EXAMPLE 13

(S)-Azetidine-1,2-dicarboxylic acid 2-amide 1-[(8-diethylamino-4,5-dihydro-thiazolo[4,5-h]quinazolin-2-yl)-amide]

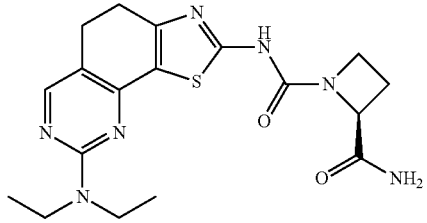 [SMILES: CCN(CC)c1ncc2c(n1)-c1sc(NC(=O)N3CC[C@H]3C(N)=O)nc1CC2]

A mixture of (S)-azetidine-2-carboxylic acid amide (Intermediate L, 26.4 mg, 0.264 mmol), imidazole-1-carboxylic acid (8-diethylamino-4,5-dihydro-thiazolo[4,5-h]quinazolin-2-yl)-amide (Intermediate C, 75 mg, 0.203 mmol) and triethylamine (0.085 mL, 0.609 mmol) in DMF (2 mL) was stirred at 40° C. for 2 h. The RM was then purified directly by preparative HPLC (method B). The product containing fractions were eluted through a 300 mg Bond Elut-SCX cartridge. The cartridge was then eluted with a 7 M solution of ammonia in MeOH and evaporated to give the title compound as a white crystalline solid. MS: M+H=402.1. HPLC: $t_R$ 3.56 min (method D).

EXAMPLE 14

(S)-Pyrrolidine-1,2-dicarboxylic acid 2-amide 1-[(8-tert-butyl-4,5-dihydro-thiazolo[4,5-h]quinazolin-2-yl)-amide]

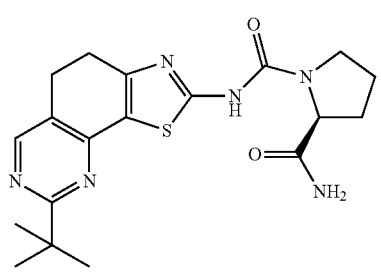 [SMILES: CC(C)(C)c1ncc2c(n1)-c1sc(NC(=O)N3CCC[C@H]3C(N)=O)nc1CC2]

(S)-Pyrrolidine-2-carboxylic acid amide (16 mg, 0.14 mmol) was added to a mixture of imidazole-1-carboxylic acid (8-tert-butyl-4,5-dihydro-thiazolo[4,5-h]quinazolin-2-yl)-amide (Intermediate A, 45 mg, 0.127 mmol) and triethylamine (0.053 mL, 0.381 mmol) in DMF (1 mL) at rt. The RM was stood overnight at rt, then evaporated and the residue crystallized from MeOH and water. The title compound was collected by filtration. MS: M+H=401.1 (MS-ESI). $^1$H-NMR (CD$_3$OD, 400 MHz): 8.31 (s, 1H), 4.46 (d, 1H), 3.77-3.54 (m, 2H), 3.08-2.90 (m, 4H), 2.33-2.23 (m, 1H), 2.13-2.00 (m, 3H), 1.38 (s, 9H)).

EXAMPLE 15

5-Methyl-pyrrolidine-1,2-dicarboxylic acid 2-amide 1-[(8-diethylamino-4,5-dihydro-thiazolo[4,5-h]quinazolin-2-yl)-amide]

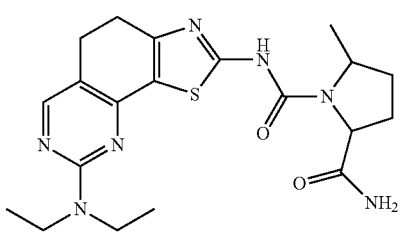 [SMILES: CCN(CC)c1ncc2c(n1)-c1sc(NC(=O)N3C(C)CCC3C(N)=O)nc1CC2]

To a suspension of imidazole-1-carboxylic acid (8-diethylamino-4,5-dihydro-thiazolo[4,5-h]quinazolin-2-yl)-amide (Intermediate C, 75 mg, 0.203 mmol) in DMF (2 mL) was added 5-methyl-pyrrolidine-2-carboxylic acid amide (prepared as described in *Arch. Pharm.*, 1936, 274, 40; 39 mg, 0.305 mmol) and triethylamine (0.085 mL, 0.609 mmol). The RM was stirred at 40° C. for 2.5 h. and then purified directly by preparative HPLC (method B). The product containing fractions were eluted through a Bond Elut-SCX cartridge. The cartridge was then eluted with a 7 M solution of ammonia in MeOH, evaporated and the residue triturated with DCM to give the title compound as a yellow solid. LCMS: $t_R$ 0.77 min and M+H=430.0 (method A2).

EXAMPLE 16

(2S,4R)-4-Fluoro-pyrrolidine-1,2-dicarboxylic acid 2-amide 1-[(8-diethylamino-4,5-dihydro-thiazolo[4,5-h]quinazolin-2-yl)-amide]

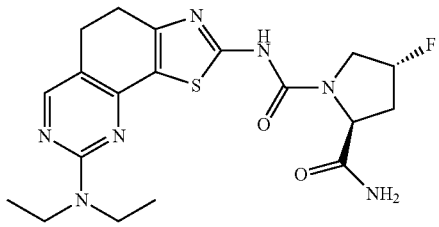 [SMILES: CCN(CC)c1ncc2c(n1)-c1sc(NC(=O)N3C[C@H](F)C[C@H]3C(N)=O)nc1CC2]

To imidazole-1-carboxylic acid (8-diethylamino-4,5-dihydro-thiazolo[4,5-h]quinazolin-2-yl)-amide (Intermediate C, 75 mg, 0.203 mmol) in DCM (2 mL) was added (2S,4R)-4-fluoro-pyrrolidine-2-carboxylic acid amide (Intermediate M, 40.2 mg, 0.305 mmol) and triethylamine (0.085 mL, 0.609 mmol). The RM was stirred at 40° C. for 17.5 h and then directly purified by preparative HPLC (method B). The product containing fractions were eluted through a Bond Elut-SCX cartridge. The cartridge was then eluted with a 7 M solution of ammonia in MeOH and evaporated to give the title compound as a yellow solid. HPLC: $t_R$ 3.66 min (method D). MS: M+H=434.1.

EXAMPLE 17

(2S,4S)-4-Fluoro-pyrrolidine-1,2-dicarboxylic acid 2-amide 1-[(8-diethylamino-4,5-dihydro-thiazolo[4,5-h]quinazolin-2-yl)-amide]

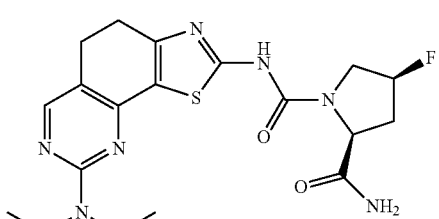

To imidazole-1-carboxylic acid (8-diethylamino-4,5-dihydro-thiazolo[4,5-h]quinazolin-2-yl)-amide (Intermediate C, 17 mg, 0.046 mmol) in DMF (0.4 mL) was added (2S,4S)-4-fluoro-pyrrolidine-2-carboxylic acid amide (Intermediate N, 6.08 mg, 0.046 mmol) and triethylamine (0.019 mL, 0.138 mmol). The RM was stirred at 40° C. for 17 h and then directly purified by preparative HPLC (method B). The product containing fractions were eluted through a Bond Elut-SCX cartridge. The cartridge was then eluted with a 7 M solution of ammonia in MeOH and evaporated to give the title compound as a yellow solid. HPLC: $t_R$ 3.55 min (method D). MS: M+H=434.1.

EXAMPLE 18

(1S,5R)-2-Aza-bicyclo[3.1.0]hexane-1,2-dicarboxylic acid 1-amide 2-[(8-tert-butyl-4,5-dihydro-thiazolo[4,5-h]quinazolin-2-yl)-amide]

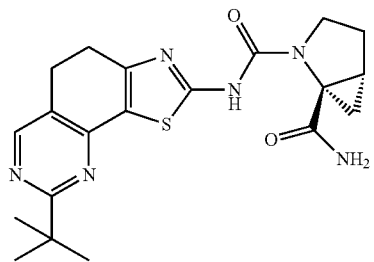 [SMILES: CC(C)(C)c1ncc2c(n1)-c1sc(NC(=O)N3CC[C@@H]4C[C@@]43C(N)=O)nc1CC2]

(1S,5R)-2-Aza-bicyclo[3.1.0]hexane-1-carboxylic acid amide (Intermediate O, 208 mg, 1.65 mmol) was added to a stirred mixture of imidazole-1-carboxylic acid (8-tert-butyl-4,5-dihydro-thiazolo[4,5-h]quinazolin-2-yl)-amide (Intermediate A, 532 mg, 1.5 mmol) and triethylamine (0.627 mL, 4.50 mmol) in DMF (4 mL) at rt. After 56 and 80 hours additional portions of (1S,5R)-2-aza-bicyclo[3.1.0]hexane-1-carboxylic acid amide (Intermediate O, 104 mg, 0.825 mmol) were added and the RM stood 18 h at rt. The RM was then filtered through a PTFE membrane and purified by preparative HPLC (method B). The product containing fractions were eluted through a Bond Elut-SCX cartridge. The cartridge was then eluted with 7 M ammonia-solution in MeOH and evaporated. The residue was purified for a second time by preparative HPLC (method B) and isolated in the same manner. The crude product was then recrystallised from a 1:1 mixtre of water/MeOH to give the title compound as a yellow crystalline solid. LCMS: $t_R$ 1.22 min and M+H=413.1 (method A3). $^1$H-NMR ($d_6$-DMSO, 400 MHz): 11.22 (s, 1H), 8.40 (s, 1H); 7.33 (s, br, 1H); 7.05 (s, br, 1H); 3.97-3.84 (m, 1H); 3.64-3.52 (m, 1H); 3.01-2.83 (m, 4H); 2.28-2.13 (m, 1H); 1.95-1.74 (m, 3H); 1.33 (s, 9H); 1.04-0.97 (m, 1H)).

EXAMPLE 19

(1S,5R)-2-Aza-bicyclo[3.1.0]hexane-1,2-dicarboxylic acid 1-amide 2-[(8-diethylamino-4,5-dihydro-thiazolo[4,5-h]quinazolin-2-yl)-amide]

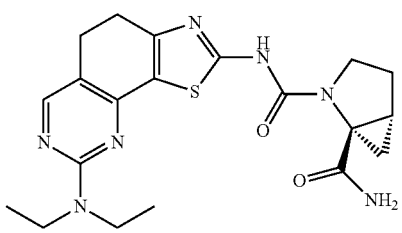 [SMILES: CCN(CC)c1ncc2c(n1)-c1sc(NC(=O)N3CC[C@@H]4C[C@@]43C(N)=O)nc1CC2]

To imidazole-1-carboxylic acid (8-diethylamino-4,5-dihydro-thiazolo[4,5-h]quinazolin-2-yl)-amide (Intermediate C, 75 mg, 0.203 mmol) in DCM (2 mL) was added (1S,5R)-2-aza-bicyclo[3.1.0]hexane-1-carboxylic acid amide (Intermediate O, 38.4 mg, 0.305 mmol) and triethylamine (0.085 mL, 0.609 mmol). The RM was stirred at 40° C. for 17.5 h and then directly purified by preparative HPLC (method B). The product containing fractions were eluted through a Bond Elut-SCX cartridge. The cartridge was then eluted with a 7 M solution of ammonia in MeOH and evaporated to give the title compound as a yellow solid. HPLC: $t_R$ 3.73 min (method D). MS: M+H=428.1.

EXAMPLE 20

(2S,3R)-3-Methyl-pyrrolidine-1,2-dicarboxylic acid 2-amide 1-[(8-tert-butyl-4,5-dihydro-thiazolo[4,5-h]quinazolin-2-yl)-amide]

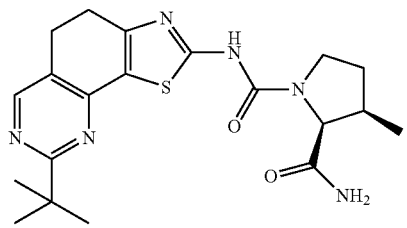 [SMILES: C[C@@H]1CCN(C(=O)Nc2nc3c(s2)-c2nc(C(C)(C)C)ncc2CC3)[C@@H]1C(N)=O]

To imidazole-1-carboxylic acid (8-tert-butyl-4,5-dihydro-thiazolo[4,5-h]quinazolin-2-yl)-amide (Intermediate A, 60 mg, 0.169 mmol) in DMF (1 mL) was added (2S,3R)-3-methyl-pyrrolidine-2-carboxylic acid amide (Intermediate P, 32.5 mg, 0.254 mmol) and triethylamine (0.071 mL, 0.508 mmol). The RM was stirred under argon for 2 h at rt and then directly purified by preparative HPLC (method B). The CH$_3$CN was evaporated from the product containing fractions and the remaining liquid then eluted through a Bond Elut-SCX cartridge. The cartridge was then eluted with a 7 M solution of ammonia in MeOH and evaporated. The residue was triturated in methanol and the title compound collected as white crystals following filtration and drying. HPLC: $t_R$ 3.66 (method D). MS: M+H=415.1. $^1$H-NMR (CD$_3$OD, 600 MHz): 7.96 (s, 1H), 4.04 (d, 1H), 3.47 (t, 1H), 3.18 (q, 1H), 2.71-2.67 (m, 2H), 2.64-2.58 (m, 2H), 2.24-2.15 (m, 1H), 1.76 (s, br, 1H), 1.53 (s, br, 1H), 1.03 (s, 9H), 0.78 (d, 3H).

EXAMPLE 21

(2S,3R)-3-Methyl-pyrrolidine-1,2-dicarboxylic acid 2-amide 1-[(8-diethylamino-4,5-dihydro-thiazolo[4,5-h]quinazolin-2-yl)-amide]

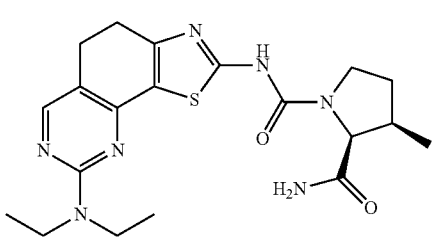 [SMILES: CCN(CC)c1ncc2c(n1)-c1sc(NC(=O)N3CC[C@@H](C)[C@H]3C(N)=O)nc1CC2]

To imidazole-1-carboxylic acid (8-diethylamino-4,5-dihydro-thiazolo[4,5-h]quinazolin-2-yl)-amide (Intermediate C, 82 mg, 0.222 mmol) in DMF (1.5 mL) was added under argon (2S,3R)-3-methyl-pyrrolidine-2-carboxylic acid amide (Intermediate P, 42.7 mg, 0.333 mmol) and triethylamine (0.093 mL, 0.666 mmol). The RM was stirred at rt for 2 h and then directly purified by preparative HPLC (method B). The CH₃CN was removed under vacuum from the product containing fractions and the remaining solution then eluted through a Bond Elut-SCX cartridge. The cartridge was then eluted with a 7 M ammonia solution in MeOH, evaporated and the residue triturated with methanol to give the title compound as a white crystalaline solid. HPLC: $t_R$ 3.74 (method D). MS: M+H=430.1. ¹H-NMR (CD₃OD, 600 MHz): 7.62 (s, 1H), 4.03 (d, 1H), 3.46 (t, 1H), 3.26 (q, 4H), 3.17 (q, 1H), 2.54 (s, 4H), 2.24-2.15 (m, 1H), 1.80-1.72 (m, 1H), 1.58-1.47 (m, 1H), 0.83 (t, 6H), 0.77 (d, 3H).

EXAMPLE 22

(2S,4S)-4-Dimethylamino-pyrrolidine-1,2-dicarboxylic acid 2-amide 1-[(8-diethylamino-4,5-dihydro-thiazolo[4,5-h]quinazolin-2-yl)-amide]

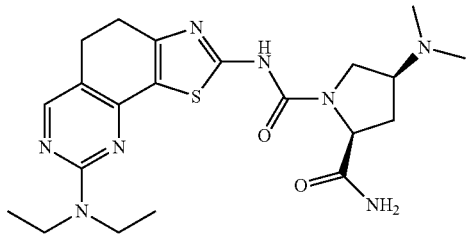 [SMILES: CCN(CC)c1ncc2c(n1)-c1sc(NC(=O)N3C[C@@H](N(C)C)C[C@H]3C(N)=O)nc1CC2]

To imidazole-1-carboxylic acid (8-diethylamino-4,5-dihydro-thiazolo[4,5-h]quinazolin-2-yl)-amide (Intermediate C, 60 mg, 0.162 mmol) in DMF (1.5 mL) was added (2S,4S)-4-dimethylamino-pyrrolidine-2-carboxylic acid amide (Intermediate Q, 28.1 mg, 0.179 mmol) and triethylamine (0.068 mL, 0.487 mmol). The RM was stirred at 40° C. for 17 h and then directly purified by preparative HPLC (method B). The product containing fractions were passed through a Bond Elut-SCX cartridge. The cartridge was then eluted with a 7 M ammonia solution in MeOH. The solution was evaporated to give the title compound. HPLC: $t_R$ 3.23 min (method D). MS: M+H=459.1.

EXAMPLE 23

5-Phenyl-pyrrolidine-1,2-dicarboxylic acid 2-amide 1-[(8-diethylamino-4,5-dihydro-thiazolo[4,5-h]quinazolin-2-yl)-amide]

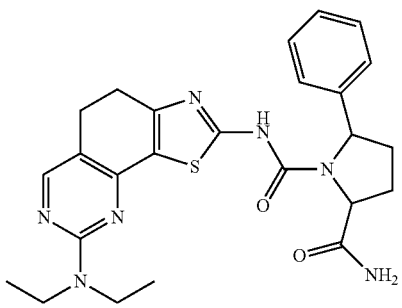 [SMILES: CCN(CC)c1ncc2c(n1)-c1sc(NC(=O)N3C(C(N)=O)CCC3c3ccccc3)nc1CC2]

To a suspension of imidazole-1-carboxylic acid (8-diethylamino-4,5-dihydro-thiazolo[4,5-h]quinazolin-2-yl)-amide (Intermediate C, 65 mg, 0.176 mmol) in DMF (2 mL) were added 5-phenyl-pyrrolidine-2-carboxylic acid amide (prepared as described in patent U.S. Pat. No. 3,164,597, Example 42, 50.2 mg, 0.264 mmol) and triethylamine (0.074 mL, 0.528 mmol). The RM was stirred at 40° C. for 2 h and then directly purified by preparative HPLC (method B). The product containing fractions were passed through a Bond Elut-SCX cartridge. The cartridge was then eluted with a 7 M ammonia solution in MeOH. The solution was evaporated and the residue was triturated in DCM to give the title compound as a yellow solid. LCMS: $t_R$ 0.99 min and M+H=492.0 (method A2).

EXAMPLE 24

Azetidine-1,2-dicarboxylic acid 2-amide 1-[(8-tert-butyl-4,5-dihydro-thiazolo[4,5-h]quinazolin-2-yl)-amide]

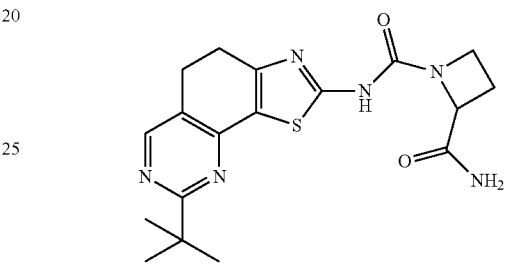

To a solution of imidazole-1-carboxylic acid (8-tert-butyl-4,5-dihydro-thiazolo[4,5-h]quinazolin-2-yl)-amide (Intermediate A, 100 mg, 0.282 mmol) in DMF (2 mL) were added azetidine-2-carboxylic acid amide (56.5 mg, 0.564 mmol) and triethylamine (0.118 mL, 0.846 mmol). The RM was stirred under argon atm. at rt for 16 h and then directly purified by preparative HPLC (method B). The product containing fractions were passed through a Bond Elut-SCX cartridge. The cartridge was then eluted with a 7 M ammonia solution in MeOH. The solution was evaporated and the residue purified by flash chromatography on silica gel, eluting with DCM/MeOH 95:5 containing 0.5% 880 HN₃ to give the title compound as a yellow solid. HPLC: $t_R$ 3.55 min (method D). MS: M+H=387.1.

EXAMPLE 25

(S)-Azetidine-1,2-dicarboxylic acid 2-amide 1-[(8-tert-butyl-4,5-dihydro-thiazolo[4,5-h]quinazolin-2-yl)-amide]

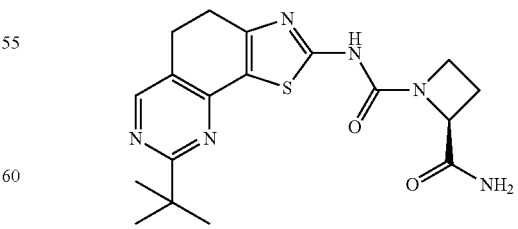

(S)-Azetidine-2-carboxylic acid amide (Intermediate L, 68.1 mg, 0.680 mmol) was added to a stirred mixture of imidazole-1-carboxylic acid (8-tert-butyl-4,5-dihydro-thiazolo[4,5-h]quinazolin-2-yl)-amide (Intermediate A, 241 mg, 0.680 mmol) and triethylamine (0.284 mL, 2.040 mmol) in DMF (3 mL) at rt. The RM was allowed to stand 66 h at rt and then directly purified by preparative HPLC (method B). The product containing fractions were evaporated to remove the CH₃CN and then basified with NaHCO₃. The aqueous phase was then extracted 4× with 10% MeOH in DCM, the combined organic layers dried over Na₂SO₄ and evaporated to give a solid which was triturated with MeOH/water to give the title compound as an off-white crystaline solid. LCMS: $t_R$ 1.08 min and M+H=386.9 (method A3).

EXAMPLE 26

(2S,4S)-4-Hydroxy-pyrrolidine-1,2-dicarboxylic acid 2-amide 1-[(8-diethylamino-4,5-dihydro-thiazolo[4,5-h]quinazolin-2-yl)-amide]

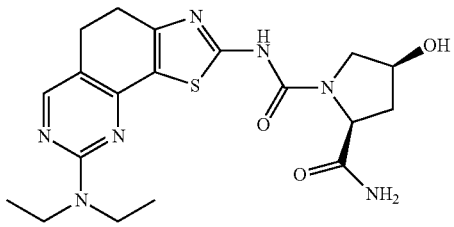 [SMILES: CCN(CC)c1ncc2c(n1)-c1sc(NC(=O)N3C[C@@H](O)C[C@H]3C(N)=O)nc1CC2]

To a suspension of imidazole-1-carboxylic acid (8-diethylamino-4,5-dihydro-thiazolo[4,5-h]quinazolin-2-yl)-amide (Intermediate C, 75 mg, 0.203 mmol) in DMF (2 mL) were added (2S,4S)-4-hydroxy-pyrrolidine-2-carboxylic acid amide (Intermediate R, 39.6 mg, 0.305 mmol) and triethylamine (0.113 mL, 0.812 mmol). The RM was stirred at 40° C. for 2.5 h and then directly purified by preparative HPLC (method B). The product containing fractions were passed through a Bond Elut-SCX cartridge. The cartridge was then eluted with a 7 M ammonia solution in MeOH. The solution was evaporated to give the title compound as a yellow solid. HPLC: $t_R$ 3.44 min (method D). MS: M+H=432.1.

EXAMPLE 27

(2S,4R)-4-Hydroxy-pyrrolidine-1,2-dicarboxylic acid 2-amide 1-[(8-diethylamino-4,5-dihydro-thiazolo[4,5-h]quinazolin-2-yl)-amide]

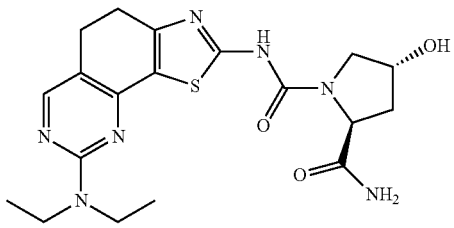 [SMILES: CCN(CC)c1ncc2c(n1)-c1sc(NC(=O)N3C[C@H](O)C[C@H]3C(N)=O)nc1CC2]

To a suspension of imidazole-1-carboxylic acid (8-diethylamino-4,5-dihydro-thiazolo[4,5-h]quinazolin-2-yl)-amide (Intermediate C, 75 mg, 0.203 mmol) in DMF (2 mL) were added (2S,4R)-4-hydroxy-pyrrolidine-2-carboxylic acid amide (Intermediate S, 39.6 mg, 0.305 mmol) and triethylamine (0.113 mL, 0.812 mmol). The RM was stirred at 40° C. for 4.5 h and then directly purified by preparative HPLC (method B). The product containing fractions were passed through a Bond Elut-SCX cartridge. The cartridge was then eluted with a 7 M ammonia solution in MeOH. The solution was evaporated and the residue was recrystallised from DCM to give the title compound as a yellow solid. HPLC: $t_R$ 3.31 min (method D). MS: M+H=432.1.

EXAMPLE 28

(S)-Pyrrolidine-1,2-dicarboxylic acid 2-amide 1-[(7-tert-butyl-4,5-dihydro-benzo[1,2-d;3,4-d']bisthiazol-2-yl)-amide]

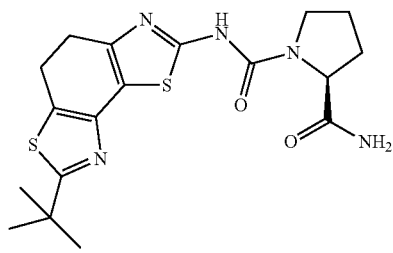 [SMILES: CC(C)(C)c1nc2c(s1)CCc1nc(NC(=O)N3CCC[C@H]3C(N)=O)sc1-2]

L-Prolinamide (59.4 mg, 0.521 mmol) and TEA (0.121 mL, 0.868 mmol) were added to imidazole-1-carboxylic acid (7-tert-butyl-4,5-dihydro-benzo[1,2-d;3,4-d']bisthiazol-2-yl)-amide (Intermediate T, 156 mg, 0.434 mmol) in DMF (1 mL). The RM was stirred at rt for 10 min. The mixture was extracted with EtOAc/H₂O. The organic layer was dried over Na2SO4 and evaporated. The crude material was chromatographied with MPLC C18 H₂O 0.1% TFA/CH₃CN 0.1% TFA, gradient 0-50%. Product containing fractions were neutralized with NaHCO₃, extracted with EtOAc and lyophilized from dioxane to give the title compound as a white solid (M+H=406; M–H=404; $t_R$ 4.75 min (Method F). ¹H-NMR (d₆-DMSO, 600.13 MHz) 10.80 (s, 1H) 7.40 (s, 1H), 6.98 (s, 1H), 4.30 (s, 1H) 3.65-3.55 (m 1H), 3.48-3.38 (m, 1H), 3.10 (t, 2H), 2.94 (t, 2H), 2.14-2.05 (m, 1H), 1.95-1.78 (m, 3H), 1.40 (s, 9H)).

EXAMPLE 29

(S)-2-Methyl-pyrrolidine-1,2-dicarboxylic acid 2-amide 1-[(7-tert-butyl-4,5-dihydro-benzo[1,2-d;3,4-d']bisthiazol-2-yl)-amide]

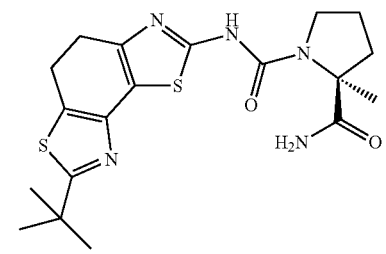 [SMILES: CC(C)(C)c1nc2c(s1)CCc1nc(NC(=O)N3CCC[C@@]3(C)C(N)=O)sc1-2]

(S)-2-Methyl-pyrrolidine-2-carboxylic acid amide (Intermediate F, 7.7 mg, 0.060 mmol) and TEA (0.014 mL, 0.100 mmol) were added to imidazole-1-carboxylic acid (7-tert-butyl-4,5-dihydro-benzo[1,2-d;3,4-d']bisthiazol-2-yl)-amide (Intermediate T, 18 mg, 0.050 mmol) in DMF (3 mL). The RM was stirred at rt for 10 min. then extracted with EtOAc/H$_2$O. The organic layer was dried over Na$_2$SO$_4$ and evaporated. The crude material was chromatographied with MPLC C18 H$_2$O 0.1% TFA/CH$_3$CN 0.1% TFA, gradient 0-50%. Product containing fractions were neutralized with NaHCO$_3$, extracted with EtOAc and lyophilized from dioxane to give the title compound as a white solid (M+H=420; M−H=418; t$_R$ 4.875 min (Method F). $^1$H-NMR (d$_6$-DMSO, 600.13 MHz) 10.60 (s, br, 1H) 7.68 (s, 1H), 6.86 (s, 1H), 3.68-3.60 (m 1H), 3.60-3.50 (m 1H), 3.08 (t, 2H), 2.90 (t, 2H), 2.10-1.98 (m, 1H), 1.90-1.68 (m, 3H), 1.48 (s, 3H), 1.37 (s, 9H)).

EXAMPLE 30

(S)-Azetidine-1,2-dicarboxylic acid 2-amide 1-[(7-tert-butyl-4,5-dihydro-benzo[1,2-d;3,4-d']bisthiazol-2-yl)-amide]

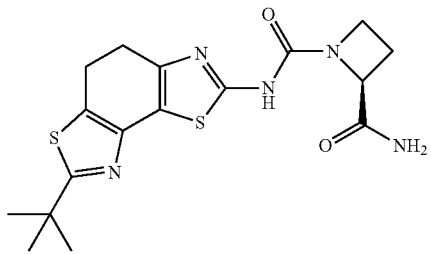 [SMILES: CC(C)(C)c1nc2c(s1)CCc1nc(NC(=O)N3CC[C@H]3C(N)=O)sc1-2]

(S)-Azetidine-2-carboxylic acid amide (Intermediate L, 37.1 mg, 0.370 mmol) and TEA (0.14 mL, 1.010 mmol) were added to imidazole-1-carboxylic acid (7-tert-butyl-4,5-dihydro-benzo[1,2-d;3,4-d']bisthiazol-2-yl)-amide (Intermediate T, 121 mg, 0.337 mmol) in DMF (2 mL). The RM was stirred for 5 min and then stood for 2 days at rt. The RM was filtered and directly purified by Prep.HPLC (method E). Product containing fractions were combined and filtered through a Bond Elute-SCX, 300 mg cartridge. The cartridge was then washed with 7 M ammonia-solution in MeOH (2 ml). The filtrate was evaporated to give the title compound as a white solid (M+H=391.8; M−H=389.8; t$_R$ 1.84 min (Method A3). $^1$H-NMR (d$_6$-DMSO, 400 MHz) 11.12 (s, 1H) 7.52 (s, 1H), 7.30 (s, 1H), 4.74-4.62 (m, 1H), 3.92 (t, 2H), 3.08 (t, 2H), 2.90 (t, 2H), 2.46-2.36 (m, 1H), 2.18-2.02 (m, 1H), 1.39 (s, 9H)).

EXAMPLE 31

(2S,4R)-4-Dimethylamino-pyrrolidine-1,2-dicarboxylic acid 2-amide 1-[(7-tert-butyl-4,5-dihydro-benzo[1,2-d;3,4-d']bisthiazol-2-yl)-amide]

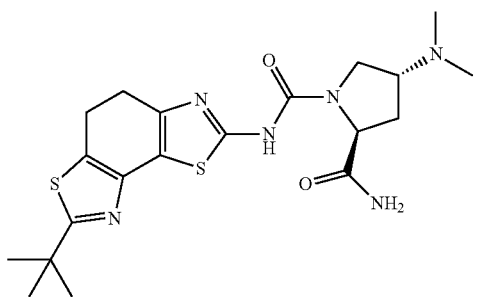 [SMILES: CN(C)[C@@H]1C[C@@H](C(N)=O)N(C(=O)Nc2nc3c(s2)-c2nc(C(C)(C)C)sc2CC3)C1]

(2S,4R)-4-Dimethylamino-pyrrolidine-2-carboxylic acid amide (Intermediate B, 9.33 mg, 0.059 mmol) and TEA (0.019 ml, 0.135 mmol) were added to imidazole-1-carboxy-lic acid (7-tert-butyl-4,5-dihydro-benzo[1,2-d;3,4-d']bisthiazol-2-yl)-amide (Intermediate T, 19.4 mg, 0.054 mmol) in DMF (1 ml). The RM was stirred for 5 min and then stood overnight at rt. The RM was filtered and directly purified by Prep.HPLC (method E). Fractions containing the product were combined and filtered through a Bond Elute-SCX, 300 mg cartridge. The cartridge was then washed with 7 M ammonia-solution in MeOH. The filtrate was evaporated to give the title compound as a white solid (M+H=449.1; M−H=447.3; t$_R$ 1.47 min (Method A3). $^1$H-NMR (d$_6$-DMSO, 400 MHz) 7.40 (s, 1H), 7.00 (s, 1H), 4.44-4.25 (m, 1H), 3.86-3.76 (m 1H), 3.35-3.25 (m 1H), 3.08 (t, 2H), 2.92 (t, 2H), 2.96-2.78 (m, 1H), 1.18 (s, br, 6H), 2.08-1.85 (m, 2H), 1.38 (s, 9H)).

EXAMPLE 32

(S)-Pyrrolidine-1,2-dicarboxylic acid 2-amide 1-{[7-(2-fluoro-1,1-dimethyl-ethyl)-4,5-dihydro-benzo[1,2-d;3,4-d']bisthiazol-2-yl]-amide}

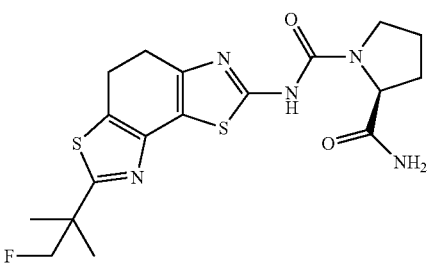 [SMILES: CC(C)(CF)c1nc2c(s1)CCc1nc(NC(=O)N3CCC[C@H]3C(N)=O)sc1-2]

L-Prolinamide (23.98 mg, 0.210 mmol) and TEA (0.080 mL, 0.573 mmol) were added to imidazole-1-carboxylic acid [7-(2-fluoro-1,1-dimethyl-ethyl)-4,5-dihydro-benzo[1,2-d;3,4-d']bisthiazol-2-yl]-amide (Intermediate U, 72.1 mg, 0.191 mmol) in DMF (1 mL). The RM was stirred for 5 min and then stood overnight at rt. The RM was evaporated and then triturated with MeOH (2 mL) and H$_2$O (1 mL). The mixture was cooled to 4° C. The suspension was filtered and washed with cold MeOH/H$_2$O=2:1 and the solid dried under HV at 40° C. to give the title compound as a white solid (M+H=424.0; M−H=422.1; t$_R$ 1.7 min (Method A3). $^1$H-NMR (d$_6$-DMSO, 400 MHz) 7.19 (s, 1H), 6.96 (s, 1H), 4.58 (s, 1H), 4.44 (s, 1H), 4.28 (s, br, 1H) 3.64-3.50 (m 1H), 3.48-3.38 (m 1H), 3.10 (t, 2H), 2.92 (t, 2H), 2.18-1.98 (m, 1H), 1.94-1.78 (m, 3H), 1.38 (s, 6H) $^{19}$F-NMR (d6-DMSO, 600.13 MHz) 219 ppm (t, 1F)).

EXAMPLE 33

(S)-Pyrrolidine-1,2-dicarboxylic acid 2-amide 1-[(7-cyclopropylmethyl-4,5-dihydro-benzo[1,2-d;3,4-d']bisthiazol-2-yl)-amide]

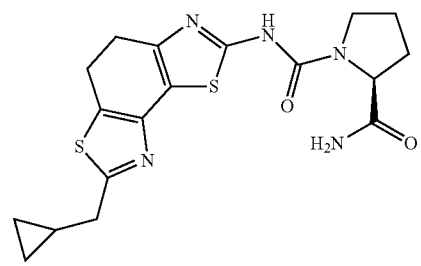 [SMILES: NC(=O)[C@@H]1CCCN1C(=O)Nc1nc2c(s1)-c1nc(CC3CC3)sc1CC2]

L-Prolinamide (16.7 mg, 0.147 mmol) and TEA (0.027 mL, 0.196 mmol) were added to imidazole-1-carboxylic acid (7-cyclopropylmethyl-4,5-dihydro-benzo[1,2-;3,4-d'] bisthiazol-2-yl)-amide (Intermediate V, 35 mg, 0.098 mmol) in DMF (1.5 mL). The RM was stirred at rt for 15 min and then extracted with EtOAc/H$_2$O. The organic layer was dried over Na$_2$SO$_4$ and evaporated. The crude material was chromatographied with MPLC C18 H$_2$O 0.1% TFA/CH$_3$CN 0.1% TFA, gradient 0-50%. Product containing fractions were neutralized with NaHCO$_3$, extracted with EtOAc and lyophilized from dioxane to give the title compound as a white solid (M+H=404; M−H=402; $t_R$ 4.49 min (Method F). $^1$H-NMR (d$_6$-DMSO, 600.13 MHz) 10.78 (s, 1H) 7.40 (s, 1H), 6.98 (s, 1H), 4.28 (s, br, 1H) 3.65-3.55 (m, 1H), 3.48-3.38 (m, 1H), 3.08 (t, 2H), 2.97 (t, 2H), 2.84 (d, 2H), 2.14-2.04 (m, 1H), 1.93-1.72 (m, 3H), 1.10 (q, 1H), 0.60-0.50 (m, 2H), 0.40-0.38 (m, 2H)).

EXAMPLE 34

(2S,3S)-3-Methyl-pyrrolidine-1,2-dicarboxylic acid 2-amide 1-[(7-tert-butyl-4,5-dihydro-benzo[1,2-d;3,4-d']bisthiazol-2-yl)-amide]

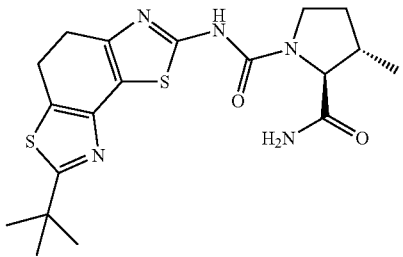 [SMILES: C[C@H]1CCN(C(=O)Nc2nc3c(s2)-c2nc(C(C)(C)C)sc2CC3)[C@@H]1C(N)=O]

(2S,3S)-3-Methyl-pyrrolidine-2-carboxylic acid amide (Intermediate D, 13.37 mg, 0.104 mmol) and TEA (0.039 mL, 0.278 mmol) were added to imidazole-1-carboxylic acid (7-tert-butyl-4,5-dihydro-benzo[1,2-d;3,4-d']bisthiazol-2-yl)-amide (Intermediate T, 25 mg, 0.070 mmol) in DMF (2 mL). The RM was stirred at rt for 10 min and then extracted with EtOAc/H$_2$O. The organic layer was dried over Na$_2$SO$_4$ and evaporated. The crude material was lyophilized from dioxane without further purification to give the title compound as a white solid (M+H=420.1; M−H=418.1; $t_R$ 4.85 min (Method F). $^1$H-NMR (d$_6$-DMSO, 600.13 MHz) 10.78 (s, br, 1H) 7.44 (s, br, 1H), 6.97 (s, br, 1H), 3.90-3.70 (m, 1H) 3.62-3.42 (m, 2H), 3.08 (t, 2H), 2.94 (t, 2H), 2.22-2.12 (m, 1H), 2.06-1.94 (m, 1H), 1.58-1.48 (m, 1H), 1.39 (s, 9H), 1.04 (d, 3H)).

EXAMPLE 35

(1S,5R)-2-Aza-bicyclo[3.1.0]hexane-1,2-dicarboxylic acid 1-amide 2-[(7-tert-butyl-4,5-dihydro-benzo[1,2-d;3,4-d']bisthiazol-2-yl)-amide]

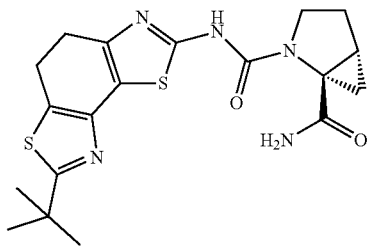 [SMILES: CC(C)(C)c1nc2c(s1)CCc1nc(NC(=O)N3CC[C@@H]4C[C@@]43C(N)=O)sc1-2]

The title compound was synthesized in a similar manner as described for Example 34 using intermediate O instead of intermediate D.

(M+H=418.0; M−H=416.1; $t_R$ 4.90 min (Method F). $^1$H-NMR (d$_6$-DMSO, 600.13 MHz) 10.78 (s, br, 1H) 7.40 (s, br, 1H), 7.06 (s, br, 1H), 3.92-3.82 (m, 1H) 3.62-3.52 (m, 1H), 3.08 (t, 2H), 2.94 (t, 2H), 2.26-2.14 (m, 1H), 1.92-1.72 (m, 3H), 1.39 (s, 9H), 1.05-0.95 (m, 1H)).

EXAMPLE 36

(2S,3S)-3-(Acetylamino-methyl)-pyrrolidine-1,2-dicarboxylic acid 2-amide 1-[(8-tert-butyl-4,5-dihydro-thiazolo[4,5-h]quinazolin-2-yl)-amide]

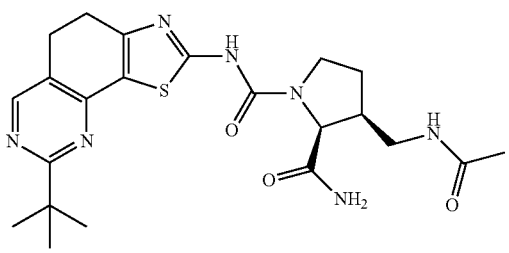 [SMILES: CC(=O)NC[C@@H]1CCN(C(=O)Nc2nc3c(s2)-c2nc(C(C)(C)C)ncc2CC3)[C@@H]1C(N)=O]

Triethylamine (0.339 mmol) was added to a solution of imidazole-1-carboxylic acid (8-tert-butyl-4,5-dihydro-thiazolo[4,5-h]quinazolin-2-yl)-amide (Intermediate A) (0.113 mmol) and (2S,3S)-3-(acetylamino-methyl)-pyrrolidine-2-carboxylic acid amide (Stage 36.1) (0.135 mmol) at rt. After stirring for 85 min, the reaction mixture was concentrated. The residue was purified by silica gel column chromatography followed by trituration with Et$_2$O to afford the title compound as a yellow solid. HPLC: $t_R$=4.20 min (method H); LCMS: $t_R$=1.48 min, [M+H]$^+$ 472 (method I); TLC: $R_f$=0.14 (9:1 CH$_2$Cl$_2$/MeOH); $^1$H-NMR (d$_6$-DMSO, 600 MHz): 11.15 (br s, 1H), 8.41 (s, 1H), 7.81 (br s, 1H), 7.53 (br s, 1H), 7.13 (br s, 1H), 4.28 (m, 1H), 3.74 (m, 1H), 3.40 (m, 1H), 3.25 (m, 1H), 2.98 (m, 2H), 2.93 (m, 3H), 2.42 (m, 1H), 2.02 (m, 1H), 1.82 (s, 3H), 1.74 (m, 1H), 1.33 (s, 9H).

Stage 36.1: (2S,3S)-3-(Acetylamino-methyl)-pyrrolidine-2-carboxylic acid amide

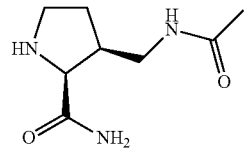

A mixture of (2S,3S)-3-(acetylamino-methyl)-1-((S)-1-phenyl-ethyl)-pyrrolidine-2-carboxylic acid amide (Stage 36.2) (0.48 mmol) and 10% Pd on charcoal, wet with 50% H$_2$O (Aldrich 330108) (0.096 mmol) in MeOH (5 mL) was hydrogenated for 6.5 h at rt. The reaction mixture was then filtered through a Fluoropore Membrane Filter (0.2 μm FG) and evaporated. The residue was dissolved in CH$_2$Cl$_2$ and evaporated to dryness to afford the title compound as an off-white solid. ESI-MS: [M+H]$^+$ 186; TLC: R$_f$=0.08 (200:20:1 CH$_2$Cl$_2$/MeOH/conc. NH$_4$OH).

Stage 36.2: (2S,3S)-3-(Acetylamino-methyl)-1-((S)-1-phenyl-ethyl)-pyrrolidine-2-carboxylic acid amide

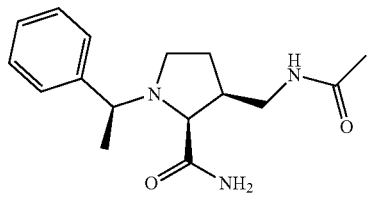 [SMILES: CC(=O)NC[C@@H]1CCN([C@@H](C)c2ccccc2)[C@@H]1C(N)=O]

Thioacetic acid (2.312 mmol) was added to (2S,3S)-3-azidomethyl-1-((S)-1-phenyl-ethyl)-pyrrolidine-2-carboxylic acid amide (Stage 36.3) (0.578 mmol) at rt with the formation of nitrogen gas. After stirring for 16 h, the reaction mixture was diluted with Et$_2$O, the solids were removed by filtration and the filtrate was concentrated. The residue was purified by silica gel column chromatography to afford the title compound as a light yellow oil (thiol odor). HPLC: t$_R$=3.71 min (method H); LC-MS: t$_R$=0.64 min, [M+H]$^+$ 290 (method I); TLC: R$_f$=0.38 (200:20:1 CH$_2$Cl$_2$/MeOH/conc. NH$_4$OH).

Stage 36.3: (2S,3S)-3-Azidomethyl-1-((S)-1-phenyl-ethyl)-pyrrolidine-2-carboxylic acid amide

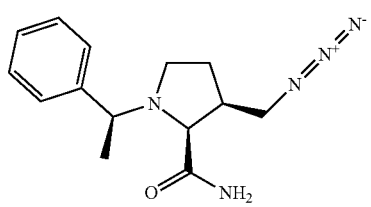 [SMILES: C[C@@H](c1ccccc1)N1CC[C@@H](CN=[N+]=[N-])[C@H]1C(N)=O]

Trimethylaluminum in toluene (2 M, 15.95 mmol) was added dropwise to a mixture of NH$_4$Cl (15.95 mmol) in toluene (2 mL) at 0° C. with the formation of methane gas. The reaction mixture was allowed to warm to rt, stirred for a further 15 min and then slowly treated with a solution of (2S,3S)-3-azidomethyl-1-((S)-1-phenyl-ethyl)-pyrrolidine-2-carboxylic acid methyl ester (Stage 36.4) (7.98 mmol) in toluene (8 mL). Additional reagent prepared from NH$_4$Cl (15.95 mmol) in toluene (2 mL) and trimethylaluminum in toluene (2 M, 15.95 mmol) at 0° C. was added after 18 h. After stirring for 44 h, the mixture was cooled to 0° C., quenched with 1M HCl and then washed with CH$_2$Cl$_2$ (3×). The aqueous phase was basified with a 1:1 saturated solution of NaHCO$_3$/saturated solution of Rochelle's salt and extracted with THF (10×). The combined organic layers were dried (Na$_2$SO$_4$), filtered and concentrated. The residue was purified using a RediSep® silica gel column to afford the title compound as a yellow oil. HPLC: t$_R$=2.50 min (method G); ESI-MS: [M+H]$^+$ 274; TLC: R$_f$=0.26 (3:1 Hex/EtOAc).

Stage 36.4: (2S,3S)-3-Azidomethyl-1-((S)-1-phenyl-ethyl)-pyrrolidine-2-carboxylic acid methyl ester

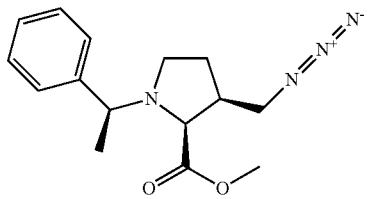 [SMILES: COC(=O)[C@@H]1[C@H](CN=[N+]=[N-])CCN1[C@@H](C)c1ccccc1]

Sodium azide (5.34 mmol) was added to a solution of (2S,3R)-3-iodomethyl-1-((S)-1-phenyl-ethyl)-pyrrolidine-2-carboxylic acid methyl ester (Stage 36.5) (3.56 mmol) in DMF (30 mL) at rt. After 18 h, the reaction mixture was poured onto water and extracted with MTBE (2×). The combined organic phases were washed with brine, dried (Na$_2$SO$_4$), filtered and concentrated. The residue was purified using a RediSep° silica gel column to to afford the title compound as a brown oil. HPLC: t$_R$=3.26 min (method G); ESI-MS: [M+H]$^+$ 289.

Stage 36.5: (2S,3R)-3-Iodomethyl-1-((S)-1-phenyl-ethyl)-pyrrolidine-2-carboxylic acid methyl ester

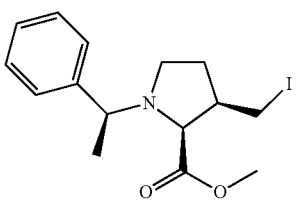 [SMILES: COC(=O)[C@@H]1[C@H](CI)CCN1[C@@H](C)c1ccccc1]

A solution of [but-3-enyl-((S)-1-phenyl-ethyl)-amino]-acetic acid methyl ester [432555-77-6] (20.22 mmol) in THF (10 mL) was slowly added to a solution of lithium diisopropylamide (24.26 mmol) in 1:2 hexanes/THF (30 mL) at −78° C. The reaction mixture was warmed to 0° C., stirred for 1 h and then re-cooled to −78° C. A solution of zinc bromide (50.5 mmol) in Et$_2$O (40 mL) was added and the reaction mixture was then warmed to rt. After stirring for 1 h, the mixture was cooled to 0° C. and iodine (22.24 mmol) was added in portions. The reaction mixture was stirred at 0° C. for 2 h and at rt for another 2 h, diluted with Et$_2$O and then successively washed with a saturated solution of Na$_2$S$_2$O$_3$ and a saturated solution of NH$_4$Cl. The aqueous layers were each back-extracted with Et$_2$O. The combined organic phases were dried (Na$_2$SO$_4$), filtered and concentrated. The residue was purified by silica gel column chromatography to afford the title compound as a red oil. HPLC: $t_R$=3.46 min (method G); ESI-MS: [M+H]$^+$ 374.

EXAMPLE 37

(2S,3S)-3-Morpholin-4-ylmethyl-pyrrolidine-1,2-dicarboxylic acid 2-amide 1-[(8-tert-butyl-4,5-dihydro-thiazolo[4,5-h]quinazolin-2-yl)-amide]

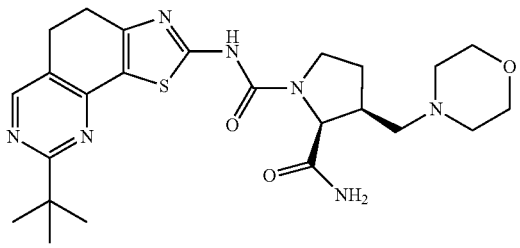 [SMILES: CC(C)(C)c1ncc2c(n1)-c1sc(NC(=O)N3CC[C@@H](CN4CCOCC4)[C@H]3C(N)=O)nc1CC2]

Triethylamine (0.423 mmol) was added to a solution of imidazole-1-carboxylic acid (8-tert-butyl-4,5-dihydro-thiazolo[4,5-h]quinazolin-2-yl)-amide (Intermediate A) (0.141 mmol) and (2S,3S)-3-(acetylamino-methyl)-pyrrolidine-2-carboxylic acid amide (Stage 37.1) (0.155 mmol) in DMF (0.5 mL) at rt. After stirring for 3 h, the reaction mixture was concentrated. The residue was purified by silica gel column chromatography to afford the title compound as a white solid. HPLC: $t_R$=4.04 min (method H); LCMS: $t_R$=1.36 min, [M+H]$^+$ 500 (method I); TLC: $R_f$=0.09 (19:1 CH$_2$Cl$_2$/MeOH); $^1$H-NMR (d$_6$-DMSO, 600 MHz): 11.15 (br s, 1H), 8.39 (m, 1H), 7.37 (br s, 1H), 7.05 (s, 1H), 4.27 (m, 1H), 3.70 (m, 1H), 3.59 (m, 4H), 3.42 (m, 1H), 2.97 (m, 2H), 2.90 (m, 2H), 2.58 (m, 1H), 2.38 (m, 4H), 2.35 (m, 1H), 2.17 (m, 1H), 2.02 (m, 1H), 1.75 (m, 1H), 1.32 (s, 9H).

less oil. ESI-MS: [M+H]$^+$ 214; TLC: $R_f$=0.14 (200:20:1 CH$_2$Cl$_2$/MeOH/conc. NH$_4$OH).

Stage 37.2: (2S,3S)-3-Morpholin-4-ylmethyl-1-((S)-1-phenyl-ethyl)-pyrrolidine-2-carboxylic acid amide

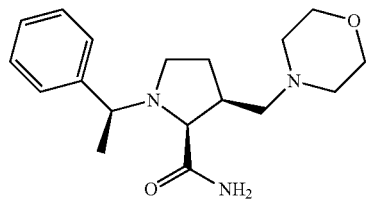 [SMILES: C[C@@H](c1ccccc1)N1CC[C@@H](CN2CCOCC2)[C@H]1C(N)=O]

Trimethylaluminum in toluene (2 M, 2.89 mmol) was added dropwise to a mixture of NH$_4$Cl (2.89 mmol) in toluene (3 mL) at 0° C. with the formation of methane gas. The reaction mixture was allowed to warm to rt, stirred for a further 15 min and then slowly treated with a solution of (2S,3S)-3-morpholin-4-ylmethyl-1-((S)-1-phenyl-ethyl)-pyrrolidine-2-carboxylic acid methyl ester (Stage 37.3) (1.444 mmol) in toluene (9 mL). Additional reagent prepared from NH$_4$Cl (2.89 mmol) in toluene (2 mL) and trimethylaluminum in toluene (2 M, 2.89 mmol) at 0° C. was added after 18 h. After stirring for 60 h, the mixture was cooled to 0° C., quenched with 1M HCl and then washed with CH$_2$Cl$_2$ (3×). The aqueous phase was basified with a 1:1 saturated solution of NaHCO$_3$/saturated solution of Rochelle's salt and extracted with THF (10×). The combined organic layers were dried (Na$_2$SO$_4$), filtered and concentrated. The residue was purified by silica gel column chromatography to afford the title compound as a yellow oil. HPLC: $t_R$=2.18 min (method G); ESI-MS: [M+H]$^+$ 318.

Stage 37.1: (2S,3S)-3-Morpholin-4-ylmethyl-pyrrolidine-2-carboxylic acid amide

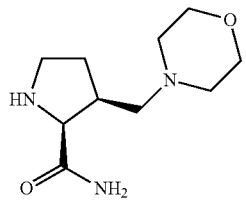

A mixture of (2S,3S)-3-morpholin-4-ylmethyl-1-((S)-1-phenyl-ethyl)-pyrrolidine-2-carboxylic acid amide (Stage 37.2) (1.046 mmol) and 10% Pd on charcoal, wet with 50% H$_2$O (Aldrich 330108) (0.105 mmol) in MeOH (5 mL) was hydrogenated for 6.5 h at rt. The reaction mixture was then filtered through a Fluoropore Membrane Filter (0.2 µm FG) and evaporated. The residue was dissolved in CH$_2$Cl$_2$ and evaporated to dryness to afford the title compound as color- Stage 37.3: (2S,3S)-3-Morpholin-4-ylmethyl-1-((S)-1-phenyl-ethyl)-pyrrolidine-2-carboxylic acid methyl ester

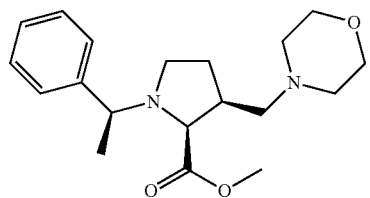 [SMILES: COC(=O)[C@@H]1[C@H](CN2CCOCC2)CCN1[C@@H](C)c1ccccc1]

A mixture of (2S,3R)-3-iodomethyl-1-((S)-1-phenyl-ethyl)-pyrrolidine-2-carboxylic acid methyl ester (Stage 36.5) (7.07 mmol), K$_2$CO$_3$ (21.22 mmol) and morpholine (10.61 mmol) in CH$_3$CN (24 mL) was stirred at 50° C. for 62 h. The reaction mixture was poured onto ice water and extracted with EtOAc (3×). The combined organic layers were successively washed with water and brine, dried (Na$_2$SO$_4$), filtered and concentrated. The residue was purified using a RediSep® silica gel column to afford the title compound as a yellow oil. HPLC: $t_R$=2.56 min (method G); ESI-MS: [M+H]$^+$ 333.

EXAMPLE 38

(2S,3R)-3-Hydroxy-pyrrolidine-1,2-dicarboxylic acid 2-amide 1-[(8-tert-butyl-4,5-dihydro-thiazolo[4,5-h]quinazolin-2-yl)-amide]

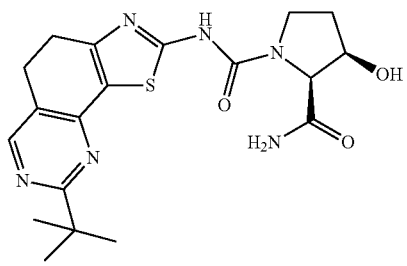 [SMILES: CC(C)(C)c1ncc2c(n1)-c1sc(NC(=O)N3CC[C@@H](O)[C@H]3C(N)=O)nc1CC2]

The title compound was synthesized using methodology as described for Example 20 using (2S,3R)-3-hydroxy-pyrrolidine-2-carboxylic acid amide (H. Fukushima et al. Bioorg. Med. Chem. 2004, 12, 6053; H. Ji et al. J. Med. Chem. 2006, 49(21), 6254) instead of intermediate P.

LCMS: $t_R$=1.45 min, M+H=417.0, M−H=415 (method J). $^1$H-NMR (d$_6$-DMSO, 600.13 MHz): 12-11 (s, br, 1H) 8.4 (s, 1H), 7.2-6.9 (m, 2H), 5.2 (s, 1H), 4.4 (s, 1H), 4.25 (s, br, 1H), 3.6 (m, 1H); 3.45 (m, 1H), 2.95 (m, 2H), 2.9 (m, 2H), 2.0 (m, 1H), 1.9 (m, 1H), 1.3 (s, 9H).

EXAMPLE 39

(2S,3R)-3-Methyl-pyrrolidine-1,2-dicarboxylic acid 2-amide 1-[(7-tert-butyl-4,5-dihydro-benzo[1,2-d;3,4-d']bisthiazol-2-yl)-amide]

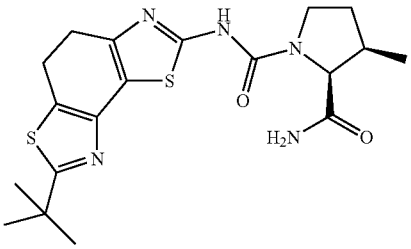 [SMILES: C[C@@H]1CCN(C(=O)Nc2nc3c(s2)-c2nc(C(C)(C)C)sc2CC3)[C@@H]1C(N)=O]

The title compound was synthesized using methodology as described for Example 34 using (2S,3R)-3-methyl-pyrrolidine-2-carboxylic acid amide (intermediate P) instead of intermediate D.

LCMS: $t_R$=1.32 min, M+H=420.0, M−H=418.1 (method J). $^1$H-NMR (d$_6$-DMSO, 400 MHz): 10.65 (s, br, 1H) 7.39 (s, br, 1H), 6.99 (s, br, 1H), 4.2 (m, 1H), 3.67 (t, 1H), 3.3 (m, 1H), 3.08 (t, 2H), 2.93 (t, 2H), 2.38 (m, 1H), 1.95 (m, 1H), 1.7 (m, 1H), 1.39 (s, 9H), 0.97 (d 3H).

Synthesis Scheme:

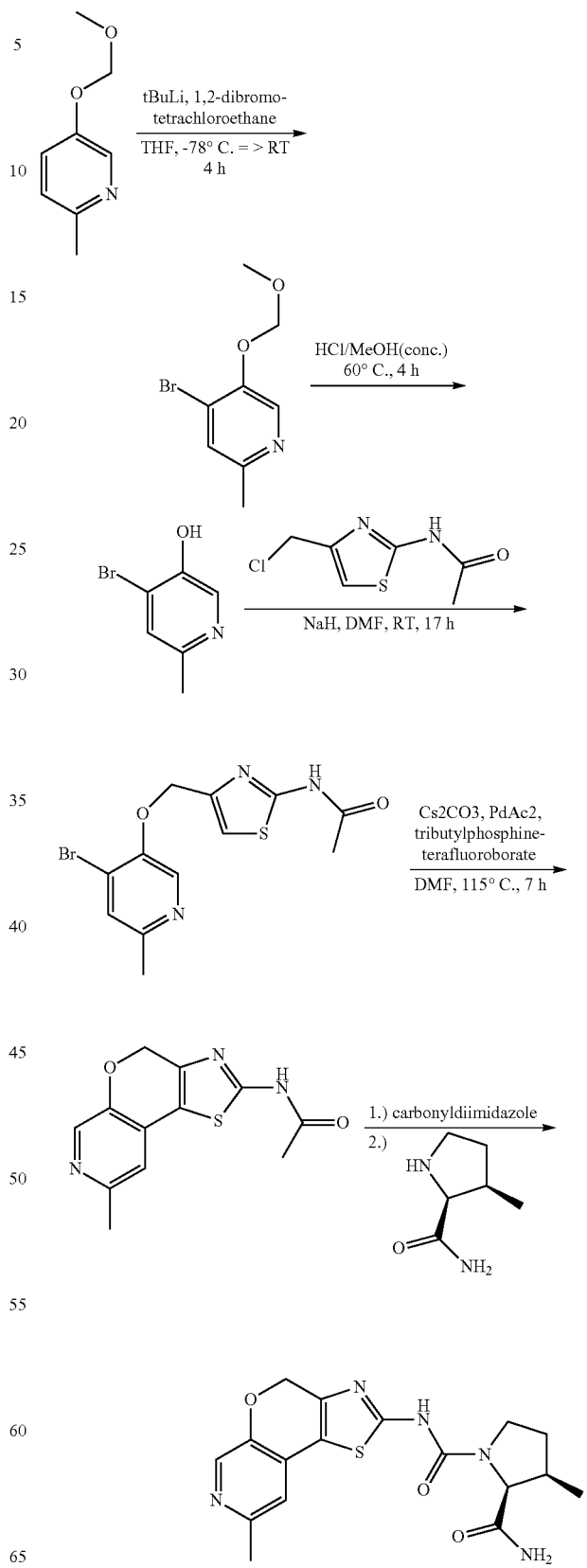

EXAMPLE 40

(2S,3R)-3-Methyl-pyrrolidine-1,2-dicarboxylic acid 2-amide 1-[(8-methyl-4H-5-oxa-1-thia-3,7-diaza-cyclopenta[a]naphthalen-2-yl)-amide]

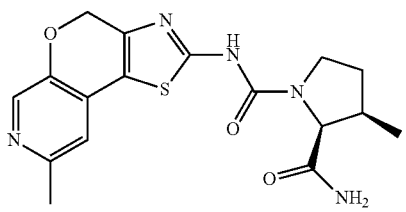 [SMILES: Cc1cc2c(cn1)OCc1nc(NC(=O)N3CC[C@@H](C)[C@H]3C(N)=O)sc1-2]

The title compound was prepared starting from imidazole-1-carboxylic acid (8-methyl-4H-5-oxa-1-thia-3,7-diaza-cyclopenta[a]naphthalen-2-yl)-amide (Stage 40.1) using synthetic methodology described in the preparation of Example 20.

LCMS: $t_R$=0.29 min, M+H=374.0, M−H=372 (method J).
$^1$H-NMR 1H-NMR (CD$_3$OD, 400 MHz): 7.9 (s, 1H), 7.0 (s, 1H), 5.27 (s, 2H), 4.38 (d, 1H), 3.8 (dd, 1H), 3.5 (m, 1H), 2.5 (m, 1H), 2.4 (s, 1H), 2.08 (m, 1H), 1.95 (m, 1H), 1.12 (d, 3H).

Stage 40.1: Imidazole-1-carboxylic acid (8-methyl-4H-5-oxa-1-thia-3,7-diaza-cyclopenta[a]naphthalen-2-yl)-amide

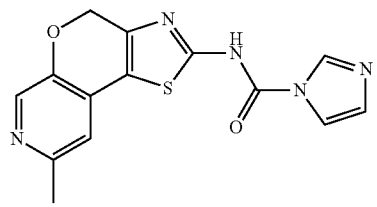 [SMILES: Cc1cc2c(cn1)OCc1nc(NC(=O)n3ccnc3)sc1-2]

Imidazole-1-carboxylic acid (8-methyl-4H-5-oxa-1-thia-3,7-diaza-cyclopenta[a]naphthalen-2-yl)-amide was prepared from N-(8-methyl-4H-5-oxa-1-thia-3,7-diaza-cyclopenta[a]naphthalen-2-yl)-acetamide (Stage 40.2) using synthetic methodology as described for the preparation of intermediate A.

Stage 40.2: N-(8-methyl-4H-5-oxa-1-thia-3,7-diaza-cyclopenta[a]naphthalen-2-yl)-acetamide

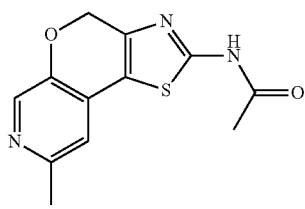 [SMILES: CC(=O)Nc1nc2c(s1)-c1cc(C)ncc1OC2]

A mixture of 463 mg (1.53 mmol) N-[4-(4-bromo-6-methyl-pyridin-3-yloxymethyl)-thiazol-2-yl]-acetamide (Stage 40.3), 900 mg (2.71 mmol) cesium carbonate, 30.4 mg (0.135 mmol) palladium acetate and 81 mg (0.271 mmol) tributylphosphine tetrafluoroborate in 3 mL DMF was stirred at 115° C. for 7 h under argon. Then the reaction mixture was poured onto water, EtOAc was added and, after filtration over a layer of Hyflo Super Gel medium (Fluka 56678), the filtrate was extracted with EtOAc (2×). The combined organic layers were washed with water and brine, dried (MgSO$_4$) and filtered. The filtrate was concentrated in vacuo to leave a residue that was purified on silica gel (=−100% EtOAc in heptane) to afford 93 mg of the title compound as a solid. LCMS: $t_R$=0.27 min, M+H=262, M−H 260 (method J).

Stage 40.3: N-[4-(4-Bromo-6-methyl-pyridin-3-yloxymethyl)-thiazol-2-yl]-acetamide

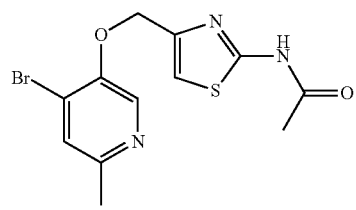 [SMILES: CC(=O)Nc1nc(COc2cnc(C)cc2Br)cs1]

To a solution of 270 mg (1.44 mmol) 4-bromo-6-methyl-pyridin-3-ol (Stage 40.4) in DMF (5 mL), 44.8 mg NaH (1.87 mmol) was added and this mixture was stirred for 1 h at rt. 301 mg (1.58 mmol) 2-acetamido-4-(chloromethyl)-1,3-thiazole (Apollo OR15549) was added and stirring was continued at rt for another 17 h. The reaction mixture was poured on water and extracted with EtOAc (2×). The combined organic layers were washed with water and brine, dried (MgSO$_4$) and filtered. The filtrate was concentrated in vacuo to leave 350 mg of the title compound (white solid) considered sufficiently pure without further purification. LCMS: $t_R$=1.36 min, M+H=342 ($^{79}$Br), 344 ($^{81}$Br) (method J).

Stage 40.4: 4-Bromo-6-methyl-pyridin-3-ol

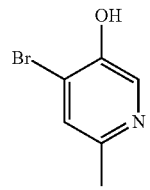

920 mg (3.05 mmol) 4-bromo-5-methoxymethoxy-2-methyl-pyridine (Stage 40.5) were dissolved in 5 mL MeOH, HCl conc. (1 mL, 12 mmol) was added and the reaction mixture was stirred for 2 h at rt. While concentrating the mixture in vacuo, the title compound (as hydrochloride) crystallized. Filtration afforded 570 mg white crystals. $^1$H-NMR (d$_6$-DMSO, 400 MHz): 8.19 (s, 1H), 8.04 (s, 1H), 2.53 (s, 3H).

Stage 40.5:
4-Bromo-5-methoxymethoxy-2-methyl-pyridine

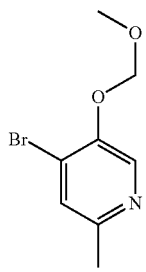

A solution of 1000 mg (6.53 mmol) 5-methoxymethoxy-2-methyl-pyridine (J.-P. Behr et al. Bioorg. Med. Chem. Lett. 2003, 13(10), 1713) in 10 mL THF was cooled to −78° C., where 4.03 mL (6.85 mmol) t-BuLi (1.7M solution in pentane) was added. The resulting mixture was stirred under argon for 1 h, then 2.126 g (6.53 mmol) 1,2-dibromotetrachloroethane (in 5 mL THF) was added. Stirring was continued for 1 h at −78° C. and the reaction mixture was warmed to rt. Saturated NH$_4$Cl solution was added and the aqueous mixture was extracted with EtOAc (2×). The combined organic layers were washed with H$_2$O and brine, dried (MgSO$_4$) and filtered. The filtrate was concentrated in vacuo to leave a residue that was purified on silica gel (EtOAc/hexane=1:1) to afford 920 mg of the title compound as an oil. LCMS: t$_R$=0.29 min, M+H=232 ($^{79}$Br), 234 ($^{81}$Br) (method J).

EXAMPLE 41

(2S,3S)-3-Morpholin-4-ylmethyl-pyrrolidine-1,2-dicarboxylic acid 2-amide 1-[(7-tert-butyl-4,5-dihydro-benzo[1,2-d;3,4-d']bisthiazol-2-yl)-amide]

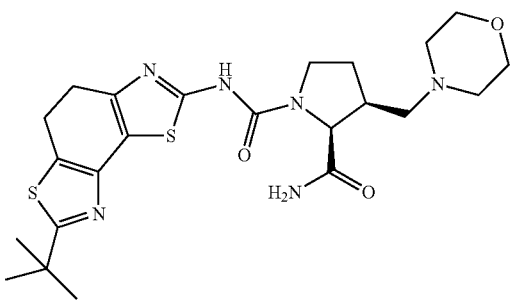 [SMILES: CC(C)(C)c1nc2c(s1)CCc1nc(NC(=O)N3CC[C@@H](CN4CCOCC4)[C@H]3C(N)=O)sc1-2]

The title compound was synthesized using methodology as described for Example 34 using (2S,3S)-3-morpholin-4-ylmethyl-pyrrolidine-2-carboxylic acid amide (Stage 37.1) instead of intermediate D.

LCMS: t$_R$=0.68 min, M+H=505.3.0, M−H=503.2 (method J). $^1$H-NMR (d$_6$-DMSO, 600.13 MHz): 10.65 (s, b, 1H), 7.4 (s, b, 1H), 7.05 (s, b, 1H), 4.3 (s, b, 1H), 3.7 (m, 1H), 3.6 (m, 4H), 3.3 (m, 1H), 3.1 (t, 2H), 2.9 (t, 2H), 2.6 (m, 1H), 2.4 (m, 1H), 2.35 (m, 4H), 2.15 (m, 1H), 2.0 (m, 1H), 1.75 (m, 1H), 1.35 (s, 9H).

EXAMPLE 42

(2S,3R)-3-Methoxymethyl-pyrrolidine-1,2-dicarboxylic acid 2-amide 1-[(8-tert-butyl-4,5-dihydro-thiazolo[4,5-h]quinazolin-2-yl)-amide]

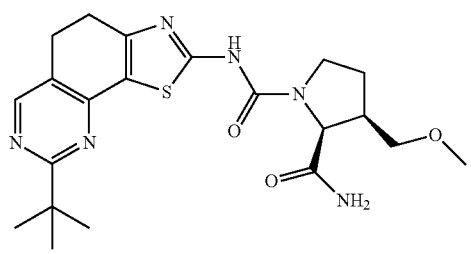 [SMILES: COC[C@@H]1CCN(C(=O)Nc2nc3c(s2)-c2nc(C(C)(C)C)ncc2CC3)[C@@H]1C(N)=O]

Triethylamine (0.525 mmol) was added to a solution of imidazole-1-carboxylic acid (8-tert-butyl-4,5-dihydro-thiazolo[4,5-h]quinazolin-2-yl)-amide (Intermediate A) (0.175 mmol) and (2S,3R)-3-methoxymethyl-pyrrolidine-2-carboxylic acid amide (Stage 42.1) (0.192 mmol) in DMF (0.7 mL) at rt. After stirring for 3 h, the reaction mixture was concentrated. The residue was purified by silica gel column chromatography to afford the title compound as a white solid. HPLC: t$_R$=2.84 min (method G); LCMS: t$_R$=1.71 min, [M+H]$^+$ 445 (method I); TLC: R$_f$=0.41 (19:1 CH$_2$Cl$_2$/MeOH); $^1$H-NMR (d$_6$-DMSO, 600 MHz): 11.15 (br s, 1H), 8.40 (s, 1H), 7.42 (br s, 1H), 7.05 (br s, 1H), 4.27 (m, 1H), 3.74 (m, 1H), 3.46 (m, 1H), 3.42 (m, 1H), 3.24 (s, 3H), 3.16 (m, 1H), 2.98 (m, 2H), 2.91 (m, 2H), 2.54 (m, 1H), 2.03 (m, 1H), 1.77 (m, 1H), 1.32 (s, 9H).

Stage 42.1:
(2S,3R)-3-Methoxymethyl-pyrrolidine-2-carboxylic acid amide

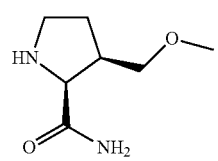

The title compound was prepared in analogy to the procedure described in Stage 37.1 but (2S,3R)-3-methoxymethyl-1-((S)-1-phenyl-ethyl)-pyrrolidine-2-carboxylic acid amide (Stage 42.2) was used instead of (2S,3S)-3-morpholin-4-ylmethyl-1-((S)-1-phenyl-ethyl)-pyrrolidine-2-carboxylic acid amide.

The title compound was obtained as a white solid. ESI-MS: [M+H]+ 159.

Stage 42.2: (2S,3R)-3-Methoxymethyl-1-((S)-1-phenyl-ethyl)-pyrrolidine-2-carboxylic acid amide

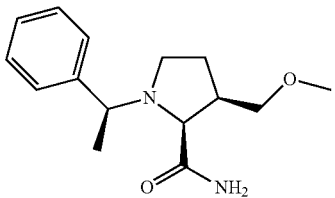 [SMILES: COC[C@@H]1CCN([C@@H](C)c2ccccc2)[C@@H]1C(N)=O]

The title compound was prepared in analogy to the procedure described in Stage 37.2 but (2S,3R)-3-methoxymethyl-1-((S)-1-phenyl-ethyl)-pyrrolidine-2-carboxylic acid methyl ester (Stage 42.3) was used instead of (2S,3S)-3-morpholin-4-ylmethyl-1-((S)-1-phenyl-ethyl)-pyrrolidine-2-carboxylic acid methyl ester.

The title compound was obtained as a yellow oil. HPLC: $t_R$=2.35 min (method G); LC-MS: $t_R$=0.47 min, [M+H]+ 263 (method K); TLC: $R_f$=0.05 (1:1 Heptanes/EtOAc).

Stage 42.3: (2S,3R)-3-Methoxymethyl-1-((S)-1-phenyl-ethyl)-pyrrolidine-2-carboxylic acid methyl ester

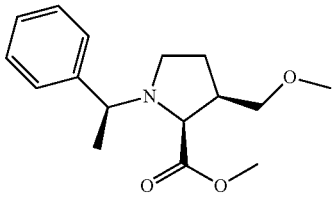 [SMILES: COC[C@@H]1CCN([C@@H](C)c2ccccc2)[C@@H]1C(=O)OC]

A mixture of (3aR,6aS)-1-((S)-1-phenyl-ethyl)-hexahydro-furo[3,4-b]pyrrol-6-one [805246-48-4] (17.05 mmol), KOH (71.60 mmol) and iodomethane (68.20 mmol) in toluene (79 mL) was stirred at 80° C. for 1.5 h. The reaction mixture was cooled to rt and partitioned between water and MTBE. The aqueous layer was extracted with MTBE (3×). The combined organic layers were dried (Na2SO4), filtered and concentrated. The residue was purified by silica gel column chromatography to afford the title compound as a yellow oil. HPLC: $t_R$=2.98 min (method G); LC-MS: $t_R$=0.69 min, [M+H]+ 278 (method K); TLC: $R_f$=0.25 (1:3 Heptanes/EtOAc).

EXAMPLE 43

(2S,3S)-3-Dimethylaminomethyl-pyrrolidine-1,2-dicarboxylic acid 2-amide 1-[(8-tert-butyl-4,5-dihydro-thiazolo[4,5-h]quinazolin-2-yl)-amide]

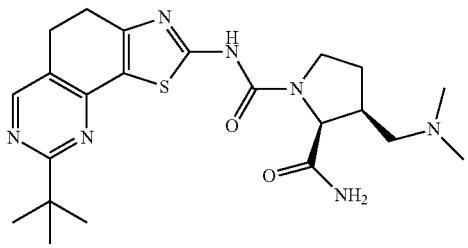 [SMILES: CN(C)C[C@@H]1CCN(C(=O)Nc2nc3c(s2)-c2nc(C(C)(C)C)ncc2CC3)[C@@H]1C(N)=O]

Triethylamine (0.305 mmol) was added to a solution of imidazole-1-carboxylic acid (8-tert-butyl-4,5-dihydro-thiazolo[4,5-h]quinazolin-2-yl)-amide (Intermediate A) (0.102 mmol) and (2S,3S)-3-dimethylaminomethyl-pyrrolidine-2-carboxylic acid amide (Stage 43.1) (0.102 mmol) in DMF (0.3 mL) at rt. After stirring for 0.5 h, the reaction mixture was concentrated and dried overnight under vacuum at 50° C. The residue was suspended in EtOAc (1 mL), filtered and dried under vacuum to afford the title compound as a white solid. HPLC: $t_R$=4.01 min (method H); LCMS: $t_R$=1.33 min, [M+H]+ 458 (method I); TLC: $R_f$=0.08 (4:1 CH2Cl2/MeOH); 1H-NMR (d6-DMSO, 600 MHz): 11.14 (br s, 1H), 8.40 (s, 1H), 7.42 (br s, 1H), 7.06 (br s, 1H), 4.27 (m, 1H), 3.71 (m, 1H), 3.42 (m, 1H), 2.98 (m, 2H), 2.90 (m, 2H), 2.52 (m, 1H), 2.33 (m, 1H), 2.18 (m, 1H), 2.18 (s, 6H), 2.01 (m, 1H), 1.72 (m, 1H), 1.32 (s, 9H).

Stage 43.1: (2S,3S)-3-Dimethylaminomethyl-pyrrolidine-2-carboxylic acid amide

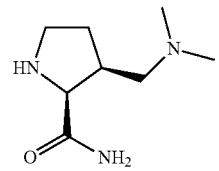

The title compound was prepared in analogy to the procedure described in Stage 37.1 but (2S,3S)-3-dimethylaminomethyl-1-((S)-1-phenyl-ethyl)-pyrrolidine-2-carboxylic acid amide (Stage 43.2) was used instead of (2S,3S)-3-morpholin-4-ylmethyl-1-((S)-1-phenyl-ethyl)-pyrrolidine-2-carboxylic acid amide. Also, the hydrogenation was performed under 4 bar pressure.

The title compound was obtained as a yellow oil. ESI-MS: [M+H]+ 172.

Stage 43.2: (2S,3S)-3-Dimethylaminomethyl-1-((S)-1-phenyl-ethyl)-pyrrolidine-2-carboxylic acid amide

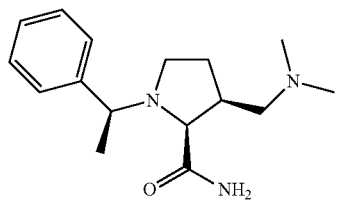 [SMILES: C[C@@H](c1ccccc1)N1CC[C@@H](CN(C)C)[C@H]1C(N)=O]

A mixture of (2S,3S)-3-aminomethyl-1-((S)-1-phenyl-ethyl)-pyrrolidine-2-carboxylic acid amide (Stage 43.3) (0.418 mmol), sodium cyanoborohydride (2.86 mmol) and 37% aqueous formaldehyde (2.14 mmol) in MeOH (3.3 mL) was stirred at 55° C. for 16 h. The reaction mixture was cooled to rt and concentrated. The residue was purified using a RediSep® silica gel column to afford the title compound as a white foam. HPLC: $t_R$ 3.59 min (method H); LC-MS: $t_R$=0.86 min, [M+H]$^+$ 276 (method I); TLC: $R_f$=0.13 (9:1 CH$_2$Cl$_2$/MeOH).

Stage 43.3: (2S,3S)-3-Aminomethyl-1-((S)-1-phenyl-ethyl)-pyrrolidine-2-carboxylic acid amide

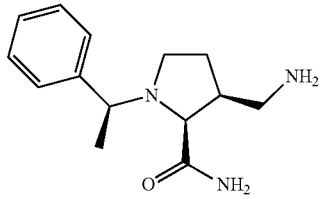 [SMILES: C[C@@H](c1ccccc1)N1CC[C@@H](CN)[C@H]1C(N)=O]

A mixture of (2S,3S)-3-azidomethyl-1-((S)-1-phenyl-ethyl)-pyrrolidine-2-carboxylic acid amide (Stage 36.3) (0.723 mmol) and triphenylphosphine (0.867 mmol) in THF (3 mL) was stirred at rt for 25 h. The reaction mixture was concentrated to afford the crude title compound as a light brown solid. HPLC: $t_R$ 3.53 min (method H); ESI-MS: [M+H]$^+$ 248.

EXAMPLE 44

(2S,3R)-3-Methyl-pyrrolidine-1,2-dicarboxylic acid 2-amide 1-{[8-(2,2,2-trifluoro-1,1-dimethyl-ethyl)-4,5-dihydro-thiazolo[4,5-h]quinazolin-2-yl]-amide}

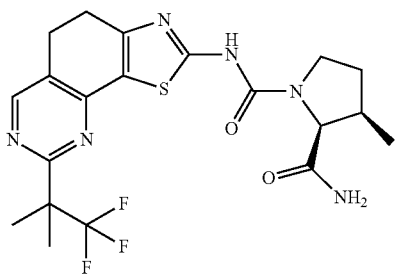 [SMILES: C[C@@H]1CCN(C(=O)Nc2nc3c(s2)-c2nc(C(C)(C)C(F)(F)F)ncc2CC3)[C@@H]1C(N)=O]

Triethylamine (1.714 mmol) was added to a solution of imidazole-1-carboxylic acid [8-(2,2,2-trifluoro-1,1-dimethyl-ethyl)-4,5-dihydro-thiazolo[4,5-h]quinazolin-2-yl]-amide (Stage 44.1) (0.490 mmol) and (2S,3R)-3-methyl-pyrrolidine-2-carboxylic acid amide (intermediate P) (0.979 mmol) in DMF (1.5 mL) at rt. After stirring for 1.5 h, the reaction mixture was concentrated. The residue was diluted with a saturated solution of NaHCO$_3$ and extracted with EtOAc (2×). The combined organic layers were successively washed with water and brine, dried (Na$_2$SO$_4$), filtered and concentrated. The residue was purified using a RediSep® silica gel column to to afford the title compound as a beige solid. HPLC: $t_R$=5.77 min (method H); LCMS: $t_R$=2.18 min, [M+H]$^+$ 469 (method I); TLC: $R_f$=0.16 (19:1 CH$_2$Cl$_2$/MeOH); $^1$H-NMR (d$_6$-DMSO, 600 MHz): 11.19 (br s, 1H), 8.50 (s, 1H), 7.43 (br s, 1H), 7.01 (br s, 1H), 4.18 (m, 1H), 3.72 (m, 1H), 3.40 (m, 1H), 3.03 (m, 2H), 2.94 (m, 2H), 2.38 (m, 1H), 1.97 (m, 1H), 1.70 (m, 1H), 1.58 (s, 6H), 0.99 (d, 3H).

Stage 44.1: Imidazole-1-carboxylic acid [8-(2,2,2-trifluoro-1,1-dimethyl-ethyl)-4,5-dihydro-thiazolo[4,5-h]quinazolin-2-yl]-amide

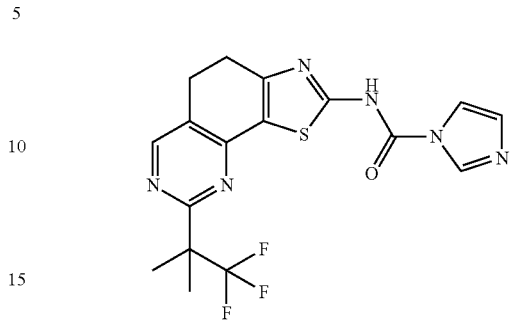

The title compound was prepared in analogy to the procedure described for Intermediate A but in Stage A.3 3,3,3-trifluoro-2,2-dimethyl-propionamidine hydrochloride (Stage 44.2) was used instead of tert-butylamidine hydrochloride.

The title compound was obtained as a beige solid. HPLC: $t_R$=6.73 min (method H); LCMS: $t_R$=1.11 min, [M+H]$^+$ 373 (method J). Note: for characterization purposes, the title compound was dissolved in MeOH→methyl carbamate derivative.

Stage 44.2:
3,3,3-Trifluoro-2,2-dimethyl-propionamidine hydrochloride

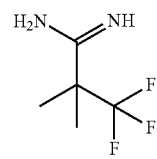

3,3,3-Trifluoro-2,2-dimethyl-propionitrile (Stage 44.3) (12.40 mmol) was added to a solution of sodium methoxide (freshly prepared from 48.40 mmol sodium metal and 102 mL MeOH) at rt. After 4 h, acetic acid (48.40 mmol) and then NH$_4$Cl (14.88 mmol) were slowly added and the reaction mixture was then heated to 70° C. for 40 h. After concentrating (40° C., 100 mbar) the reaction mixture, the residue was suspended in acetone, filtered and dried under vacuum to afford the title compound as a white solid. ESI-MS: [M+H]$^+$ 155.

Stage 44.3:
3,3,3-Trifluoro-2,2-dimethyl-propionitrile

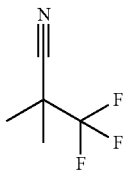

A mixture of 3,3,3-trifluoro-2,2-dimethyl-propionamide (Stage 44.4) (121.2 mmol) and phosphorus pentoxide (121.2 mmol) was slowly heated to 200° C. and the resulting distillate collected. The title compound was obtained as a colorless liquid.

Stage 44.4:
3,3,3-Trifluoro-2,2-dimethyl-propionamide

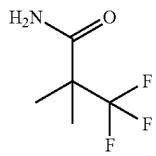

Oxalyl chloride (140.8 mmol) was added dropwise to a solution of 3,3,3-trifluoro-2,2-dimethyl-propionic acid [889940-13-0] (128 mmol) in CH$_2$Cl$_2$ (128 mL) at 0° C. Added a few dr DMF until gas evolution was observed and then continued stirring for 30 min. After warming to rt and stirring overnight, the reaction mixture was concentrated (40° C., 00 mbar). The residue was dissolved in THF (128 mL), cooled to 0° C. and then slowly treated with a solution of concentrated aqueous ammonia (64 mL). After stirring at 0° C. for 30 min and then at rt for 4 h, the reaction mixture was concentrated to half its volume to give a thick white suspension. After filtering and drying, the title compound was obtained as a white solid. ESI-MS: [M+H]$^+$ 156.

EXAMPLE 45

(2S,3R)-3-Methoxymethyl-pyrrolidine-1,2-dicarboxylic acid 2-amide 1-{[8-(2,2,2-trifluoro-1,1-dimethyl-ethyl)-4,5-dihydro-thiazolo[4,5-h]quinazolin-2-yl]-amide}

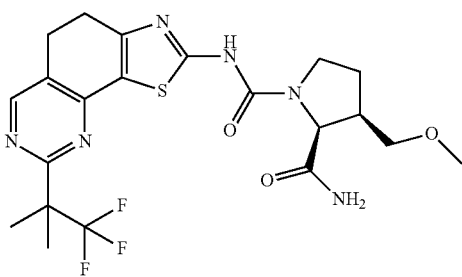 [SMILES: COC[C@@H]1CCN(C(=O)Nc2nc3c(s2)-c2nc(C(C)(C)C(F)(F)F)ncc2CC3)[C@@H]1C(N)=O]

Triethylamine (1.714 mmol) was added to a solution of imidazole-1-carboxylic acid [8-(2,2,2-trifluoro-1,1-dimethyl-ethyl)-4,5-dihydro-thiazolo[4,5-h]quinazolin-2-yl]-amide (Stage 44.1) (0.490 mmol) and (2S,3R)-3-methoxymethyl-pyrrolidine-2-carboxylic acid amide (Stage 42.1) (0.0.979 mmol) in DMF (1.5 mL) at rt. After stirring for 2 h, the reaction mixture was concentrated. The residue was diluted with a saturated solution of NaHCO$_3$ and extracted with EtOAc (2×). The combined organic layers were successively washed with water and brine, dried (Na$_2$SO$_4$), filtered and concentrated. The residue was purified using a RediSep® silica gel column to to afford the title compound as a beige solid. HPLC: t$_R$=5.71 min (method H); LCMS: t$_R$=2.15 min, [M+H]$^+$ 499 (method I); TLC: R$_f$=0.40 (19:1 CH$_2$Cl$_2$/MeOH); $^1$H-NMR (d$_6$-DMSO, 600 MHz): 11.23 (br s, 1H), 8.50 (s, 1H), 7.42 (br s, 1H), 7.06 (br s, 1H), 4.27 (m, 1H), 3.74 (m, 1H), 3.46 (m, 1H), 3.42 (m, 1H), 3.24 (s, 3H), 3.16 (m, 1H), 3.03 (m, 2H), 2.94 (m, 2H), 2.55 (m, 1H), 2.03 (m, 1H), 1.77 (m, 1H), 1.58 (s, 6H).

EXAMPLE 46

(2S,3R)-3-Methyl-pyrrolidine-1,2-dicarboxylic acid 2-amide 1-[(8-tert-butyl-4H-5-oxa-1-thia-3,7-diaza-cyclopenta[a]naphthalen-2-yl)-amide]

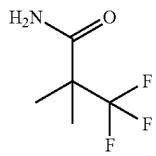

LCMS: t$_R$=0.50 min, M+H=416, M−H=414 (method L). $^1$H-NMR (d$_6$-DMSO, 400 MHz): 8.05 (s, 1H), 7.37 (bs, 1H), 7.09 (s, 1H), 6.97 (bs, 1H), 5.31 (s, 2H), 4.18 (m, 1H), 3.69 (dd, 1H), 3.39 (m, 1H), 2.35 (m, 1H), 1.95 (m, 1H), 1.71 (m, 1H), 1.27 (s, 9H), 0.975 (d, 3H).

The title compound was prepared from 2-tert-butyl-5-methoxymethoxy-pyridine using synthetic methodology as described for the preparation of Example 40. The starting material, 2-tert-butyl-5-methoxymethoxy-pyridine was prepared from 2-bromo-5-methoxymethoxy-pyridine as described below:

2-tert-Butyl-5-methoxymethoxy-pyridine

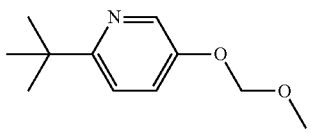

6.69 g (74.7 mmol) copper(I)cyanide in 15 ml dry THF was cooled to −75° C., where 149 ml (149 mmol) of a 1M tert-butylmagnesium chloride solution was added drop-wise. Stirring was continued for 40 min. After that, 4.07 g (18.67 mmol) 2-bromo-5-methoxymethoxy-pyridine (Zhong, W. et al. WO2008147547) dissolved in 30 ml dry THF were added drop-wise. The reaction mixture was stirred at −75° C. for 1 h and then allowed to reach room temperature, where stirring was continued for another 6 h. Then 30 ml of 25% aqueous ammonia was added to the reaction mixture. The mixture was filtered and extracted twice with CH$_2$Cl$_2$. The combined organic layers were washed with water, dried (MgSO$_4$), filtered and concentrated in vacuo. The residue was purified by chromatography on silicagel (EtOAc, heptane) to yield 2.64 g of the pure title compound as an oil. LCMS: $t_R$=0.55 min, M+H=196 (method K).

EXAMPLE 47

(2S,3S)-3-Dimethylaminomethyl-pyrrolidine-1,2-dicarboxylic acid 2-amide 1-[(8-tert-butyl-4H-5-oxa-1-thia-3,7-diaza-cyclopenta[a]naphthalen-2-yl)-amide]

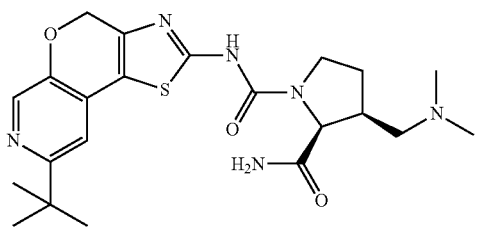 [SMILES: CN(C)C[C@@H]1CCN(C(=O)Nc2nc3c(s2)-c2cc(C(C)(C)C)ncc2OC3)[C@@H]1C(N)=O]

The title compound was prepared using synthetic methodology described for the preparation of Example 46 and using (2S,3S)-3-dimethylaminomethyl-pyrrolidine-2-carboxylic acid amide (Stage 43.1) instead of (2S,3R)-3-methyl-pyrrolidine-2-carboxylic acid amide in the last step of the synthesis.

LC-MS: $t_R$=0.24 min, M−H=457 (method L). $^1$H-NMR ($d_6$-DMSO, 400 MHz): 11.15 (bs, 1H), 8.03 (s, 1H), 7.35 (s, 1H), 7.07 (s, 1H), 7.0 (s, 1H), 5.28 (s, 2H), 4.23 (m, 1H), 3.65 (m, 1H), 3.40 (m, 1H), 2.6-2.45 (m, 2H), 2.30 (m, 1H), 2.17 (s, 6H), 2.15 (m, 1H), 1.70 (m, 1H), 1.27 (s, 9H).

EXAMPLE 48

(2S,3R)-3-Methyl-pyrrolidine-1,2-dicarboxylic acid 2-amide 1-{[8-(2,2,2-trifluoro-1,1-dimethyl-ethyl)-4H-5-oxa-1-thia-3,7-diaza-cyclopenta[a]naphthalen-2-yl]-amide}

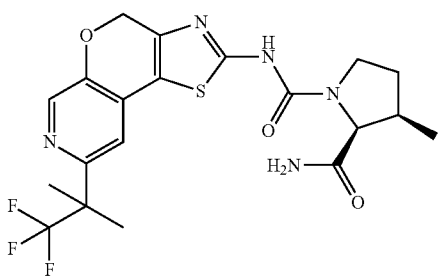 [SMILES: C[C@@H]1CCN(C(=O)Nc2nc3c(s2)-c2cc(C(C)(C)C(F)(F)F)ncc2OC3)[C@@H]1C(N)=O]

LC-MS: $t_R$=1.59 min, M+H=470 (method F). $^1$H-NMR ($d_6$-DMSO, 400 MHz): 11.25 (bs, 1H), 8.15 (s, 1H), 7.42 (s, 1H), 7.34 (s, 1H), 7.00 (s, 1H), 5.40 (s, 2H), 4.19 (s, 1H), 3.71 (m, 1H), ca. 3.4 (m, 1H), 2.5-2.35 (m, 1H), 1.99 (m, 1H), 1.68 (m, 1H), 1.56 (s, 6H), 0.99 (d, 3H).

The title compound was prepared starting from 4-bromo-5-methoxymethoxy-2-(2,2,2-trifluoro-1,1-dimethyl-ethyl)-pyridine using synthetic methodology as described for the preparation of Examples 40 and 42.

4-Bromo-5-methoxymethoxy-2-(2,2,2-trifluoro-1,1-dimethyl-ethyl)-pyridine was prepared as follows

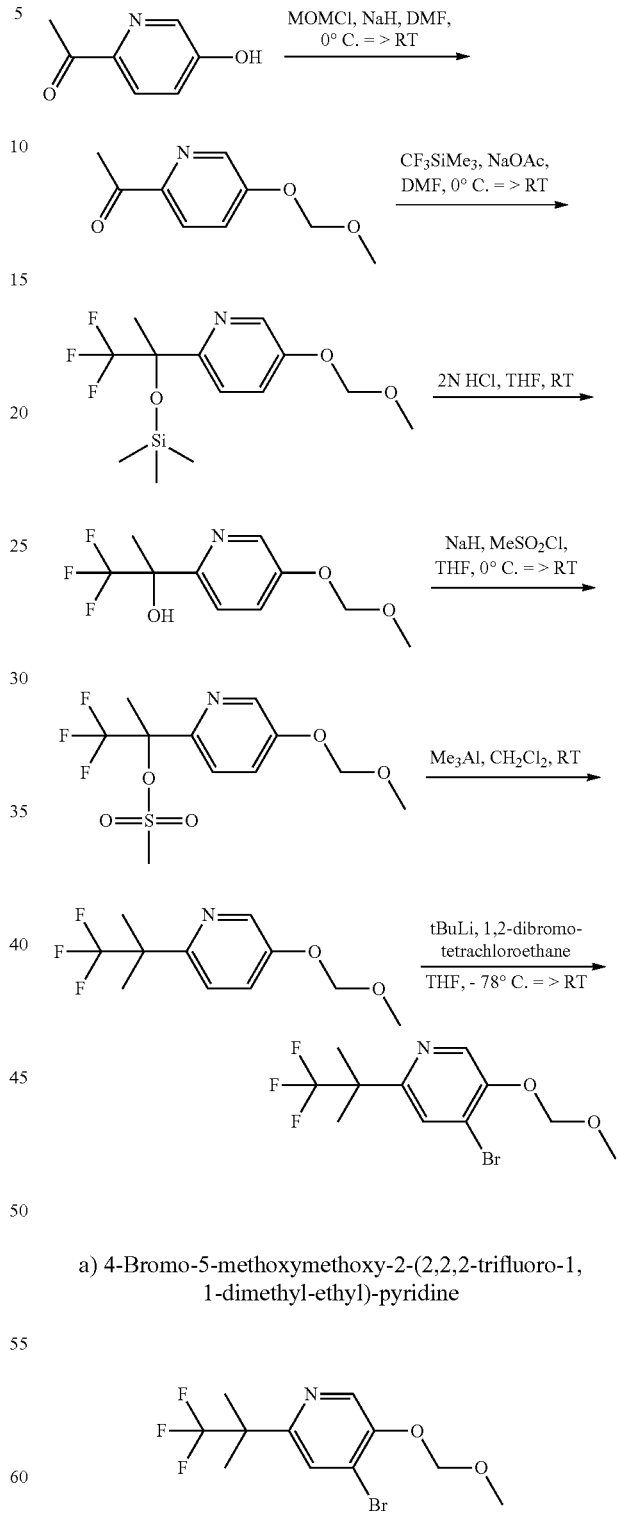

a) 4-Bromo-5-methoxymethoxy-2-(2,2,2-trifluoro-1, 1-dimethyl-ethyl)-pyridine

The title compound was prepared using synthetic methodology as described for the preparation of Example 40, stage 40.5. as an oil. LCMS (method L): $t_R$=1.26 min, M+H=328 ($^{79}$Br), 330 ($^{81}$Br).

b) 5-Methoxymethoxy-2-(2,2,2-trifluoro-1,1-dimethyl-ethyl)-pyridine

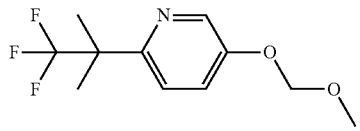

1.7 g (4.13 mmol) methanesulfonic acid 2,2,2-trifluoro-1-(5-methoxymethoxy-pyridin-2-yl)-1-methyl-ethyl ester was dissolved in 20 ml dichloromethane. The reaction mixture was cooled to 0° C. where 2.065 ml (4.13 mmol) trimethylaluminum was added slowly. The reaction mixture was stirred at room temperature for 20 h. After that water was added slowly and the mixture was extracted 2 times with EtOAc. The combined organic layers were washed with water and brine, dried ($MgSO_4$), filtered and concentrated in vacuo. The residue was purified by chromatography on silicagel (EtOAc, heptane) to yield to afford 0.55 g of the pure title compound. LCMS (method L): $t_R$=1.09 min, M+H=250.

c) Methanesulfonic acid 2,2,2-trifluoro-1-(5-methoxymethoxy-pyridin-2-yl)-1-methyl-ethyl ester

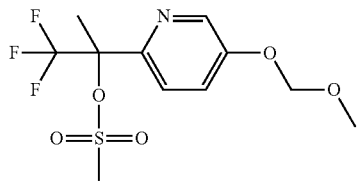 [SMILES: COCOc1ccc(C(C)(OS(C)(=O)=O)C(F)(F)F)nc1]

To a stirred mixture of 0.213 g (8.44 mmol) sodium hydride in 6 ml dry THF, 1.06 g (4.22 mmol) 1,1,1-trifluoro-2-(5-methoxymethoxy-pyridin-2-yl)-propan-2-ol (dissolved in 4.9 ml dry THF) was added dropwise at 0° C. After completion of the addition, stirring was continued for 3 h at room temperature. Then methanesulfonyl chloride (dissolved in 7.3 ml dry THF) was added at room temperature and stirring was continued for another 2 h. Then water and sat. $NaHCO_3$ soln. were added. This mixture was extracted 2 times with EtOAc. The combined organic layers were washed with water and brine, dried ($MgSO_4$), filtered and concentrated in vacuo to afford 1.7 g of the title compound, which was used directly in the next step. LCMS (method L): $t_R$=0.96 min, M+H=330.

d) 1,1,1-Trifluoro-2-(5-methoxymethoxy-pyridin-2-yl)-propan-2-ol

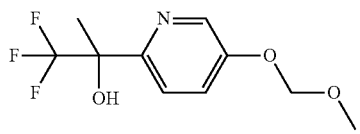

A mixture of 1.48 g (4.58 mmol) 5-methoxymethoxy-2-(2,2,2-trifluoro-1-methyl-1-trimethylsilanyloxy-ethyl)-pyridine and 5 ml (10 mmol) 2N HCl in 15 ml THF was stirred at room temperature for 2 h. After that the reaction mixture was poured on water and a pH of 1-2 was adjusted by the addition of 2N HCl. The reaction mixture was extracted 2 times with EtOAc. The combined organic layers were washed with water and brine, dried ($MgSO_4$), filtered and concentrated in vacuo to afford 1.06 g of the title compound as an oil (88% pure), which was used in the next step without purification. LCMS (method L): $t_R$=0.88 min, M+H=252.

e) 5-Methoxymethoxy-2-(2,2,2-trifluoro-1-methyl-1-trimethylsilanyloxy-ethyl)-pyridine

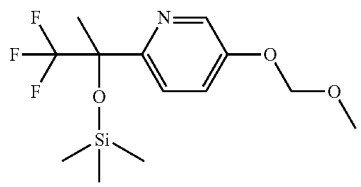 [SMILES: COCOc1ccc(C(C)(O[Si](C)(C)C)C(F)(F)F)nc1]

A mixture of 1.12 g (6.18 mmol) 1-(5-methoxymethoxy-pyridin-2-yl)-ethanone, 1.055 g (7.42 mmol) trimethyl(trifluormethyl)silane and 0.025 g (0.309 mmol) sodium acetate in 9 ml DMF was stirred for 1 h at 0° C. and 1 h at room temperature. After that the reaction mixture was poured on water and a pH of 1-2 was adjusted by the addition of 2N HCl. The reaction mixture was extracted 2 times with EtOAc. The combined organic layers were washed with water and brine, dried ($MgSO_4$), filtered and concentrated in vacuo. The residue was purified by chromatography on silicagel (EtOAc, heptane) to yield 1.87 g of the pure title compound as an oil. LCMS (method L): $t_R$=1.38 min, M+H=324.

f) 1-(5-Methoxymethoxy-pyridin-2-yl)-ethanone

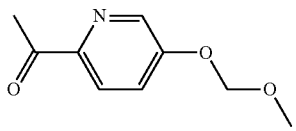

NaH was added to a solution of 1 g (7.29 mmol) 1-(5-hydroxy-pyridin-2-yl)-ethanone (Anichem) in 15 ml DMF at 0° C. After stirring this mixture for 1 h, 0.78 ml (8.75 mmol) MOMCl was added at 0° C. Then the reaction mixture was stirred at room temperature for 2 h. The reaction mixture was poured on water and extracted 2 times with EtOAc. The combined organic layers were washed with water and brine, dried ($MgSO_4$), filtered and concentrated in vacuo. The residue was purified by chromatography on silicagel (EtOAc, heptane) to yield 1.12 g of the pure title compound as an oil. LCMS (method L): $t_R$=0.66 min, M+H=182.

EXAMPLE 49

(2S,3R)-3-Methyl-pyrrolidine-1,2-dicarboxylic acid 2-amide 1-{[7-(2,2,2-trifluoro-1,1-dimethyl-ethyl)-4,5-dihydro-benzo[1,2-d ;3,4-d']bisthiazol-2-yl]-amide}

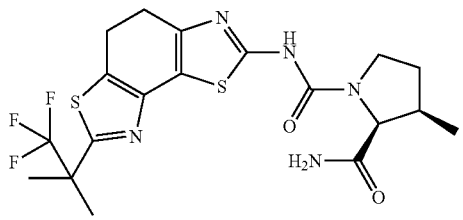 [SMILES: C[C@@H]1CCN(C(=O)Nc2nc3c(s2)-c2nc(C(C)(C)C(F)(F)F)sc2CC3)[C@@H]1C(N)=O]

LCMS: $t_R$=0.97 min, M+H=474, M−H=414 (method L). $^1$H-NMR (d$_6$-DMSO, 400 MHz): 10.7 (bs, 1H), 7.37 (s, 1H), 6.97 (s, 1H), 4.18 (m, 1H), 3.69 (dd, 1H), 3.39 (m, 1H), 3.14 (t, 2H), 2.95 (t, 2H), 2.34 (m, 1H), 1.94 (m, 1H), 1.68 (m, 1H), 1.62 (s, 6H), 0.965 (s, 3H). The title compound was prepared from 2,2-dimethyl-thiopropionamide using synthetic methodology as described for the preparation of Example 39. The starting material, 3,3,3-trifluoro-2,2-dimethyl-thiopropionamide was prepared as described below:

Preparation of 3,3,3-trifluoro-2,2-dimethyl-thiopropionamide a) 3,3,3-Trifluoro-2,2-dimethyl-propionamide

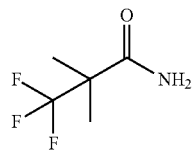

A mixture of 2 g (12.81 mmol) 3,3,3-trifluoro-2,2-dimethylpropionic acid (Aldrich), 2.077 g (12.81 mmol) carbonyldiimidazole and 5.55 ml (64.1 mmol) aqueous ammonia in 50 ml CH$_2$Cl$_2$ was stirred at room temperature for 20 h. After that, diethyl ether was added and the resulting mixture was washed with 0.1 N HCL, 0.1 N NaOH, water and brine. The organic layer was dried (MgSO$_4$), filtered and concentrated in vacuo to afford 1.15 g of the title compound as white crystals, that were used in the next step without further purification. MS: M+H=156.

b) 3,3,3-Trifluoro-2,2-dimethyl-thiopropionamide

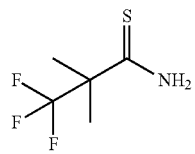

A mixture of 1.05 g (6.77 mmol) 3,3,3-trifluoro-2,2-dimethyl-propionamide and 1.48 g (3.66 mmol) Lawesson's reagent in 32 ml dry THF was stirred at reflux temperature for 20 h. After that the reaction mixture was cooled to room temperature and concentrated in vacuo. The residue was purified by chromatography on silicagel (heptane, EtOAc) to afford 0.81 g of the title compound as pure white crystals. MS: M+H=172.

Using (2S,3R)-3-methoxymethyl-pyrrolidine-2-carboxylic acid amide (Stage 42.1) in the last step of the synthesis the following example was prepared in the same way:

EXAMPLE 50

(2S,3R)-3-Methoxymethyl-pyrrolidine-1,2-dicarboxylic acid 2-amide 1-{[7-(2,2,2-trifluoro-1,1-dimethyl-ethyl)-4,5-dihydro-benzo[1,2-d;3,4-d']bisthiazol-2-yl]-amide}

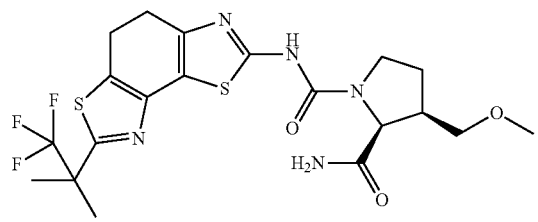 [SMILES: COC[C@@H]1CCN(C(=O)Nc2nc3c(s2)-c2nc(C(C)(C)C(F)(F)F)sc2CC3)[C@@H]1C(N)=O]

LC-MS: $t_R$=0.96 min, M+H=504, M−H=502 (method L). $^1$H-NMR (d$_6$-DMSO, 400 MHz): 10.76 (bs, 1H), 7.34 (bs, 1H), 7.02 (bs, 1H), 4.29 (m, 1H), 3.45 (m, 1H), 3.42 (m, 2H), 3.22 (s, 3H), 3.14 (m, 3H), 2.97 (m, 2H), 2.48 (m, 1H), 1.97 (m, 1H), 1.75 (m, 1H), 1.62 (s, 6H).

EXAMPLE 51

(2S,3S)-3-Dimethylaminomethyl-pyrrolidine-1,2-dicarboxylic acid 2-amide 1-[(7-tert-butyl-4,5-dihydro-benzo[1,2-d;3,4-d']bisthiazol-2-yl)-amide]

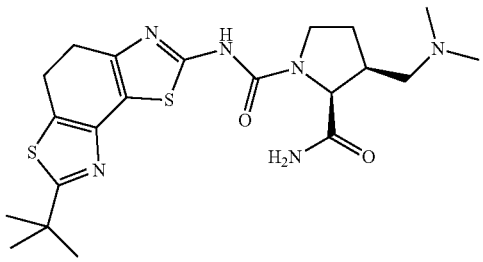 [SMILES: CN(C)C[C@@H]1CCN(C(=O)Nc2nc3c(s2)-c2nc(C(C)(C)C)sc2CC3)[C@@H]1C(N)=O]

The title compound was prepared using synthetic methodology described for the preparation of Example 39 and using (2S,3S)-3-dimethylaminomethyl-pyrrolidine-2-carboxylic acid amide (Stage 43.1) instead of (2S,3R)-3-methyl-pyrrolidine-2-carboxylic acid amide in the last step of the synthesis.

LC-MS: $t_R$=0.91 min, M+H=463, M−H=461 (method L). $^1$H-NMR (d$_6$-DMSO, 400 MHz): 10.7 (bs, 1H), 7.36 (s, 1H), 7.01 (bs, 1H), 4.28 (m, 1H), 3.67 (dd, 1H), 3.39 (m, 1H), 3.07 (m, 2H), 2.92 (m, 2H), 2.5-2.44 (m, 2H), 2.30 (m, 1H), 2.14 (s, 6H), 1.95 (m, 1H), 1.40 (m, 1H), 1.36 (s, 9H).

Efficiency as PI3 Kinase Inhibitors

PI3K KinaseGlo assay: 50 nL of compound dilutions were dispensed onto black 384-well low volume Non Binding Styrene (NBS) plates (Costar Cat. No. NBS #3676). L-a-phosphatidylinositol (PI), provided as 10 mg/ml solution in methanol, was transferred into a glass tube and dried under nitrogen beam. It was then resuspended in 3% OctylGlucoside (OG) by vortexing and stored at 4° C. The KinaseGlo Luminescent Kinase Assay (Promega, Madison, Wis. USA) is a homogeneous HTS method of measuring kinase activity by quantifying the amount of ATP remaining in solution following a kinase reaction.

5 μL of a mix of PI/OG with the PI3K subtype were added (Table 1). Kinase reactions were started by addition of 5 μl of ATP-mix containing in a final volume 10 μL 10 mM TRIS-HCl pH 7.5, 3 mM $MgCl_2$, 50 mM NaCl, 0.05% CHAPS, 1 mM DTT and 1 μM ATP, and occurred at room temperature. Reactions were stopped with 10 μl of KinaseGlo and plates were read 10 mins later in a Synergy2 reader using an integration time of 0.1 seconds per well. 2.5 μM of a pan-class 1 PI3 kinase inhibitor (standard) was added to the assay plates to generate the 100% inhibition of the kinase reaction, and the 0% inhibition was given by the solvent vehicle (90% DMSO in water). The standard was used as a reference compound and included in all assay plates in the form of 16 dilution points in duplicate.

TABLE 1

PI3Ks by KinaseGlo: assay conditions and reagent protocol

| Vol (10 μL) | Enzyme (nM) | ATP (μM) | PI/OG (μM/μg/ml) | NaCl (mM) | $Mg^{2+}$ (mM) | CHAPS (%) | DTT (mM) | time (mins) |
|---|---|---|---|---|---|---|---|---|
| PI3Kα | 10 | 1 | 11/10 | 50 | 3 | 0.05 | 1 | 30 |
| PI3Kβ | 25 | 1 | 11/10 | 50 | 3 | 0.05 | 1 | 30 |
| PI3Kγ | 150 | 1 | 22/20 | 50 | 3 | 0.05 | 1 | 90 |
| PI3Kd | 10 | 1 | 11/10 | 50 | 3 | 0.05 | 1 | 30 |

Cloning of PI3Ks

The PI3Kα, PI3Kβ and PI3Kδ constructs are fusion of p85α iSH2 domain and the respective p110 isoforms. The p85α fragment and p110 isoform genes were generated by PCR from first strand cDNA generated by RT-PCR from commercial RNA from placenta, testis and brain as described below. The PI3Kγ construct was obtained from Roger Williams lab, MRC Laboratory of Molecular Biology, Cambridge, UK (November, 2003) and is described (Pacold, Michael E.; Suire, Sabine; Perisic, Olga; Lara-Gonzalez, Samuel; Davis, Colin T.; Walker, Edward H.; Hawkins, Phillip T.; Stephens, Len; Eccleston, John F.; Williams, Roger L. Crystal structure and functional analysis of Ras binding to its effector phosphoinositide 3-kinase gamma. Cell (2000), 103 (6), 931-943).

PI3Kα Constructs and Proteins

```
PI3Kα wt  BV1075  p85iSH2(461-568)-GGGGGGGGGGGG-
                  p110α(21-1068)-His
```

BV1075: The construct for Baculovirus BV-1075 was generated by a three-part ligation comprised of a p85 fragment and a p110α fragment cloned into vector pBlueBac4.5. The p85 fragment was derived from plasmid p1661-2 digested with Nhe/Spe. The p110α fragment derived from is clone was verified by sequencing and used in a LR410 as a SpeI/HindIII fragment. For the generation of the baculovirus expression vector LR410 the gateway LR reaction to transfer the insert into the Gateway adapted pBlueBac4.5 (Invitrogen) vector was used. The cloning vector pBlueBac4.5 (Invitrogen) was digested with Nhe/HindIII. This resulted in the construct PED 153.8. The p85 component (iSH2) was generated by PCR using ORF 318 (described above) as a template and one forward primer KAC1028 (5'-GCTAGCATGCGAGAATAT-GATAGAT-TATATGAAG-AATATACC) (SEQ ID No. 1) and two reverse primers, KAC1029 (5'-GCCTCCACCAC-CTC-CGCCTG-GTTTAATGCTGTTCATACGTTTGTC) (SEQ ID No. 2) and KAC1039 (5'-TACTAGTC-CGCCTCCAC-CACCTCCGCCTCCACCACCTCCGCC) (SEQ ID No. 3). The two reverse primers overlap and incorporate the 12× Gly linker and the N-terminal sequence of the p110α gene to the SpeI site. The 12× Gly linker replaces the single Gly linker in the BV1052 construct. The PCR fragment was cloned into pCR2.1 TOPO (Invitrogen). Of the resulting clones, p1661-2 was determined to be correct by sequencing. This plasmid was digested with Nhe and SpeI and the resulting fragment was gel-isolated and purified for sub-cloning.

The p110α cloning fragment was generated by enzymatic digest of clone LR410 (see above) with Spe I and HindIII. The SpeI site is in the coding region of the p110 α gene. The resulting fragment was gel-isolated and purified for sub-cloning. The cloning vector, pBlueBac4.5 (Invitrogen) was prepared by enzymatic digestion with Nhe and HindIII. The cut vector was purified with Qiagen column and then dephosphorylated with Calf Intestine alkaline phosphatase (CIP) (BioLabs). After completion of the CIP reaction the cut vector was again column purified to generate the final vector. A three-part ligation was performed using Roche Rapid ligase and the vendor specifications. The final plasmid was verified by sequencing.

Kinase domain.
Protein Sequence of BV 1075:

(SEQ ID No. 4)

```
  1  MREYDRLYEE YTRTSQEIQM KRTAIEAFNE TIKIFEEQCQ TQERYSKEYI EKFKREGNEK

61  EIQRIMHNYD KLKSRISEII DSRRRLEEDL KKQAAEYREI DKRMNSIKPG GGGGGGGGGG

121  GLVECLLPNG MIVTLECLRE ATLITIKHEL FKEARKYPLH QLLQDESSYI FVSVTQEAER
```

-continued

```
 181 EEFFDETRRL CDLRLFQPFL KVIEPVGNRE EKILNREIGF AIGMPVCEFD MVKDPEVQDF

241 RRNILNVCKE AVDLRDLNSP HSRAMYVYPP NVESSPELPK HIYNKLDKGQ IIVVIWVIVS

301 PNNDKQKYTL KINHDCVPEQ VIAEAIRKKT RSMLLSSEQL KLCVLEYQGK YILKVCGCDE

361 YFLEKYPLSQ YKYIRSCIML GRMPNLMLMA KESLYSQLPM DCFTMPSYSR RISTATPYMN

421 GETSTKSLWV INSALRIKIL CATYVNVNIR DIDKIYVRTG IYHGGEPLCD NVNTQRVPCS

481 NPRWNEWLNY DIYIPDLPRA ARLCLSICSV KGRKGAKEEH CPLAWGNINL FDYTDTLVSG

541 KMALNLWPVP HGLEDLLNPI GVTGSNPNKE TPCLELEFDW FSSVVKFPDM SVIEEHANWS

601 VSREAGFSYS HAGLSNRLAR DNELRENDKE QLKAISTRDP LSEITEQEKD FLWSHRHYCV

661 TIPEILPKLL LSVKWNSRDE VAQMYCLVKD WPPIKPEQAM ELLDCNYPDP MVRGFAVRCL

721 EKYLTDDKLS QYLIQLVQVL KYEQYLDNLL VRFLLKKALT NQRIGHFFFW HLKSEMHNKT

781 VSQRFGLLLE SYCRACGMYL KHLNRQVEAM EKLINLTDIL KQEKKDETQK VQMKFLVEQM

841 RRPDFMDALQ GFLSPLNPAH QLGNLRLEEC RIMSSAKRPL WLNWENPDIM SELLFQNNEI

901 IFKNGDDLRQ DMLTLQIIRI MENIWQNQGL DLRMLPYGCL SIGDCVGLIE VVRNSHTIMQ

961 IQCKGGLKGA LQFNSHTLHQ WLKDKNKGEI YDAAIDLFTR SCAGYCVATF ILGIGDRHNS

1021 NIMVKDDGQL FHIDFGHFLD HKKKKFGYKR ERVPFVLTQD FLIVISKGAQ ECTKTREFER

1081 FQEMCYKAYL AIRQHANLFI NLFSMMLGSG MPELQSFDDI AYIRKTLALD KTEQEALEYF

1141 MKQMNDAHHG GWTTKMDWIF HTIKQHALNE LGGAHHHHHH
```

PI3Kβ Constructs and Proteins

```
PI3Kβ    BV949    p85iSH2(461-N58K-568)-GGGGGG-
                  p110β(2-1070)-His
```

BV949: PCR products for the inter SH2 domain (iSH2) of the p85 PI3Kα, PI3Kβ and PI3Kδ subunit and for the full-length p110β subunit were generated and fused by overlapping PCR. The iSH2 PCR product was obtained from first strand cDNA generated by RT-PCR from commercial human RNA from placenta, testis and brain (Clontech), initially using primers gwG130-p01 (5'-CGAGAATATGATAGAT-TATATGAAGAAT-3') (SEQ ID No. 5) and gwG130-p02 (5'-TGGTTT-AATGCTGTTCATACGTTTGTCAAT-3') (SEQ ID No. 6). Subsequently, in a secondary PCR reaction Gateway recombination AttB1 sites and linker sequences were added at the 5'end and 3'end of the p85 iSH2 fragment respectively, using primers gwG130-p03 (5'-GGGACAAGTT-TG-TACAAAAAAGCAGGCTACGAAG-GAGATATACATATGCGAGAATATGATAGAT TATATGAAGAAT-3') (SEQ ID No. 7) and gwG130-p05 (5'-ACTGAAGCATCCTCCTC-CTCCTCCT-CCTGGTT-TAATGCTGTTCATACGTTTGTC-3') (SEQ ID No. 8). The p110β fragment was obtained by PCR using as template a p110β clone (from unknown source that was sequence verified) using primers gwG130-p04 (5'-ATTAAACCAGGAG-GAGGAGGAGGAGGATGCTT-CAGTTTCATAATGC-CTCCTGCT-3') (SEQ ID No. 9) which contains linker sequences and the 5'end of p110β and gwG130-p06 (5'-AGCTCCGTGATGGTGATGGTGATGTGCTCCAGATC-TGTAGTCTTTCCGAA-CTGTGTG-3) (SEQ ID No. 10) which contains sequences of the 3'end of p110-β fused to a Histidine tag. The p85-iSH2/p110β fusion protein was assembled by an overlapping PCR a reaction of the linkers at the 3'end of the iSH2 fragment and the 5'end of the p110β fragment, using the above mentioned gwG130-p03 primer and a primer containing an overlapping Histidine tag and the AttB2 recombination sequences (5'-GGGACCACTTTGTA-CAAGAAAGCTGGGTTTAAGCTCCGT-GATGGTGATGGTGA TGTGCTCC-3') (SEQ ID No. 11). This final product was recombined in a Gateway (Invitrogen) OR reaction into the donor vector pDON R201 (Invitrogen) to generate the ORF253 entry clone. This clone was verified by sequencing and used in a Gateway LR reaction (Invitrogen) to transfer the insert into the Gateway adapted pBlueBac4.5 (Invitrogen) vector for generation of the baculovirus expression vector LR280. This LR280 has an amino acid mutation in the p85 sequence.

Kinase domain.

Protein Sequence of BV949:

```
                                                         (SEQ ID No. 12)
  1 MREYDRLYEE YTRTSQEIQM KRTAIEAFNE TIKIFEEQCQ TQERYSKEYI EKFKREGKEK

61 EIQRIMHNYD KLKSRISEII DSRRRLEEDL KKQAAEYREI DKRMNSIKPG GGGGGCFSFI

121 MPPAMADILD IWAVDSQIAS DGSIPVDFLL PTGIYIQLEV PREATISYIK QMLWKQVHNY

181 PMFNLLMDID SYMFACVNQT AVYEELEDET RRLCDVRPFL PVLKLVTRSC DPGEKLDSKI

241 GVLIGKGLHE FDSLKDPEVN EFRRKMRKFS EEKILSLVGL SWMDWLKQTY PPEHEPSIPE
```

```
 301 NLEDKLYGGK LIVAVHFENC QDVFSFQVSP NMNPIKVNEL AIQKRLTIHG KEDEVSPYDY

361 VLQVSGRVEY VFGDHPLIQF QYIRNCVMNR ALPHFILVEC CKIKKMYEQE MIAIEAAINR

421 NSSNLPLPLP PKKTRIISHV WENNNPFQIV LVKGNKLNTE ETVKVHVRAG LFHGTELLCK

481 TIVSSEVSGK NDHIWNEPLE FDINICDLPR MARLCFAVYA VLDKVKTKKS TKTINPSKYQ

541 TIRKAGKVHY PVAWVNTMVF DFKGQLRTGD IILHSWSSFP DELEEMLNPM GTVQTNPYTE

601 NATALHVKFP ENKKQPYYYP PFDKIIEKAA EIASSDSANV SSRGGKKFLP VLKEILDRDP

661 LSQLCENEMD LIWTLRQDCR EIFPQSLPKL LLSIKWNKLE DVAQLQALLQ IWPKLPPREA

721 LELLDFNYPD QYVREYAVGC LRQMSDEELS QYLLQLVQVL KYEPFLDCAL SRFLLERALG

781 NRRIGQFLFW HLRSEVHIPA VSVQFGVILE AYCRGSVGHM KVLSKQVEAL NKLKTLNSLI

841 KLNAVKLNRA KGKEAMHTCL KQSAYREALS DLQSPLNPCV ILSELYVEKC KYMDSKMKPL

901 WLVYNNKVFG EDSVGVIFKN GDDLRQDMLT LQMLRLMDLL WKEAGLDLRM LPYGCLATGD

961 RSGLIEVVST SETIADIQLN SSNVAAAAAF NKDALLNWLK EYNSGDDLDR AIEEFTLSCA

1021 GYCVASYVLG IGDRHSDNIM VKKTGQLFHI DFGHILGNFK SKFGIKRERV PFILTYDFIH

1081 VIQQGKTGNT EKFGRFRQCC EDAYLILRRH GNLFITLFAL MLTAGLPELT SVKDIQYLKD

1141 SLALGKSEEE ALKQFKQKFD EALRESWTTK VNWMAHTVRK DYRSGAHHHH HHGA
```

Kinase domain.
PI3Kγ Construct and Protein

PI3Kγ   BV950   p110γ(Δ143-[Met144-1102])-His

Construct obtained from Roger Williams lab, MRC Laboratory of Molecular Biology, Cambridge, UK (November, 2003). Description of the construct in (Pacold, Michael E.; Suire, Sabine; Perisic, Olga; Lara-Gonzalez, Samuel; Davis, Colin T.; Walker, Edward H.; Hawkins, Phillip T.; Stephens, Len; Eccleston, John F.; Williams, Roger L. Crystal structure and functional analysis of Ras binding to its effector phosphoinositide 3-kinase gamma. Cell (2000), 103(6), 931-943). Constructs lacking the N-terminal 144 aa. Protein sequence of BV950:

```
                                                        (SEQ ID No. 13)
  1 MSEESQAFQR QLTALIGYDV TDVSNVHDDE LEFTRRGLVT PRMAEVASRD PKLYAMHPWV

61 TSKPLPEYLW KKIANNCIFI VIHRSTTSQT IKVSPDDTPG AILQSFFTKM AKKKSLMDIP

121 ESQSEQDFVL RVCGRDEYLV GETPIKNFQW VRHCLKNGEE IHVVLDTPPD PALDEVRKEE

181 WPLVDDCTGV TGYHEQLTIH GKDHESVFTV SLWDCDRKFR VKIRGIDIPV LPRNTDLTVF

241 VEANIQHGQQ VLCQRRTSPK PFTEEVLWNV WLEFSIKIKD LPKGALLNLQ IYCGKAPALS

301 SKASAESPSS ESKGKVRLLY YVNLLLIDHR FLLRRGEYVL HMWQISGKGE DQGSFNADKL

361 TSATNPDKEN SMSISILLDN YCHPIALPKH QPTPDPEGDR VRAEMPNQLR KQLEAIIATD

421 PLNPLTAEDK ELLWHFRYES LKHPKAYPKL FSSVKWGQQE IVAKTYQLLA RREVWDQSAL

481 DVGLTMQLLD CNFSDENVRA IAVQKLESLE DDDVLHYLLQ LVQAVKFEPY HDSALARFLL

541 KRGLRNKRIG HFLFWFLRSE IAQSRHYQQR FAVILEAYLR GCGTAMLHDF TQQVQVIEML

601 QKVTLDIKSL SAEKYDVSSQ VISQLKQKLE NLQNSQLPES FRVPYDPGLK AGALAIEKCK

661 VMASKKKPLW LEFKCADPTA LSNETIGIIF KHGDDLRQDM LILQILRIME SIWETESLDL

721 CLLPYGCIST GDKIGMIEIV KDATTIAKIQ QSTVGNTGAF KDEVLNHWLK EKSPTEEKFQ

781 AAVERFVYSC AGYCVATFVL GIGDRHNDNI MITETGNLFH IDFGHILGNY KSFLGINKER
```

```
841 VPFVLTPDFL FVMGTSGKKT SPHFQKFQDI CVKAYLALRH HTNLLIILFS MMLMTGMPQL

901 TSKEDIEYIR DALTVGKNEE DAKKYFLDQI EVCRDKGWTV QFNWFLHLVL GIKQGEKHSA

961 HHHHHH
```

PI3Kδ Construct and Protein

```
PI3Kδ    BV1060    p85iSH2(461-568)-GGGGGG-
                   p110δ(2-1044)-His
```

BV1060: PCR products for the inter SH2 domain (iSH2) of the p85 subunit and for the full-length p110δ subunit were generated and fused by overlapping PCR. The iSH2 PCR product was generated by using as a template the ORF318 (see above) and the primers gwG130-p03 (5'-GGGACAAG-TTTGTACAAAAAAGCAGGCTACGAAG-GAGATATACATATGC-GAGAATATGATAGATTATAT-GAAGAAT-3') (SEQ ID No. 7) and gwG154-p04 (5'-TCCTCCTCCT-CCTCCTCCTGGTTTAATGCTGTTCATACGTTTGTC-3') (SEQ ID No. 14). The p110δ fragment was obtained from first strand cDNA generated by RT-PCR from commercial human RNA from placenta, testis and brain (Clontech), using initially primers gwG154-p01 (5'-ATGCCCCCTGGGGTG-GACTGCCCCAT-3') (SEQ ID No. 15) and gwG154-p02 (5'-CTACTGCCTGT-TGTCTTTGGACACGT-3') (SEQ ID No. 16). In a subsequent PCR reaction linker sequences and a Histidine tag was added at the 5'end and 3'end of the p110δ fragment respectively, using primers gwG154-p03 (5'-AT-TAAACCAGGAGGAGGAGGAGGAGGAC-CCCCTGGGGTGGAC-TGCCCCATGGA-3') (SEQ ID No. 17) and gwG154-p06 (5'-AGCTCCGTGATGGTGATGGT-GAT-GTGCT-CCCTGCCTGTTGTCTTTGGACACGT-TGT-3') (SEQ ID No. 18). The p85-iSH2/p110δ fusion protein was assembled in a third PCR reaction by the overlapping linkers at the 3'end of the iSH2 fragment and the 5'end of the p110δ fragment, using the above mentioned gwG130-p03 primer and a primer containing an overlapping Histidine tag and the Gateway (Invitrogen) AttB2 recombination sequences (5'-GGG-ACCACTTTGTACAA-GAAAGCTGGGTTTAA-GCTCCGTGATGGTGATGGT-GAGTGCTCC-3') (SEQ ID No. 19). This final product was recombined in a Gateway OR reaction into the donor vector pDONR201 (Invitrogen) to generate the ORF319 entry clone. This clone was verified by sequencing and used in a Gateway LR reaction (Invitrogen) to transfer the insert into the Gateway adapted pBlueBac4.5 (Invitrogen) vector for generation of the baculovirus expression vector LR415.

Protein Sequence of BV1060:

```
                                                    (SEQ ID No. 20)
   1 MREYDRLYEE YTRTSQEIQM KRTAIEAFNE TIKIFEEQCQ TQERYSKEYI EKFKREGNEK

61 EIQRIMHNYD KLKSRISEII DSRRRLEEDL KKQAAEYREI DKRMNSIKPG GGGGGPPGVD

121 CPMEFWTKEE NQSVVVDFLL PTGVYLNFPV SRNANLSTIK QLLWHRAQYE PLFHMLSGPE

181 AYVFTCINQT AEQQELEDEQ RRLCDVQPFL PVLRLVAREG DRVKKLINSQ ISLLIGKGLH

241 EFDSLCDPEV NDFRAKMCQF CEEAAARRQQ LGWEAWLQYS FPLQLEPSAQ TWGPGTLRLP

301 NRALLVNVKF EGSEESFTFQ VSTKDVPLAL MACALRKKAT VFRQPLVEQP EDYTLQVNGR

361 HEYLYGSYPL CQFQYICSCL HSGLTPHLTM VHSSSILAMR DEQSNPAPQV QKPRAKPPPI

421 PAKKPSSVSL WSLEQPFRIE LIQGSKVNAD ERMKLVVQAG LFHGNEMLCK TVSSSEVSVC

481 SEPVWKQRLE FDINICDLPR MARLCFALYA VIEKAKKARS TKKKSKKADC PIAWANLMLF

541 DYKDQLKTGE RCLYMWPSVP DEKGELLNPT GTVRSNPNTD SAAALLICLP EVAPHPVYYP

601 ALEKILELGR HSECVHVTEE EQLQLREILE RRGSGELYEH EKDLVWKLRH EVQEHFPEAL

661 ARLLLVTKWN KHEDVAQMLY LLCSWPELPV LSALELLDFS FPDCHVGSFA IKSLRKLTDD

721 ELFQYLLQLV QVLKYESYLD CELTKFLLDR ALANRKIGHF LFWHLRSEMH VPSVALRFGL

781 ILEAYCRGST HHMKVLMKQG EALSKLKALN DFVKLSSQKT PKPQTKELMH LCMRQEAYLE

841 ALSHLQSPLD PSTLLAEVCV FQCTFMDSKM KPLWIMYSNE EAGSGGSVGI IFKNGDDLRQ

901 DMLTLQMIQL MDVLWKQEGL DLRMTPYGCL PTGDRTGLIE VVLRSDTIAN IQLNKSNMAA

961 TAAFNKDALL NWLKSKNPGE ALDRAIEEFT LSCAGYCVAT YVLGIGDRHS DNIMIRESGQ

1021 LFHIDFGHFL GNFKTKFGIN RERVPFILTY DFVHVIQQGK TNNSEKFERF RGYCERAYTI

1081 LRRHGLLFLH LFALMRAAGL PELSCSKDIQ YLKDSLALGK TEEEALKHFR VKFNEALRES

1141 WKTKVNWLAH NVSKDNRQEL GGAHHHHHH
```

Purification of PI3Kα, PI3Kβ and PI3Kγ Constructs

PI3Kα, PI3Kβ and PI3Kγ were purified in two chromatographic steps: immobilized metal affinity chromatography (IMAC) on a Ni sepharose resin (GE Healthcare) and gel filtration utilizing a Superdex 200 26/60 column (GE Healthcare). All buffers were chilled to 4° C. and lysis was performed chilled on ice. Column fractionation was performed at room temperature. All buffers used to purify PI3Kβ contained 0.05% Triton X100 in addition to what is described below.

Typically frozen cells from 10 L of Tn5 cell culture were resuspended in "Lysis Buffer" 20 mM Tris-Cl, pH 7.5, 500 mM NaCl, 5% glycerol, 5 mM imidazole, 1 mM NaF, 0.1ug/mL okadaic acid (OAA), 5 mM BME, 1× Complete protease inhibitor cocktail—EDTA-free (20 tablets/1 L buffer, Roche Applied Sciences), benzonase (25 U/mL buffer, EMD Biosciences) at a ratio of 1:6 v/v pellet to Lysis Buffer ratio, and mechanically lysed by douncing 20 strokes using a tight-fitting pestle. The lysate was centrifuged at 45,000 g for 30 minutes, and the supernatant was loaded onto a pre-equilibrated IMAC column (3 mL resin/100 mL lysate). The column was washed with 3-5 column volumes of Lysis Buffer, followed by a second wash of 3-5 column volumes with 20 mM Tris-Cl, pH 7.5, 500 mM NaCl, 5% glycerol, 45 mM imidazole, 1 mM NaF, 0.1 μg/mL OAA, 5 mM BME, 1× Complete protease inhibitor cocktail—EDTA-free. Protein was eluted with 20 mM Tris-Cl, pH 7.5, 0.5 M NaCl, 5% glycerol, 250 mM imidazole, 1 mM NaF, 0.1 μg/mL OAA, 5 mM BME, 1× Complete protease inhibitor cocktail—EDTA-free. Pertinent fractions were analyzed by SDS-PAGE and pooled accordingly. The protein was further purified by gel filtration on a Superdex 200 26/60 column equilibrated in 20 mM Tris-Cl, pH 7.5, 0.5 M NaCl, 5% glycerol, 1 mM NaF, 5 mM DTT, 1× Complete protease inhibitor cocktail—EDTA-free. Pertinent fractions were analyzed by SDS-PAGE and pooled accordingly. An equal volume of Dialysis Buffer (20 mM Tris-Cl, pH 7.5, 500 mM NaCl, 50% glycerol, 5 mM NaF, 5 mM DTT) was added to the pool and than dialyzed against Dialysis Buffer two changes (one change overnight). Protein was stored at −20° C.

Purification of PI3Kδ

PI3Kδ was purified in three chromatographic steps: immobilized metal affinity chromatography on a Ni Sepharose resin (GE Healthcare), gel filtration utilizing a Superdex 200 26/60 column (GE Healthcare), and finally a ion exchange step on a Q-HP column (GE Healthcare). All buffers were chilled to 4° C. and lysis was performed chilled on ice. Column fractionation was performed at room temperature.

Typically frozen cells from 10 L of Tn5 cell culture were resuspended in "Lysis Buffer" 20 mM Tris-Cl, pH 7.5, 500 mM NaCl, 5% glycerol, 5 mM imidazole, 1 mM NaF, 0.1 μg/mL okadaic acid (OAA), 5 mM BME, 1× Complete protease inhibitor cocktail—EDTA-free (20 tablets/1 L buffer, Roche Applied Sciences), benzonase (25 U/mL lysis buffer, EMD Biosciences) at a ratio of 1:10 v/v pellet to Lysis Buffer ratio, and mechanically lysed by douncing 20 strokes using a tight-fitting pestle. The lysate was centrifuged at 45,000 g for 30 minutes, and the supernatant was loaded onto a pre-equilibrated IMAC column (5 mL resin/100 mL lysate). The column was washed with 3-5 column volumes of Lysis Buffer, followed by a second wash of 3-5 column volumes with 20 mM Tris-Cl, pH 7.5, 500 mM NaCl, 5% glycerol, 40 mM imidazole, 1 mM NaF, 0.1 ug/mL OAA, 5 mM BME, 1× Complete protease inhibitor cocktail—EDTA-free. Protein was eluted with 20 mM tris-Cl, pH 7.5, 500 mM NaCl, 5% glycerol, 250 mM imidazole, 1 mM NaF, 0.1 μg/mL OAA, 5 mM BME, 1× Complete protease inhibitor cocktail—EDTA-free. Pertinent fractions were analyzed by SDS-PAGE and pooled accordingly. The protein was further purified by gel filtration on a Superdex 200 equilibrated in 20 mM Tris-Cl, pH 7.5, 500 mM NaCl, 5% glycerol, 1 mM NaF, 0.1 μg/mL OAA, 5 mM DTT, 1× Complete protease inhibitor cocktail—EDTA-free. Pertinent fractions were analyzed by SDS-PAGE and pooled accordingly. These fractions were diluted 1:10 v/v pool volume to buffer ratio with "Buffer A" 20 mM tris-Cl, pH 8.2, 5% glycerol, 1 mM NaF, 0.1 μg/mL OAA, 5 mM DTT and loaded onto a prepared Q-HP column. After sample loading is completed we wash with Buffer A and 5% "Buffer B" 20 mM tris-Cl, pH 8.2, 1 M NaCl, 5% glycerol, 1 mM NaF, 0.1 ug/mL OAA, 5 mM DTT for 3-5 column volumes. We elute the protein using a 5%-30% gradient of Buffer B. Typically the protein elutes at ~200 mM NaCl. Pertinent fractions were analyzed by SDS-PAGE and pooled accordingly. An equal volume of Dialysis Buffer (20 mM tris-Cl, pH 7.5, 500 mM NaCl, 50% glycerol, 1 mM NaF, 0.1 μg/mL OAA, 5 mM DTT) was added to the pool and then dialyzed against Dialysis Buffer two changes (one change overnight). Protein was stored at −20° C.

The following results were obtained using the above described assays.

| Example no. | PI3Kalpha/IC50 [umol l-1] | PI3Kbeta/IC50 [umol l-1] | PI3Kgamma/IC50 [umol l-1] | PI3Kdelta/IC50 [umol l-1] |
|---|---|---|---|---|
| 1 | 0.004 | 1.238 | 0.067 | 0.18 |
| 2 | 0.0055 | 0.332 | 0.09 | 0.03 |
| 3 | 0.045 | 0.127 | 1.59 | 0.74 |
| 4 | 0.0065 | 0.143 | 0.176 | 0.22 |
| 5 | 0.0055 | 0.047 | 0.153 | 0.046 |
| 6 | 0.016 | 1.63 | 0.50 | 0.47 |
| 7 | 0.0235 | 3.136 | 0.233 | 0.051 |
| 8 | 0.0095 | 0.276 | 0.180 | 0.198 |
| 9 | 0.0085 | 0.087 | 0.141 | 0.072 |
| 10 | 0.018 | 0.449 | 0.282 | 0.054 |
| 11 | 0.005 | 0.047 | 0.129 | 0.018 |
| 12 | 0.006 | 0.516 | 0.230 | 0.053 |
| 13 | 0.009 | 0.277 | 0.104 | 0.118 |
| 14 | 0.004 | 0.268 | 0.191 | 0.016 |
| 16 | 0.0055 | 0.297 | 0.074 | 0.060 |
| 17 | 0.008 | 0.389 | 0.153 | 0.236 |
| 18 | 0.0105 | 0.374 | 0.155 | 0.028 |
| 19 | 0.0055 | 0.588 | 0.123 | 0.077 |
| 20 | 0.0035 | 0.155 | 0.080 | 0.011 |
| 21 | <0.003 | 0.519 | 0.237 | 0.036 |

-continued

| Example no. | PI3Kalpha/IC50 [umol l-1] | PI3Kbeta/IC50 [umol l-1] | PI3Kgamma/IC50 [umol l-1] | PI3Kdelta/IC50 [umol l-1] |
|---|---|---|---|---|
| 22 | 0.0235 | 6.905 | 0.262 | 1.895 |
| 24 | 0.007 | 0.135 | 0.098 | 0.024 |
| 25 | 0.0055 | 0.346 | 0.122 | 0.045 |
| 26 | 0.0065 | 0.328 | 0.138 | 0.058 |
| 27 | 0.0045 | 0.397 | 0.097 | 0.072 |
| 28 | 0.0155 | 2.035 | 0.336 | 0.331 |
| 29 | 0.008 | 0.721 | 1.358 | 0.892 |
| 30 | 0.023 | 2.135 | 0.119 | 0.294 |
| 31 | 0.0515 | 5.825 | 1.226 | 1.940 |
| 32 | 0.007 | 1.092 | 0.131 | 0.043 |
| 33 | 0.0695 | 5.079 | 0.909 | 0.860 |
| 34 | 0.0125 | 1.818 | 0.166 | 0.156 |
| 35 | 0.009 | 2.908 | 0.195 | 0.354 |
| 36 | 0.012 | 0.51 | n.d. | 0.04 |
| 37 | 0.004 | 0.182 | n.d. | 0.019 |
| 38 | 0.009 | 0.866 | n.d. | 0.044 |
| 39 | 0.013 | 1.612 | 0.334 | 0.265 |
| 41 | 0.024 | 3.046 | n.d. | 0.496 |
| 42 | 0.008 | 0.409 | n.d. | 0.032 |
| 43 | 0.005 | 0.771 | n.d. | 0.045 |
| 44 | 0.007 | 0.073 | n.d. | 0.049 |
| 45 | 0.0065 | 0.061 | n.d. | 0.024 |
| 46 | 0.0055 | 1.148 | n.d. | 0.157 |
| 47 | 0.003 | 6.168 | n.d. | 1.620 |
| 48 | 0.006 | 0.920 | n.d. | 0.019 |
| 49 | 0.004 | 1.248 | n.d. | 0.101 |
| 50 | 0.009 | 0.555 | n.d. | 0.113 |
| 51 | 0.005 | 3.285 | n.d. | 0.278 |

The invention claimed is:
1. A compound of formula I

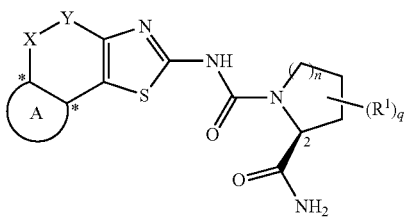

wherein,
A is an unsubstituted or substituted aryl ring or unsubstituted or substituted heterocyclic ring fused to the rest of the molecule at the positions indicated by the symbol *;
X-Y is $(CH_2)_r$ or $O(CH_2)_t$ or $(CH_2)_tO$ wherein,
r is 1, 2 or 3;
t is 1 or 2;
n is 0, 1 or 2;
q is 0, 1, 2, 3 or 4;
$R^1$ represents, independently at each occurrence,
  halo;
  hydroxy;
  unsubstituted or substituted aryl;
  unsubstituted amino or di($C_1$-$C_7$-alkyl)amino;
  unsubstituted $C_1$-$C_7$-alkyl;
  $C_1$-$C_7$-alkyl, which is substituted one or more times by hydroxy, $C_1$-$C_7$-alkoxy, unsubstituted or substituted amino, aryl or heterocyclyl, and wherein aryl may be mono or poly-substituted by halo; or
two $R^1$ substituents together form an alkandiyl to form a cyclic moiety, optionally substituted by hydroxy or halo,
or a pharmaceutically acceptable salt thereof; with the proviso that the compound is not a prodrug or in the form of hydrates or solvates.

2. The compound according to claim 1, wherein Ring A is substituted by one, two or three substituents independently selected at each occurrence from,
  unsubstituted or substituted $C_1$-$C_7$-alkyl;
  unsubstituted amino or di($C_1$-$C_7$-alkyl)amino;
  unsubstituted or substituted $C_3$-$C_7$-cycloalkyl,
or a pharmaceutically acceptable salt thereof.

3. The compound according to claim 1, wherein the ring A substituent is selected from
  unsubstituted $C_1$-$C_7$-alkyl;
  di($C_1$-$C_7$-alkyl)amino;
  $C_1$-$C_7$-alkyl substituted one or more times by $C_3$-$C_7$-cycloalkyl or halo;
  unsubstituted $C_3$-$C_7$-cycloalkyl;
  $C_1$-$C_7$-cycloalkyl which is substituted one or more times by halo, (halo-$C_1$-$C_7$-alkyl) or $C_1$-$C_7$-alkyl,
or a pharmaceutically acceptable salt thereof.

4. The compound according to claim 1, wherein ring A is an unsubstituted or substituted 5- or 6-membered ring containing 1 or 2 heteroatoms selected from N, S or O, wherein at least one heteroatom is N, or a pharmaceutically acceptable salt thereof.

5. The compound according to claim 1, wherein ring A is selected from an unsubstituted or substituted pyridine ring, unsubstituted or substituted pyrimidine ring or unsubstituted or substituted thiazole ring,
or a pharmaceutically acceptable salt thereo 6. The compound according to claim 1, wherein X-Y represents $(CH_2)_r$ or $O(CH_2)_t$ wherein r is 2 and t is 1.

7. The compound according to claim 1, wherein $R^1$ represents, independently at each occurrence,
  halo;
  hydroxy;
  unsubstituted or substituted phenyl;
  di($C_1$-$C_7$-alkyl)amino;
  unsubstituted $C_1$-$C_7$-alkyl;
  $C_1$-$C_7$-alkyl, which is substituted one or more times by hydroxy, $C_1$-$C_7$-alkoxy, di($C_1$-$C_7$-alkyl)amino, di-(perdeutero$C_1$-$C_7$-alkyl)amino, phenyl, morpholinyl, acetylamino, or N—($C_1$-$C_7$-alkyl)-N-(phenyl$C_1$-$C_7$-alkyl) amino, and wherein independently each phenyl may be mono or poly-substituted by halo.

8. The compound according to claim 1, wherein n is 1 and q is 1.

9. The compound according to claim 1, selected from:
(2S,4R)-4-Dimethylamino-pyrrolidine-1,2-dicarboxylic acid 2-amide 1-[(8-tert-butyl-4,5-dihydro-thiazolo[4,5-h]quinazolin-2-yl)-amide];
(2S,3S)-3-Methyl-pyrrolidine-1,2-dicarboxylic acid 2-amide 1-[(8-diethylamino-4,5-dihydro-thiazolo[4,5-h]quinazolin-2-yl)-amide];
(R)-2-Benzyl-pyrrolidine-1,2-dicarboxylic acid 2-amide 1-[(8-diethylamino-4,5-dihydro-thiazolo[4,5-h]quinazolin-2-yl)-amide];
(S)-2-Methyl-pyrrolidine-1,2-dicarboxylic acid 2-amide 1-[(8-diethylamino-4,5-dihydro-thiazolo[4,5-h]quinazolin-2-yl)-amide];
(R)-2-Methoxymethyl-pyrrolidine-1,2-dicarboxylic acid 2-amide 1-[(8-diethylamino-4,5-dihydro-thiazolo[4,5-h]quinazolin-2-yl)-amide];

(R)-2-Dimethylaminomethyl-pyrrolidine-1,2-dicarboxylic acid 2-amide 1-[(8-tert-butyl-4,5-dihydro-thiazolo[4,5-h]quinazolin-2-yl)-amide];

$d_6$-(R)-2-Dimethylaminomethyl-pyrrolidine-1,2-dicarboxylic acid 2-amide 1-[(8-tert-butyl-4,5-dihydro-thiazolo[4,5-h]quinazolin-2-yl)-amide];

(R)-2-Hydroxymethyl-pyrrolidine-1,2-dicarboxylic acid 2-amide 1-[(8-diethylamino-4,5-dihydro-thiazolo[4,5-h]quinazolin-2-yl)-amide]

(R)-2-Hydroxymethyl-pyrrolidine-1,2-dicarboxylic acid 2-amide 1-[(8-tert-butyl-4,5-dihydro-thiazolo[4,5-h]quinazolin-2-yl)-amide]

(R)-2-{[(3-Fluoro-benzyl)-methyl-amino]-methyl}-pyrrolidine-1,2-dicarboxylic acid 2-amide 1-[(8-tert-butyl-4,5-dihydro-thiazolo[4,5-h]quinazolin-2-yl)-amide];

(S)-2-Methyl-pyrrolidine-1,2-dicarboxylic acid 2-amide 1-[(8-tert-butyl-4,5-dihydro-thiazolo[4,5-h]quinazolin-2-yl)-amide];

(S)-Pyrrolidine-1,2-dicarboxylic acid 2-amide 1-[(8-diethylamino-4,5-dihydro-thiazolo[4,5-h]quinazolin-2-yl)-amide];

(S)-Azetidine-1,2-dicarboxylic acid 2-amide 1-[(8-diethylamino-4,5-dihydro-thiazolo[4,5-h]quinazolin-2-yl)-amide];

(S)-Pyrrolidine-1,2-dicarboxylic acid 2-amide 1-[(8-tert-butyl-4,5-dihydro-thiazolo[4,5-h]quinazolin-2-yl)-amide];

5-Methyl-pyrrolidine-1,2-dicarboxylic acid 2-amide 1-[(8-diethylamino-4,5-dihydro-thiazolo[4,5-h]quinazolin-2-yl)-amide];

(2S,4R)-4-Fluoro-pyrrolidine-1,2-dicarboxylic acid 2-amide 1-[(8-diethylamino-4,5-dihydro-thiazolo[4,5-h]quinazolin-2-yl)-amide];

(2S,4S)-4-Fluoro-pyrrolidine-1,2-dicarboxylic acid 2-amide 1-[(8-diethylamino-4,5-dihydro-thiazolo[4,5-h]quinazolin-2-yl)-amide];

(1S,5R)-2-Aza-bicyclo[3.1.0]hexane-1,2-dicarboxylic acid 1-amide 2-[(8-tert-butyl-4,5-dihydro-thiazolo[4,5-h]quinazolin-2-yl)-amide];

(1S,5R)-2-Aza-bicyclo[3.1.0]hexane-1,2-dicarboxylic acid 1-amide 2-[(8-diethylamino-4,5-dihydro-thiazolo[4,5-h]quinazolin-2-yl)-amide];

(2S,3R)-3-Methyl-pyrrolidine-1,2-dicarboxylic acid 2-amide 1-[(8-tert-butyl-4,5-dihydro-thiazolo[4,5-h]quinazolin-2-yl)-amide];

(2S,3R)-3-Methyl-pyrrolidine-1,2-dicarboxylic acid 2-amide 1-[(8-diethylamino-4,5-dihydro-thiazolo[4,5-h]quinazolin-2-yl)-amide];

(2S,4S)-4-Dimethylamino-pyrrolidine-1,2-dicarboxylic acid 2-amide 1-[(8-diethylamino-4,5-dihydro-thiazolo[4,5-h]quinazolin-2-yl)-amide];

5-Phenyl-pyrrolidine-1,2-dicarboxylic acid 2-amide 1-[(8-diethylamino-4,5-dihydro-thiazolo[4,5-h]quinazolin-2-yl)-amide];

Azetidine-1,2-dicarboxylic acid 2-amide 1-[(8-tert-butyl-4,5-dihydro-thiazolo[4,5-h]quinazolin-2-yl)-amide];

(S)-Azetidine-1,2-dicarboxylic acid 2-amide 1-[(8-tert-butyl-4,5-dihydro-thiazolo[4,5-h]quinazolin-2-yl)-amide];

(2S,4S)-4-Hydroxy-pyrrolidine-1,2-dicarboxylic acid 2-amide 1-[(8-diethylamino-4,5-dihydro-thiazolo[4,5-h]quinazolin-2-yl)-amide];

(2S,4R)-4-Hydroxy-pyrrolidine-1,2-dicarboxylic acid 2-amide 1-[(8-diethylamino-4,5-dihydro-thiazolo[4,5-h]quinazolin-2-yl)-amide];

(S)-Pyrrolidine-1,2-dicarboxylic acid 2-amide 1-[(7-tert-butyl-4,5-dihydro-benzo[1,2-d;3,4-d']bisthiazol-2-yl)-amide];

(S)-2-Methyl-pyrrolidine-1,2-dicarboxylic acid 2-amide 1-[(7-tert-butyl-4,5-dihydro-benzo[1,2-d;3,4-d']bisthiazol-2-yl)-amide];

(S)-Azetidine-1,2-dicarboxylic acid 2-amide 1-[(7-tert-butyl-4,5-dihydro-benzo[1,2-d;3,4-d']bisthiazol-2-yl)-amide];

(2S,4R)-4-Dimethylamino-pyrrolidine-1,2-dicarboxylic acid 2-amide 1-[(7-tert-butyl-4,5-dihydro-benzo[1,2-d;3,4-d']bisthiazol-2-yl)-amide];

(S)-Pyrrolidine-1,2-dicarboxylic acid 2-amide 1-{[7-(2-fluoro-1,1-dimethyl-ethyl)-4,5-dihydro-benzo[1,2-d;3,4-d']bisthiazol-2-yl]-amide};

(S)-Pyrrolidine-1,2-dicarboxylic acid 2-amide 1-[(7-cyclopropylmethyl-4,5-dihydro-benzo[1,2-d;3,4-d']bisthiazol-2-yl)-amide];

(2S,3S)-3-Methyl-pyrrolidine-1,2-dicarboxylic acid 2-amide 1-[(7-tert-butyl-4,5-dihydro-benzo[1,2-d;3,4-d']bisthiazol-2-yl)-amide];

(1S,5R)-2-Aza-bicyclo[3.1.0]hexane-1,2-dicarboxylic acid 1-amide 2-[(7-tert-butyl-4,5-dihydro-benzo[1,2-d;3,4-d']bisthiazol-2-yl)-amide];

(2S,3S)-3-(Acetylamino-methyl)-pyrrolidine-1,2-dicarboxylic acid 2-amide 1-[(8-tert-butyl-4,5-dihydro-thiazolo[4,5-h]quinazolin-2-yl)-amide];

(2S,3S)-3-Morpholin-4-ylmethyl-pyrrolidine-1,2-dicarboxylic acid 2-amide 1-[(8-tert-butyl-4,5-dihydro-thiazolo[4,5-h]quinazolin-2-yl)-amide];

(2S,3R)-3-Hydroxy-pyrrolidine-1,2-dicarboxylic acid 2-amide 1-[(8-tert-butyl-4,5-dihydro-thiazolo[4,5-h]quinazolin-2-yl)-amide];

(2S,3R)-3-Methyl-pyrrolidine-1,2-dicarboxylic acid 2-amide 1-[(7-tert-butyl-4,5-dihydro-benzo[1,2-d;3,4-d']bisthiazol-2-yl)-amide];

(2S,3R)-3-Methyl-pyrrolidine-1,2-dicarboxylic acid 2-amide 1-[(8-methyl-4H-5-oxa-1-thia-3,7-diaza-cyclopenta[a]naphthalen-2-yl)-amide];

(2S,3S)-3-Morpholin-4-ylmethyl-pyrrolidine-1,2-dicarboxylic acid 2-amide 1-[(7-tert-butyl-4,5-dihydro-benzo[1,2-d;3,4-d']bisthiazol-2-yl)-amide];

(2S,3R)-3-Methoxymethyl-pyrrolidine-1,2-dicarboxylic acid 2-amide 1[(8-tert-butyl-4,5-dihydro-thiazolo[4,5-h]quinazolin-2-yl)-amide];

(2S,3S)-3-Dimethylaminomethyl-pyrrolidine-1,2-dicarboxylic acid 2-amide 1-[(8-tert-butyl-4,5-dihydro-thiazolo[4,5-h]quinazolin-2-yl)-amide];

(2S,3R)-3-Methyl-pyrrolidine-1,2-dicarboxylic acid 2-amide 1-{[8-(2,2,2-trifluoro-1,1-dimethyl-ethyl)-4,5-dihydro-thiazolo[4,5-h]quinazolin-2-yl]-amide};

(2S,3R)-3-Methoxymethyl-pyrrolidine-1,2-dicarboxylic acid 2-amide 1-{[8-(2,2,2-trifluoro-1,1-dimethyl-ethyl)-4,5-dihydro-thiazolo[4,5-h]quinazolin-2-yl]-amide};

(2S,3R)-3-Methyl-pyrrolidine-1,2-dicarboxylic acid 2-amide 1-[(8-tert-butyl-4H-5-oxa-1-thia-3,7-diaza-cyclopenta[a]naphthalen-2-yl)-amide];

(2S,3S)-3-Dimethylaminomethyl-pyrrolidine-1,2-dicarboxylic acid 2-amide 1-[(8-tert-butyl-4H-5-oxa-1-thia-3,7-diaza-cyclopenta[a]naphthalen-2-yl)-amide];

(2S,3R)-3-Methyl-pyrrolidine-1,2-dicarboxylic acid 2-amide 1-{[8-(2,2,2-trifluoro-1,1-dimethyl-ethyl)-4H-5-oxa-l-thia-3,7-diaza-cyclopenta[a]naphthalen-2-yl]-amide};

(2S,3R)-3-Methyl-pyrrolidine-1,2-dicarboxylic acid 2-amide 1-{[7-(2,2,2-trifluoro-1,1-dimethyl-ethyl)-4,5-dihydro-benzo[1,2-d;3,4-d']bisthiazol-2-yl]-amide};

(2S,3R)-3-Methoxymethyl-pyrrolidine-1,2-dicarboxylic acid 2-amide 1-{[7-(2,2,2-trifluoro-1,1-dimethyl-ethyl)-4,5-dihydro-benzo[1,2-d;3,4-d']bisthiazol-2-yl]-amide};

(2S,3S)-3-Dimethylaminomethyl-pyrrolidine-1,2-dicarboxylic acid 2-amide 1-[(7-tert-butyl-4,5-dihydro-benzo[1,2-d;3,4-d']bisthiazol-2-yl)-amide].

10. A pharmaceutical composition comprising a compound of formula (I), according to claim 1, or a pharmaceutically acceptable salt thereof, and optionally a further therapeutic agent, together with a pharmaceutically acceptable carrier.

11. A compound of formula:

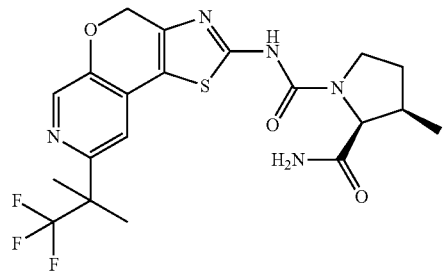 [SMILES: C[C@@H]1CCN(C(=O)Nc2nc3c(s2)-c2cc(C(C)(C)C(F)(F)F)ncc2OC3)[C@@H]1C(N)=O]

or a pharmaceutically acceptable salt thereof.

* * * * *